(12) United States Patent
Guenzler-Pukall et al.

(10) Patent No.: US 8,466,172 B2
(45) Date of Patent: *Jun. 18, 2013

(54) STABILIZATION OF HYPOXIA INDUCIBLE FACTOR (HIF) ALPHA

(75) Inventors: Volkmar Guenzler-Pukall, San Leandro, CA (US); Thomas B. Neff, Atherton, CA (US); Qingjian Wang, Belmont, CA (US); Michael P. Arend, Foster City, CA (US); Lee A. Flippin, Woodside, CA (US); Alex Melekhov, Irvine, CA (US)

(73) Assignee: FibroGen, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/928,119

(22) Filed: Dec. 2, 2010

(65) Prior Publication Data
US 2011/0166145 A1 Jul. 7, 2011

Related U.S. Application Data

(63) Continuation of application No. 11/494,978, filed on Jul. 28, 2006, now abandoned, which is a continuation of application No. 10/313,551, filed on Dec. 6, 2002, now abandoned.

(60) Provisional application No. 60/386,488, filed on Jun. 5, 2002, provisional application No. 60/359,683, filed on Feb. 25, 2002, provisional application No. 60/349,659, filed on Jan. 16, 2002, provisional application No. 60/337,082, filed on Dec. 6, 2001.

(51) Int. Cl.
*A01N 43/42* (2006.01)
*A01N 43/40* (2006.01)
*A61K 31/47* (2006.01)
*A61K 31/44* (2006.01)
*C07D 217/00* (2006.01)

(52) U.S. Cl.
USPC ............ 514/307; 514/311; 514/354; 546/146

(58) Field of Classification Search
USPC .......................... 514/307, 311, 354; 546/146
See application file for complete search history.

(56) References Cited

U.S. PATENT DOCUMENTS

| | | | |
|---|---|---|---|
| 5,607,954 A | 3/1997 | Weidmann et al. |
| 5,610,172 A | 3/1997 | Weidmann et al. |
| 5,620,995 A | 4/1997 | Weidmann et al. |
| 5,620,996 A | 4/1997 | Weidmann et al. |
| 5,658,933 A | 8/1997 | Weidmann et al. |
| 5,719,164 A | 2/1998 | Weidmann et al. |
| 5,726,305 A | 3/1998 | Weidmann et al. |
| 5,916,898 A | 6/1999 | Edwards et al. |
| 6,020,350 A | 2/2000 | Weidmann et al. |
| 6,093,730 A | 7/2000 | Weidmann et al. |
| 6,200,974 B1 | 3/2001 | Edwards et al. |
| 6,566,088 B1 | 5/2003 | McKnight et al. |

FOREIGN PATENT DOCUMENTS

| | | |
|---|---|---|
| EP | 0 650 960 B1 | 3/1997 |
| EP | 0 650 961 B1 | 3/1997 |
| EP | 0 878 480 A1 | 11/1998 |
| WO | WO-00/50390 A1 | 8/2000 |
| WO | WO-02/074249 A2 | 9/2002 |
| WO | WO-02/074980 A2 | 9/2002 |
| WO | WO-02/074981 A2 | 9/2002 |
| WO | WO-02/089799 A2 | 11/2002 |
| WO | WO-02/089809 A1 | 11/2002 |

OTHER PUBLICATIONS

Abdel-Gayoum, A.A., et al., "Hyperlipidaemia in Cisplatin-Induced Nephrotic Rats," Human Exp. Toxicology (1999) 18:454-459.
Adams, M.D., et al., "The Genome Sequence of *Drosophila melanogaster*," NCBI Sequence Viewer (2002) Genbank Accession No. AA F52050.
Ahn, S.T. and Mustoe, T.A., "Effects of Ischemia on Ulcer Wound Healing: A New Model in the Rabbit Ear," Ann. Plastic Surgery (1990) 24(1):17-23.
Appel, Gerald, "Lipid Abnormalities in Renal Disease," Kidney Int (1991) 39:169-183.
Aravind, L. and Koonin, E.V., "The DNA Repair Protein AlkB, EGLN-9 and Leprecan Define New Families of 2-Oxoglutarate- and Iron-Dependent Dioxygenases," Genome Biol. (2001) 2(3):0007.1-0007.8.
Arteel, Gavin E., et al., "Chronic Enteral Ethanol Treatment Causes Hypoxia in Rat Liver Tissue in Vivo," Hepatology (1997) 25(4):920-926.
Bergeron, Marcelle, et al., "Role of Hypoxia-Inducible Factor-1 in Hypoxia-Induced Ischemic Tolerance m Neonatal Rat Brain," Ann. Neurol (2000) 48(3):285-296.
Bickel, Martin, et al., "Selective Inhibition of Hepatic Collagen Accumulation in Experimental Liver Fibrosis in Rats by a New Prolyl 4-Hydroxylase Inhibitor," Hepatology (1998) 28(2):404-411.
Bocker-Meffert, Simone, et al.,"Erythropoietin and VEGF Promote Neural Outgrowth From Retinal Explants in Postnatal Rats," Invest. Ophthamol. & Visual Science (2002) 43(6):2021-2026.
Bruick, R.K. and McKnight, S.L., "A Conserved Family of Prolyl-4-Hydroxylases That Modify HIF," (2001) Science 294:1337-1340.
Buemi, M. et al.,"Erythropoietin and the Brain: From Neurodevelopment to Neuroprotection," Clin. Science (2002) 103:272-282.
Carmeliet, Peter, et al.,"Role of HIF-1α in Hypoxia-Mediated Apoptosis, Cell Proliferation and Tumor Angiogenesis," Nature (1998) 394:485-490.
Cockman, Matthew E., et al.,"Hypoxia-Inducible Factor-α Binding and Ubiquitylation by the von Hippel-Lindau Tumor Suppressor Protein," J Biol. Chem. (2000) 275(33):25733-25741.
Corral, Claudio J., et al., "Vascular Endothelial Growth Factor is More Important Than Basic Fibroblastic Growth Factor Ischemic Wound Healing," Arch. Surg. (1999) 134:200-205.

(Continued)

Primary Examiner — Samira Jean-Louis
(74) Attorney, Agent, or Firm — Leanne C. Price, Esq.

(57) ABSTRACT

The present invention relates to methods of stabilizing the alpha subunit of hypoxia inducible factor (HIF). The invention further relates to methods of preventing, pretreating, or treating conditions associated with HIF, including ischemic and hypoxic conditions. Compounds for use in these methods are also provided.

8 Claims, 15 Drawing Sheets

OTHER PUBLICATIONS

Cunliffe, C. Jane, et al., "Assay of Prolyl 4-Hydroxylase by the Chromatographic Determination of [14C] succinic Acid on Ion-Exchange Minicolumns," Biochem. J (1986) 240:617-619.

Darby, C., et al,"Lethal Paralysis of *Caenorhabditis elegans* by *Pseudomonas aeruginoas*," NCBI Sequence Viewer (1999) Genbank Accession No. AAD56365.

Dawson, Ted M., "Preconditioning-Mediated Neuroprotection Through Erythropoietin ," Lancet (2002) 359:96-97.

Deindl, E. and Schaper, W., "Gene Expression After Short Periods of Coronary Occlusion," Mol. Cell Biochem. (1998) 186:43-51.

Detmar, Michael, et al., "Increased Microvascular Density and Enhanced Leukocyte Rolling and Adhesion in the Skin of VEGF Transgenic Mice," J Invest. Dermatology (1998) 111:1-6.

Dupuy, Denis, et al., "Mapping, Characterization and Expression Analysis of the SM-20 Human Homologue, C1orf12, and Identification of a Novel Related Gene, SCAND2," Genomic (2000) 69:348-354.

Dupuy, D., et al., "Mapping, Characterization and Expression Analysis of the SM-20 Human Homologue, C1orf12, and Identification of a Novel Related Gene, SCAND2," NCBI Sequence Viewer (2000) Genbank Accession No. AAG33965.

Elkins, Jonathan M., et al., "Structure of Factor-Inhibiting Hypoxia-Inducible Factor (HIF) Reveals Mechanism of Oxidative Modification of HIF-α," J. Biol. Chem (2003) 278(3):1802-1806.

Elson, David A., et al., "Induction of Hypervascularity Without Leakage or Inflammation in Transgenic Mice Overexpressing Hypoxia-Inducible Factor-1α," Genes Dev. (2001) 15:2520-2532.

Ema, M., et al., NCBI Sequence Viewer (1999) Genbank Accession No. BAA20130.

Epstein, Andrew C.R., et al., "*C elegans* EGL-9 and Mammalian Homologs Define a Family of Dioxygenases That Regulate HIF by Prolyl Hydroxylation," Cell (2001) 107:43-54.

Franklin, Trevor J., et al., "Approaches to the Design of Anti-Fibrotic Drugs," Biochem. Soc. Trans. (1991) 19:812-815.

Franklin, Trevor J., et al., "Inhibition of Prolyl 4-Hyrdroxylase in Vitro and in Vivo by Members of a Novel Series of Phenanthrolinones," Biochem. J (2001) 353:333-338.

Friedman, Lisa, et al., "Prolyl 4-Hyrdroxylase is Required for Viability and Morphogenesis in *Caenorhabditis elegans*," PNAS (2000) 97(9):4736-4741.

Gorio, Alfredo, et al., "Recombinant Human Erythropoietin Counteracts Secondary Injury and Markedly Enhances Neurological Recovery From Experimental Spinal Cord Trauma," PNAS (2002) 9999(14):9450-9455.

Gu, Y.Z., et al., "Molecular Characterization and Chromosomal Localization of a Third Alpha-Class Hypoxia-Inducible Factor Subunit, HIF3Alpha," NCBI Sequence Viewer (2001) Genbank Accession No. AAC72734.

Hara, S., et al., "Molecular Cloning of cDNAs Encoding Hypoxia-Inducible Factor HIF-1α and -2α of Bovine Arterial Endothelial Cells," NCBI Sequence Viewer (1999) Genbank Accession No. BAA78675.

Huang, L. Eric., et al., "Regulation of Hypoxia-Inducible Factor 1α is Mediated by an O2-Dependent Degradation Domain via the Ubiquitin-Proteasome Pathway," Proc. Natl. Acad. Sci. (1998) 95:7987-7992.

Iliopoulos, Othon, et al., "Negative Regulation of Hypoxia-Inducible Genes by the von Hippel-Lindau Protein," Proc. Natl. Acad. Sci. (1996) 93:10595-10599.

Ivan, Mircea, et al., "HIF Targeted for VHL-Mediated Destruction by Proline Hydroxylation: Implications for O2 Sensing," Science (2001) 292:464-468.

Jaakkola, Panu, et al., "Targeting of HIFα to the von Hippel-Lindau Ubiquitylation Complex by O2-Regulated Prolyl Hydroxylation," Science (2001) 292:464-468.

Jia, Steve, et al., "A Fully Active Catalytic Domain of Bovine Aspartyl (Asparaginyl) (β-Hydroxylase Expressed in *Escherichia coli*: Characterization and Evidence for the Identification of an Active-Site Region in Vertebrate α-Ketoglutarate-Dependent Dioxygenases," Proc. Natl. Acad. Sci. (1994) 91:7227-7231.

Jiang, Bing-Hua, et al., "Dimerization, DNA-Binding, and Transactivation Properties of Hypoxia-Inducible Factor 1α," J Biol. Chem. (1996) 271(30):17771-17778.

Jiang, Bing-Hua, et al., "Transactivation and Inhibitory Domains of Hypoxia-Inducible Factor 1α," J Biol. Chem. (1997) 272(31):19253-19260.

Jin, Kun Lin, et al., "Vascular Endothelial Growth Factor: Direct Neuroprotective Effect in in Vitro Ischemia," PNAS (2000) 97(18):10242-10247.

Kaule, Gunhild and Günzler, Volkmar, "Assay for 2-Oxoglutarate Decarboxylating Enzymes Based on the Determination of [1-14C] Succinate: Application to Prolyl 4-Hydroxylase," Analytical Biochem. (1990) 184:291-297.

Kietzmann, T., "Perivenous Expression of the mRNA of the Three Hypoxia-Inducible Factor Alpha Subunits, HIF-1α, HIF-2α and HIF-3α, in Rat Liver," NCBI Sequence Viewer (2001) Genbank Accession No. CAA70701.

Kietzmann, T., "Perivenous Expression of the mRNA of the Three Hypoxia-Inducible Factor Alpha Subunits, HIF-1α, HIF-2α and HIF-3α, in Rat Liver," NCBI Sequence Viewer (2001) Genbank Accession No. CAB96611.

Kietzmann, T., "Perivenous Expression of the mRNA of the Three Hypoxia-Inducible Factor Alpha Subunits, HIF-1α, HIF-2α and HIF-3α, in Rat Liver," NCBI Sequence Viewer (2001) Genbank Accession No. CAB96612.

Kietzmann, T., "Cloning and Expression of the *Xenopus laevis* Hypoxia-Inducible Factor 1 Alpha Homologue," NCBI Sequence Viewer (2000) Genbank Accession No. CAB96628.

Kivirikko, Kari I and Myllyharju, Johanna, "Prolyl 4-Hydroxylases and Their Protein Disulfide Isomerase Subunit," Matrix Biol. (1998) 16:357-368.

Kuntscher, M.V., et al., "The Role of Pre-Ischaemic Application of the Nitric Oxide Donor Spermine/Nitric Oxide Complex in Enhancing Flap Survival in a Rat Model," British J Plastic Surg. (2002) 55:430-433.

Lamerdin, J.E., et al., "Sequence Analysis of a 1.9mb Region in 19q13.2 Between APOE and D19S412," NCBI Sequence Viewer (1999) Genbank Accession No. AAD22668.

Lando, David, et al., "FIH-1 is an Asparaginyl Hydroxylase Enzyme That Regulates the Transcriptional Activity of Hypoxia-Inducible Factor," Genes Dev. (2002) 16:1466-1471.

Lando, David, et al., "Asapragine Hydroxylation of the HIF Transactivation Domain: A Hypoxic Switch," Science (2002) 295:858-861.

Larcher, Fernando, et al., "VEGF/VPF Overexpression in Skin of Transgenic Mice Induces Angiogenesis, Vascular Hyperpermeability and Accelerated Tumor Development," Oncogene (1998) 17:303-311.

Lee, Sang H., et al., "Early Expression of Angiogenesis Factors in Acute Myocardial Ischemia and Infarction," New Engl. J Med. (2000) 342(9):626-633.

Li, H., et al, "Induction of Phosphoglycerate Kinase 1 Gene Expression by Hypoxia: Roles of Arnt and HIF-1α," NCBI Sequence Viewer (2001) Genbank Accession No. Q61221.

Mahon, Patrick C., et al., "FIH-1: A Novel Protein That Interacts With HIF-1α and VHL to Mediate Repression of HIF-1 Transcriptional Activity," Genes Dev. (2001) 15:2675-2686.

Mahon, P. C., and Semenza, G.L., NCBI Sequence Viewer (2001) Genbank Accession No. AAL27308.

Majamaa, Kari, et al., "The 2-Oxoglutarate Binding Site of Prolyl 4-Hydroxylase," Euro. J Biochem. (1984) 138:239-245.

Majamaa, Kari, et al., "Differences Between Collagen Hydroxylases and 2-Oxoglutarate Dehydrogenase in Their Inhibition by Structural Analogues of 2-Oxoglutarate," Biochem. J (1985) 229:127-133.

Marcus, Jeffrey R., et al., "Cellular Mechanisms for Diminished Scarring With Aging," Plastic & Resconstructive Surg. (2000) 105(5):1591-1599.

Maxwell, Patrick H., et al, "The Tumour Suppressor Protein VHL Targets Hypoxia-Inducible Factors for Oxygen-Dependent Proteolysis," Nature (1999) 399:271-275.

Morio, Lisa A., et al., "Distinct Roles of Tumor Necrosis Factor-α and Nitric Oxide in Acute Liver Injury Induced by Carbon Tetrachloride in Mice," Toxicology & Applied Pharma. (2001) 172:44-51.

Morris, D.E., et al., "Acute and Chronic Animal Models for Excessive Dermal Scarring: Quantitative Studies," Plastic & Resconstructive Surg. (1997) 100(3):674-681.

Myllyharju, Johanna and Kivirikko, Kari I., "Characterization of the Iron- and 2-Oxoglutarate-Binding Sites of Human Prolyl 4-Hydroxylase," EMBO J (1997) 16(6):1173-1180.

Nambu, J.R., et al., "The *Drosophila melanogaster* Similar bHLH-PAS Gene Encodes a Protein Related to Human Hypoxia-Inducible Factor 1α and *Drosophila* Single-Minded," NCBI Sequence Viewer (2000) Genbank Accession No. JC4851.

Nanji, Amin A., et al., "Alterations in Glucose Transporter Proteins in Alcoholic Liver Disease in the Rat," Am. J Pathology (1995) 146(2).

Nemoto, Takahashi, et al., "Recombinant Erythropoietin Rapidly Treats Anemia in Ischemic Acute Renal Failure," Kidney Int. (2001) 59:246-251.

Nwogu, John I., et al., "Inhibition of Collagen Synthesis With Prolyl 4-Hydroxylase Inhibitor Improves Left Ventricle Function and Alters the Pattern of Left Ventricular Dilitation After Myocardial Infarction," Circulation (2001).

Richard, Darren E., et al., "Nonhypoxic Pathway Mediates the Induction of Hypoxia-Inducible Factor 1α in Vascular Smooth Muscle Cells," J Biol. Chem (2000) 275(35)26765-26771.

Sandau, Katrina B., et al., "Induction of Hypoxia-Inducible Factor 1 by Nitric Oxide is Mediated via the PI 3K Pathway," Biochem. & Biophys. Res. Comm. (2000) 278:263-267.

Sato, Nobuhiro, et al., "Effect of Acute and Chronic Ethanol Consumption on Hepatic Tissue Oxygen Tension in Rats," Pharmacol. Biochem. & Behavior (1983) 18(1):443-447.

Seki, Teruya, et al., "1, 10 Phenanthrolines 120596t and 120597u," Chem Abstracts 81:536.

Semenza, Gregg L., et al., "Structural and Functional Analysis of Hypoxia-Inducible Factor 1," Kidney Int. (1997) 51:553-555.

Semenza, Gregg L., et al., "Hypoxia, HIF-1 and the Pathophysiology of Common Human Diseases," Adv. Exp. Med. Biol. (2000) 475-123-130.

Serracino-Inglott, Ferdinand, et al., "Adenosine Preconditioning Attenuates Hepatic Reperfusion Injury in the Rat by Preventing the Down-Regulation of Endothelial Nitric Oxide Synthase," BMC Gastrointerology (2002) 2:22-27.

Sharp, Frank R., et al., "Multiple Molecular Penumbras After Focal Cerebral Ischemia," J Cereb. Blood Flow & Metab. (2000) 20:1011-1032.

Siren, Anna-Leena, et al., "Erythropoietin Prevents Neuronal Apoptosis After Cerebral Ischemia and Metabolic Stress," PNAS (2001) 98(7):4044-4049.

Sodhi, Akrit, et al., "MAPK and Akt Act Cooperatively But Independently on Hypoxia-Inducible Factor 1α in rasV12 Upregulation of VEGF," Biochem. & Biophys. Res. Comm. (2001) 287:292-300.

Srinivas, Vickram, et al., "Characterization of an Oxygen/Redox-Dependent Degradation Domain of Hypoxia-Inducible Factor α (HIF-α) Proteins," Biochem. & Biophys. Res. Comm. (1999) 260:557-561.

Stroka, Deborah M., et al., "HIF-1 is Expressed in Normoxic Tissue and Displays an Organ-Specific Regulation Under Systemic Hypoxia," FASEB J (2001) 15:2445-2453.

Strubelt, O., "Alcohol Potentiation of Liver Injury," Fund. & Applied Toixology (1984) 4:144-151.

Sutter, Carrie H., et al., "Hypoxia-Inducible Factor 1α Protein Expression is Controlled by Oxygen-Regulated Ubiquitination That is Disrupted by Deletions and Missense Mutations," PNAS (2000) 97(9):4748-4753.

Tacchini, Lorenzo, et al., "Hepatocyte Growth Factor Signalling Stimulates Hypoxia-Inducible Factor 1 (HIF-1) Activity in HepG2 Hepatoma Cells," Carcinogenesis (2001) 22(9):1363-1371.

Takahashi, T. et al., "Cloning of Hypoxia-Inducible Factor 1α cDNA From Chick Embryonic Ventricular Myocytes," NCBI Sequence Viewer (2001), Genbank Accession No. BAA34234.

Tanimoto, Keiji, et al., "Mechanism of Regulation of the Hypoxia-Inducible Factor 1α by the von Hippel-Lindau Tumor Suppressor Protein," EMBO J (2000) 19:4298-4309.

Taylor, Martin S., "Characterization and Comparative Analysis of the EGLN Gene Family," Gene (2001) 275:125-132.

Taylor, M. S., NCBI Sequence Viewer (2001), Genbank Accession No. CAC42510.

Taylor, M. S., NCBI Sequence Viewer (2001), Genbank Accession No. CAC42511.

Taylor, M. S., NCBI Sequence Viewer (2001), Genbank Accession No. CAC42515.

Taylor, M. S., NCBI Sequence Viewer (2001), Genbank Accession No. CAC42517.

Taylor, M. S., NCBI Sequence Viewer (2002), Genbank Accession No. NP_060025.

Thornburg, Lora D., et al., "A Non-Heme Iron Protein With Heme Tendencies: An Investigation of the Substrate Specificity of Thymine Hydroxylase," Biochem. (1993) 32:14023-14033.

Thornton, Ruth D., et al., "Interleukin 1 Induces Hypoxia-Inducible Factor 1 in Human Gingival and Sunovial Fibroblasts," Biochem. J (2000) 350:307-312.

Thurston, G., et al., "Leakage-Resistant Blood Vessels in Mice Transgenically Overexpressing Angiopoietin-1," Science (1999) 286:2511-2514.

Tian, H., et al., NCBI Sequence Viewer (1997), Genbank Accession No. AAB41495.

Tian, H., et al., NCBI Sequence Viewer (1997), Genbank Accession No. AAB41496.

Wang, Guang L. and Semenza, Gregg L., "General Involvement of Hypoxia-Inducible Factor 1 in Transcriptional Response to Hypoxia," Proc. Natl. Acad. Sci. (1993) 90:4304-4308.

Wang, You-Ping, et al., "Lipopolysaccharide Triggers Late Preconditioning Against Myocardial Infarction via Inducible Nitric Oxide Synthase," Cardio. Res. (2002) 56:33-42.

Wang, et al., NCBI Sequence Viewer (2001), Genbank Accession No. Q16665.

Wax, S.D., et al., "Identification of a Novel Growth Factor-Responsive Gene in Vascular Smooth Muscle Cells," NCBI Sequence Viewer (1994), Genbank Accession No. AAA19321.

Zager, Richard A., et al., "Renal Cholesterol Accumulation: A Durable Response After Acute and Subacute Renal Insults," Am. J Path. (2001) 159(2):743-752.

Zhong, Hua, et al., "Overexpression of Hypoxia-Inducible Factor 1α in Common Human Cancers and Their Metastases," Cancer Res. (1999) 59:5830-5835.

A.

B.

Error Bars: between-sample std. error

A.

B.

A.

B.

SEQUENCE LISTING

<160> NUMBER OF SEQ ID NOS: 5

<210> SEQ ID NO 1
<211> LENGTH: 20
<212> TYPE: DNA
<213> ORGANISM: Mus musculus

<400> SEQUENCE: 1
gttgcaaggc gaggcagctt                                          20

<210> SEQ ID NO 2
<211> LENGTH: 21
<212> TYPE: DNA
<213> ORGANISM: Mus musculus

<400> SEQUENCE: 2
tgacgatgat ggcatggtgg t                                        21

```
<210> SEQ ID NO 3
<211> LENGTH: 22
<212> TYPE: DNA
<213> ORGANISM: Rattus norvegicus

<400> SEQUENCE: 3
taggcacggc gactaccatc ga                                              22

<210> SEQ ID NO 4
<211> LENGTH: 23
<212> TYPE: DNA
<213> ORGANISM: Rattus norvegicus

<400> SEQUENCE: 4
cggcggcttt ggtgactcta gat                                             23

<210> SEQ ID NO 5
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 5

Asp Leu Asp Leu Glu Ala Leu Ala Pro Tyr Ile Pro Ala Asp Asp Asp
1               5                   10                  15

Phe Gln Leu
```

STABILIZATION OF HYPOXIA INDUCIBLE FACTOR (HIF) ALPHA

This application is a continuation of U.S. application Ser. No. 11/494,978, filed 28 Jul. 2006, which is a continuation of U.S. application Ser. No. 10/313,551, filed 6 Dec. 2002, which claims the benefit of U.S. Provisional Application Ser. No. 60/337,082, filed on 6 Dec. 2001; U.S. Provisional Application Ser. No. 60/359,683, filed on 25 Feb. 2002; U.S. Provisional Application Ser. No. 60/349,659, filed on 16 Jan. 2002; and U.S. Provisional Application Ser. No. 60/386,488, filed on 5 Jun. 2002, each of which is incorporated by reference herein in its entirety.

FIELD OF THE INVENTION

The present invention relates to methods of stabilizing the alpha subunit of hypoxia inducible factor (HIF) and to compounds that can be used in these methods.

BACKGROUND OF THE INVENTION

An early response to tissue hypoxia is induction of hypoxia inducible factor (HIF), a basic helix-loop-helix (bHLH) PAS (Per/Arnt/Sim) transcriptional activator that mediates changes in gene expression in response to changes in cellular oxygen concentration. HIF is a heterodimer containing an oxygen-regulated alpha subunit (HIFα) and a constitutively expressed beta subunit (HIFβ), also known as aryl hydrocarbon receptor nuclear transporter (ARNT). In oxygenated (normoxic) cells, HIFα subunits are rapidly degraded by a mechanism that involves ubiquitination by the von Hippel-Lindau tumor suppressor (pVHL) E3 ligase complex. Under hypoxic conditions, HIFα is not degraded, and an active HIFα/β complex accumulates in the nucleus and activates the expression of several genes including glycolytic enzymes, glucose transporter (GLUT)-1, erythropoietin (EPO), and vascular endothelial growth factor (VEGF). (Jiang et al. (1996) J Biol Chem 271:17771-17778; Iliopoulus et al. (1996) Proc Natl Acad Sci USA 93:10595-10599; Maxwell et al. (1999) Nature 399:271-275; Sutter et al. (2000) Proc Natl Acad Sci USA 97:4748-4753; Cockman et al. (2000) J Biol Chem 275:25733-25741; and Tanimoto et al. (2000) EMBO J. 19:4298-4309.)

Levels of HIFα protein are elevated in most cells in response to hypoxia and HIFα is induced in vivo when animals are subjected to anemia or hypoxia. HIFα levels rise within a few hours after the onset of hypoxia and return to baseline under continued hypoxic conditions. HIF has been implicated in numerous cellular and developmental processes including cell proliferation, angiogenesis, and cell cycle arrest. HIFα has also been associated with myocardial acute ischemia and early infarction, pulmonary hypertension, and inflammation. Although HIFα has been associated with tumor growth and metastasis, there is little indication that HIF is directly involved in tumorigenesis. Hypoxic preconditioning, in which a target organ is subjected to brief periods of hypoxia, has been shown to protect both myocardium and brain against hypoxic-ischemic injury. HIFα stabilization is closely associated with ischemia and is induced by preconditioning. (Wang and Semenza (1993) Proc Natl Acad Sci USA 90:4304-4308; Stroka et al. (2001) FASEB J 15:2445-2453; Semenza et al. (1997) Kidney Int 51:553-555; Carmeliet et al. (1998) Nature 394:485-490; Zhong et al. (1999) Cancer Res 59:5830-5835; Lee et al. (2000) N Engl J Med 343:148-149; Sharp et al. (2000) J Cereb Blood Flow Metab 20:1011-1032; Semenza et al. (2000) Adv Exp Med Biol 475:123-130; Thornton et al. (2000) Biochem J 350:307-312; Deindl and Schaper (1998) Mol Cell Biochem 186:43-51; Bergeron et al. (2000) Ann Neurol 48:285-296.)

Several investigators have studied the mechanism of interaction between HIFα and pVHL. An oxygen-dependent degradation domain (ODD) within HIF-1α from residue 401 to 603 was originally identified as sufficient to confer oxygen-dependent instability to chimeric protein constructs. A domain containing a portion of the ODD, from residue 526 to 652, was found to be required for pVHL-dependent degradation. Further, mutation of $P_{564}YI$ to aspartic acids or mutation of $K_{532}$ to arginine within a region conserved among HIFα homologs (residue 556 to 574 in HIF-1α) rendered the full-length HIFα protein stable under normoxic conditions and resistant to pVHL-mediated degradation. (Huang et al. (1998) Proc Natl Acad Sci USA 95:7987-7992; and Tanimoto et al. (2000) EMBO J. 19:4298-4309.)

HIFα levels are increased by a number of factors that mimic hypoxia, including iron chelators such as desferrioxamine (DFO) and divalent metal salts such as $CoCl_2$. HIFα levels are increased by angiotensin II, thrombin, and platelet-derived growth factor under normoxic conditions using a mechanism involving reactive oxygen species. Reports have also suggested HIFα is regulated by phosphorylation through pathways involving nitric oxide-activated phosphotidylinositol 3'-kinase (PI3K), hepatocyte growth factor, or mitogen-activated protein kinase. Glycogen-synthase kinase, which is a downstream target of PI3K, directly phosphorylates the HIFα ODD domain. (Richard et al. (2000) J Biol Chem 275:26765-26771; Sandau et al. (2000) Biochem Biophys Res Commun 278:263-267; Tacchini et al. (2001) Carcinogenesis. 22:1363-1371; and Sodhi et al. (2001) Biochem Biophys Res Commun 287:292-300.)

Hypoxia, a state of reduced oxygen, can occur when the lungs are compromised or blood flow is reduced. Ischemia, reduction in blood flow, can be caused by the obstruction of an artery or vein by a blood clot (thrombus) or by any foreign circulating matter (embolus), or by a vascular disorder such as atherosclerosis. Reduction in blood flow can have a sudden onset and short duration (acute ischemia), or can have a slow onset with long duration or frequent recurrence (chronic ischemia). Acute ischemia is often associated with regional, irreversible tissue necrosis (an infarct), whereas chronic ischemia is usually associated with transient hypoxic tissue injury. If the decrease in perfusion is prolonged or severe, however, chronic ischemia can also be associated with an infarct. Infarctions commonly occur in the spleen, kidney, lungs, brain, and heart, producing disorders such as intestinal infarction, pulmonary infarction, ischemic stroke, and myocardial infarction.

Pathologic changes in ischemic disorders depend on the duration and severity of ischemia, and on the length of patient survival. Necrosis can be seen within the infarct in the first 24 hours, and an acute inflammatory response develops in the viable tissue adjacent to the infarct with leukocytes migrating into the area of dead tissue. Over succeeding days, there is a gradual breakdown and removal of cells within the infarct by phagocytosis, and replacement with a collagenous or glial scar.

Hypoperfusion or infarction in one organ often affects other organs. For example, ischemia of the lung, caused by, for example, a pulmonary embolism, not only affects the lung, but also puts the heart and other organs, such as the brain, under hypoxic stress. Myocardial infarction, which often involves coronary artery blockage due to thrombosis, arterial wall vasospasms, or viral infection of the heart, can lead to congestive heart failure and systemic hypotension.

Secondary complications such as global ischemic encephalopathy can develop if the cardiac arrest is prolonged with continued hypoperfusion. Cerebral ischemia, most commonly caused by vascular occlusion due to atherosclerosis, can range in severity from transient ischemic attacks (TIAs) to cerebral infarction or stroke. While the symptoms of TIAs are temporary and reversible, TIAs tend to recur and are often followed by a stroke.

Occlusive arterial disease includes coronary artery disease, which can lead to myocardial infarction, and peripheral arterial disease, which can affect the abdominal aorta, its major branches, and arteries of the legs. Peripheral arterial disease includes Buerger's disease, Raynaud's disease, and acrocyanosis. Although peripheral arterial disease is commonly caused by atherosclerosis, other major causes include, e.g., diabetes, etc. Complications associated with peripheral arterial disease include severe leg cramps, angina, abnormal heart rhythms, heart failure, heart attack, stroke, and kidney failure.

Ischemic and hypoxic disorders are a major cause of morbidity and mortality. Cardiovascular diseases cause at least 15 million deaths every year and are responsible for 30% of deaths worldwide. Among the various cardiovascular diseases, ischemic heart disease and cerebrovascular diseases cause approximately 17% of deaths. Annually, 1.3 million cases of nonfatal acute myocardial infarction are reported, making the prevalence approximately 600 per 100,000 people. Further, an estimated five million Americans suffer from venous thrombosis every year, and approximately 600,000 of these cases result in pulmonary embolism. About one-third of the pulmonary embolisms end in death, making pulmonary embolism the third most common cause of death in the United States.

Currently, treatment of ischemic and hypoxic disorders is focused on relief of symptoms and treatment of causative disorders. For example, treatments for myocardial infarction include nitroglycerin and analgesics to control pain and relieve the workload of the heart. Other medications, including digoxin, diuretics, amrinone, β-blockers, lipid-lowering agents and angiotensin-converting enzyme inhibitors, are used to stabilize the condition, but none of these therapies directly address the tissue damage produced by the ischemia and hypoxia.

Due to deficiencies in current treatments, there remains a need for methods that are effective in treating conditions involving ischemia and hypoxia such as occlusive arterial disease, angina pectoris, intestinal infarctions, pulmonary infarctions, cerebral ischemia, and myocardial infarction. There is also a need for methods that are effective in the prevention of tissue damage caused by ischemia that occurs due to, e.g., atherosclerosis, diabetes, and pulmonary disorders such as pulmonary embolism and the like. In summary, there is a need in the art for methods and compounds that can be used to stabilize HIF, and to treat and prevent HIF-associated disorders including conditions involving ischemia and hypoxia.

SUMMARY OF THE INVENTION

Described herein are methods of stabilizing the alpha subunit of hypoxia inducible factor (HIFα). These methods can be applied in vivo or in vitro.

The present invention relates generally to methods of stabilizing the alpha subunit of hypoxia inducible factor (HIF). In one embodiment, the method of stabilizing the alpha subunit of HIF (HIFα) comprises administering to a subject a compound that inhibits hydroxylation of HIFα. In certain of the embodiments of the present invention, the HIFα is selected from the group consisting of HIF-1α, HIF-2α, HIF-3α, and any fragment thereof. In a further embodiment, the method comprises administering to a subject a compound that inhibits 2-oxoglutarate dioxygenase enzyme activity. In various embodiments, the 2-oxoglutarate dioxygenase enzyme is selected from the group consisting of EGLN1, EGLN2, EGLN3, procollagen prolyl 4-hydroxylase, procollagen prolyl 3-hydroxylase, procollagen lysyl hydroxylase, PHD4, FIH-1, and any subunit or fragment thereof, respectively.

In particular methods for stabilizing HIFα according to the present invention, the methods comprise inhibiting HIF prolyl hydroxylase enzyme activity. In further embodiments, the HIF prolyl hydroxylase enzyme is selected from the group consisting of EGLN1, EGLN2, EGLN3, and any subunit or fragment thereof, respectively.

The present invention provides, in one aspect, methods for stabilizing endogenous HIFα. Thus, in a particular embodiment, the HIFα is endogenous to the subject. Embodiments of the present invention include methods for stabilizing HIFα in which a compound that stabilizes HIFα is administered to a subject in vivo. The subject can be, for example, an animal, preferably, a mammal, and, more preferably, a human. Methods of ex vivo administration are also contemplated. In such methods, the subject can be, e.g., a cell, tissue, or organ, etc. In certain embodiments, the subject is a cell, tissue, or organ derived from a system such as the renal, cardiac, hepatic, pulmonary, hematopoietic, gastrointestinal, neuronal, or musculoskeletal system, etc.

Methods for treating, preventing, or pretreating a HIF-associated condition are also provided. In particular, the present invention provides a method for treating, preventing, or pretreating a HIF-associated condition, the method comprising stabilizing HIFα. In specific aspects, the invention provide a method for treatment, prevention, or pretreatment/preconditioning of a HIF-associated condition in a subject, the method comprising stabilization of HIFα. In various aspects, the HIF-associated condition is associated with ischemia or hypoxia. In a preferred aspect, the method comprises administering to the subject a compound that stabilizes HIFα.

In various embodiments, the compound is selected from the group consisting of heterocyclic carboxamides, phenanthrolines, hydroxamates, and physiologically active salts and prodrugs derived therefrom. In particular embodiments, the compound is a heterocyclic carboxamide selected from the group consisting of pyridine carboxamides, quinoline carboxamides, isoquinoline carboxamides, cinnoline carboxamides, and beta-carboline carboxamides. In a preferred embodiment of the present invention, the compound is delivered in an oral formulation. In another preferred embodiment, the compound is delivered in a transdermal formulation.

In one method of stabilizing HIFα according to the present invention, the compound stabilizes HIFα by specifically inhibiting hydroxylation of at least one amino acid residue in HIFα. In a further aspect, the amino acid residue is selected from the group consisting of proline and asparagine.

Methods for treating, preventing, or pretreating a HIF-associated condition in a subject, the methods comprising inhibiting 2-oxoglutarate dioxygenase enzyme activity, are also provided, and include methods in which the HIF-associated condition is one associated with ischemia or hypoxia. In one aspect, the present invention provides a method for treating, preventing, or pretreating a HIF-associated condition, the method comprising administering to the subject a compound that inhibits 2-oxoglutarate dioxygenase enzyme activity.

In a preferred embodiment, the present invention provides a method of treating, preventing, or pretreating a HIF-associated condition in a subject, the method comprising inhibiting HIF prolyl hydroxylase enzyme activity. Again, HIF-associated conditions include those associated with hypoxia, or with ischemia, etc. In a particular embodiment, the method comprises administering to the subject a compound that inhibits HIF prolyl hydroxylase activity.

In a further embodiment, the method further comprises administering a second compound. In particular embodiments, the second compound inhibits 2-oxoglutarate dioxygenase enzyme activity, or the compound and the second compound inhibit the activities of different 2-oxoglutarate dioxygenase enzymes, or the second compound is selected from the group consisting of an ACE inhibitor (ACEI), angiotensin-II receptor blocker (ARB), diuretic, digoxin, statin, or carnitine, etc.

In specific embodiments, HIF-associated conditions include disorders such as pulmonary disorders, e.g., pulmonary embolism, etc., cardiac disorders, e.g., myocardial infarction, congestive heart failure, etc., neurological disorders, and the like. The present invention thus clearly contemplates methods that can be applied to the treatment, prevention, or pretreatment/preconditioning of a HIF-associated condition associated with any ischemic event, whether acute or transient, or chronic. Acute ischemic events can include those associated with surgery, organ transplantation, infarction (e.g., cerebral, intestinal, myocardial, pulmonary, etc.), trauma, insult, or injury, etc. Chronic events associated with ischemia can include hypertension, diabetes, occlusive arterial disease, chronic venous insufficiency, Raynaud's disease, cirrhosis, congestive heart failure, systemic sclerosis, etc.

Methods of preconditioning or pretreating are specifically contemplated. In one embodiment, the invention provides methods of pretreating or preconditioning wherein HIFα is stabilized prior to the occurrence of an event associated with a HIF-associated condition, e.g., ischemia, etc., or the development of a HIF-associated condition. Ischemias can be induced by acute events. Such events can include, for example, surgery, e.g., angioplasty, organ transplantation, etc., and related procedures such as administration of anesthesia, etc. Furthermore, chronic events specific embodiments, the methods of pretreating or preconditioning are applied in situations where a subject has a disorder predictive of the development of a HIF-associated condition, e.g., transient ischemic attack or angina pectoris, indicative of stroke and myocardial infarction, respectively, in order to prevent the development of or reduce the degree of development of the HIF-associated condition. In a particular embodiment, a compound that stabilizes HIFα is administered to a subject in order to increase preconditioning factors for ischemia, for example, EPO, etc.

Methods for increasing expression of various HIF-related factors are specifically contemplated herein. In one aspect, the present invention provides a method for increasing expression of angiogenic factors in a subject, the method comprising stabilizing HIFα. In another aspect, the present invention provides a method of increasing expression of glycolytic factors in a subject, the method comprising stabilizing HIFα. In a further aspect, the invention provides a method of increasing expression of factors associated with oxidative stress in a subject, the method comprising stabilizing HIFα. A method of treating a subject having a disorder associated with ischemic reperfusion injury, the method comprising stabilizing HIFα, is also contemplated.

Methods for identifying compounds that stabilize HIFα are also provided herein. For example, the present invention provides a method of identifying a compound that stabilizes HIFα, the method comprising: (a) administering a compound of interest to a subject or to a sample from a subject; (b) measuring the HIFα level in the subject or in the sample; and (c) comparing the HIFα level in the subject or in the sample to a standard level, wherein an increase in the HIFα level in the subject or the sample is indicative of a compound that stabilizes HIFα.

In another aspect, the methods of the invention are used to prevent the tissue damage caused by HIF-associated disorders including, but not limited to, ischemic and hypoxic disorders. In one embodiment, treatment is predicated on predisposing conditions, e.g., hypertension, diabetes, occlusive arterial disease, chronic venous insufficiency, Raynaud's disease, cirrhosis, congestive heart failure, and systemic sclerosis.

In yet another aspect, the methods of the invention can be used as a pretreatment to decrease or prevent the tissue damage caused by HIF-associated disorders including, but not limited to, ischemic and hypoxic disorders. In one embodiment, the need for pretreatment is based on a patient's history of recurring episodes of an ischemic condition, e.g., myocardial infarction or transient ischemic attacks, or has symptoms of impending ischemia, e.g., angina pectoris, etc. In another embodiment, the need for pretreatment is based on physical parameters implicating possible or likely ischemia or hypoxia, such as is the case with, e.g., individuals placed under general anesthesia or temporarily working at high altitudes. In yet another embodiment, the methods may be used in the context of organ transplants to pretreat organ donors and to maintain organs removed from the body prior to implantation in a recipient.

In another aspect, the invention provides compounds that stabilize HIFα and methods of using the compounds to prevent, pretreat, or treat HIF-associated conditions such as those described above. In one embodiment, a therapeutically effective amount of the compound or a pharmaceutically acceptable salt thereof, alone or in combination with a pharmaceutically acceptable excipient, is administered to a subject having a HIF-associated condition. In one specific embodiment, the compound is administered immediately following the diagnosis of an acute ischemic disorder. In another specific embodiment, the compound is administered to a subject during the course of a chronic ischemic condition. In yet another specific embodiment, the ischemia is due to a transient or acute trauma, insult, or injury such as, e.g., a spinal cord injury. In a specific embodiment, the compound is administered to a patient in need following diagnosis of a pulmonary disorder such as COPD and the like.

In one aspect, the compound can be administered based on predisposing conditions, e.g., chronic conditions, or as a pretreatment to decrease or prevent tissue damage caused by HIF-associated disorders. In a specific aspect, the compound is administered to a subject who has a history of recurring episodes of an ischemic condition, e.g., myocardial infarction or transient ischemic attacks, or has symptoms of impending ischemia, e.g., angina pectoris. In another specific embodiment, the compound is administered based on physical parameters implicating possible ischemia or hypoxia, such as is the case with, e.g., individuals placed under general anesthesia or temporarily working at high altitudes. In yet another embodiment, the compounds may be used in the context of organ transplants to pretreat organ donors and to maintain organs removed from the body prior to implantation in a recipient.

In one aspect, a compound of the present invention stabilizes HIFα by specifically inhibiting hydroxylation of amino acid residues in the HIFα protein. In one embodiment, the agent inhibits hydroxylation of HIFα proline residues. In one specific embodiment, the agent inhibits hydroxylation of the HIF-1α $P_{564}$ residue or a homologous proline in another HIFα isoform. In another specific embodiment, the agent inhibits hydroxylation of the HIF-1α $P_{402}$ residue or a homologous proline in another HIFα isoform. In yet another embodiment, the compound may additionally inhibit hydroxylation of HIFα asparagine residues. In one specific embodiment, the agent inhibits hydroxylation of the HIF-1α $N_{803}$ residue or a homologous asparagine residue in another HIFα isoform.

In certain embodiments, compounds used in the methods of the invention are selected from a compound of the formula (I)

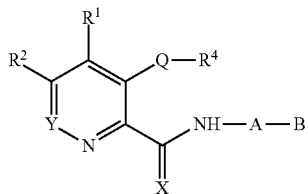

(I)

wherein

A is 1,2-arylidene, 1,3-arylidene, 1,4-arylidene; or $(C_1-C_4)$-alkylene, optionally substituted by one or two halogen, cyano, nitro, trifluoromethyl, $(C_1-C_6)$-alkyl, $(C_1-C_6)$-hydroxyalkyl, $(C_1-C_6)$-alkoxy, —O—$[CH_2]_x$—$C_fH_{(2f+1-g)}$Hal$_g$, $(C_1-C_6)$-fluoroalkoxy, $(C_1-C_8)$-fluoroalkenyloxy, $(C_1-C_8)$-fluoroalkynyloxy, —OCF$_2$Cl, —O—CF$_2$—CHFCl; $(C_1-C_6)$-alkylmercapto, $(C_1-C_6)$-alkylsulfinyl, $(C_1-C_6)$-alkylsulfonyl, $(C_1-C_6)$-alkylcarbonyl, $(C_1-C_6)$-alkoxycarbonyl, carbamoyl, N—$(C_1-C_4)$-alkylcarbamoyl, N,N-di-$(C_1-C_4)$-alkylcarbamoyl, $(C_1-C_6)$-alkylcarbonyloxy, $(C_3-C_8)$-cycloalkyl, phenyl, benzyl, phenoxy, benzyloxy, anilino, N-methylanilino, phenylmercapto, phenylsulfonyl, phenylsulfinyl, sulfamoyl, N—$(C_1-C_4)$-alkylsulfamoyl, N,N-di-$(C_1-C_4)$-allylsulfamoyl; or by a substituted $(C_6-C_{12})$-aryloxy, $(C_7-C_{11})$-aralkyloxy, $(C_6-C_{12})$-aryl, $(C_7-C_{11})$-aralkyl radical, which carries in the aryl moiety one to five identical or different substituents selected from halogen, cyano, nitro, trifluoromethyl, $(C_1-C_6)$-alkyl, $(C_1-C_6)$-alkoxy, —O—$[CH_2]_x$—$C_fH_{2f+1-g}$Hal$_g$, —OCF$_2$Cl, —O—CF$_2$—CHFCl, $(C_1-C_6)$-allylmercapto, $(C_1-C_6)$-alkylsulfinyl, $(C_1-C_6)$-alkylsulfonyl, $(C_1-C_6)$-alkylcarbonyl, $(C_1-C_6)$-alkoxycarbonyl, carbamoyl, N—$(C_1-C_4)$-alkylcarbamoyl, N,N-di-$(C_1-C_4)$-alkylcarbamoyl, $(C_1-C_6)$-alkylcarbonyloxy, $(C_3-C_8)$-cycloalkyl, sulfamoyl, N—$(C_1-C_4)$-alkylsulfamoyl, N,N-di-$(C_1-C_4)$-alkylsulfamoyl; or wherein A is —CR$^5$R$^6$ and R$^5$ and R$^6$ are each independently selected from hydrogen, $(C_1-C_6)$-alkyl, $(C_3-C_7)$-cycloalkyl, aryl, or a substituent of the α-carbon atom of an α-amino acid, wherein the amino acid is a natural L-amino acid or its D-isomer.

B is —CO$_2$H, —NH$_2$, —NHSO$_2$CF$_3$, tetrazolyl, imidazolyl, 3-hydroxyisoxazolyl, —CONHCOR''', —CONHSOR''', CONHSO$_2$R''', where R''' is aryl, heteroaryl, $(C_3-C_7)$-cycloalkyl, or $(C_1-C_4)$-alkyl, optionally monosubstituted by $(C_6-C_{12})$-aryl, heteroaryl, OH, SH, $(C_1-C_4)$-alkyl, $(C_1-C_4)$-alkoxy, $(C_1-C_4)$-thioallyl, $(C_1-C_4)$-sulfinyl, $(C_1-C_4)$-sulfonyl, CF$_3$, Cl, Br, F, I, NO2, —COOH, $(C_2-C_5)$-alkoxycarbonyl, NH$_2$, mono-$(C_1-C_4$-alkyl)-amino, di-$(C_1-C_4$-alkyl)-amino, or $(C_1-C_4)$-perfluoroalkyl; or wherein B is a CO$_2$-G carboxyl radical, where G is a radical of an alcohol G-OH in which G is selected from $(C_1-C_{20})$-alkyl radical, $(C_3-C_8)$-cycloalkyl radical, $(C_2-C_{20})$-alkenyl radical, $(C_3-C_8)$-cycloalkenyl radical, retinyl radical, $(C_2-C_{20})$-alkynyl radical, $(C_4-C_{20})$-alkenynyl radical, where the alkenyl, cycloalkenyl, alkynyl, and alkenynyl radicals contain one or more multiple bonds; $(C_6-C_{16})$-carbocyclic aryl radical, $(C_7-C_{16})$-carbocyclic aralkyl radical, heteroaryl radical, or heteroaralkyl radical, wherein a heteroaryl radical or heteroaryl moiety of a heteroalkyl radical contains 5 or 6 ring atoms; and wherein radicals defined for G are substituted by one or more hydroxyl, halogen, cyano, trifluoromethyl, nitro, carboxyl, $(C_1-C_{12})$-alkyl, $(C_3-C_8)$-cycloalkyl, $(C_5-C_8)$-cycloalkenyl, $(C_6-C_{12})$-aryl, $(C_7-C_{16})$-aralkyl, $(C_2-C_{12})$-alkenyl, $(C_2-C_{12})$-alkynyl, $(C_1-C_{12})$-alkoxy, $(C_1-C_{12})$-alkoxy-$(C_1-C_{12})$-alkyl, $(C_1-C_{12})$-alkoxy-$(C_1-C_{12})$-alkoxy, $(C_6-C_{12})$-aryloxy, $(C_7-C_{16})$-aralkyloxy, $(C_1-C_8)$-hydroxyalkyl, —O—$[CH_2]_x$—$C_fH_{(2f+1-g)}$—F$_g$, —OCF$_2$Cl, —OCF$_2$—CHFCl, $(C_1-C_{12})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_2-C_{12})$-alkenylcarbonyl, $(C_2-C_{12})$-alkynylcarbonyl, $(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_2-C_{12})$-alkenyloxycarbonyl, $(C_2-C_{12})$-alkynyloxycarbonyl, acyloxy, $(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$ aralkyloxycarbonyloxy, $(C_3-C_8)$-cycloalkoxycarbonyloxy, $(C_2-C_{12})$-alkenyloxycarbonyloxy, $(C_2-C_{12})$-alkynyloxycarbonyloxy, carbamoyl, N—$(C_1-C_{12})$-alkylcarbamoyl, N,N-di$(C_1-C_{12})$-alkylcarbamoyl, N—$(C_3-C_8)$-cycloalkyl-carbamoyl, N—$(C_6-C_{16})$-arylcarbamoyl, N—$(C_7-C_{16})$-aralkylcarbamoyl, N—$(C_1-C_{10})$-alkyl-N—$(C_6-C_{16})$-arylcarbamoyl, N—$(C_1-C_{10})$-alkyl-N—$(C_7-C_{16})$-aralkylcarbamoyl, N—$((C_1-C_{10})$-alkoxy-$(C_1-C_{10})$-alkyl)-carbamoyl, N—$((C_6-C_{12})$-aryloxy-$(C_1-C_{10})$alkyl)-carbamoyl, N—$((C_7-C_{16})$-aralkyloxy-$(C_1-C_{10})$-alkyl)-carbamoyl, N—$(C_1-C_{10})$-alkyl-N—$((C_1-C_{10})$-alkoxy-$(C_1-C_{10})$-alkyl)-carbamoyl, N—$(C_1-C_{10})$-alkyl-N—$((C_6-C_{16})$-aryloxy-$(C_1-C_{10})$-alkyl)-carbamoyl, N—$(C_1-C_{10})$-alkyl-N—$((C_7-C_{16})$-aralkyloxy-$(C_1-C_{10})$-alkyl)-carbamoyl, carbamoyloxy, N—$(C_1-C_{12})$-alkylcarbamoyloxy, N,N-di-$(C_1-C_{12})$-alkylcarbamoyloxy, N—$(C_3-C_8)$-cycloalkylcarbamoyloxy, N—$(C_6-C_{12})$-arylcarbamoyloxy, N—$(C_7-C_{16})$-aralkylcarbamoyloxy, N—$(C_1-C_{10})$-alkyl-N—$(C_6-C_{12})$-arylcarbamoyloxy, N$(C_1-C_{10})$-alkyl-N—$(C_7-C_{16})$-aralkylcarbamoyloxy, N—$((C_1-C_{10})$-alkyl)-carbamoyloxy, N—$((C_6-C_{12})$-aryloxy-$(C_1-C_{10})$-alkyl)-carbamoyloxy, N—$((C_7-C_{16})$-aralkyloxy-$(C_1-C_{10})$-alkyl)-carbamoyloxy, N—$(C_1-C_{10})$-alkyl-N—$((C_1-C_{10})$-alkoxy-$(C_1-C_{10})$-alkyl)-carbamoyloxy, N—$(C_1-C_{10})$-alkyl-N—$((C_6-C_{12})$-aryloxy-$(C_1-C_{10})$-alkyl)-carbamoyloxy, N—$(C_1-C_{10})$-alkyl-N—$((C_7-C_{16})$-aralkyloxy-$(C_1-C_{10})$-alkyl)-carbamoyloxy, amino, $(C_1-C_{12})$-alkylamino, di-$(C_1-C_{12})$-alkylamino, $(C_3-C_8)$-cycloalkylamino, $(C_2-C_{12})$-alkenylamino, $(C_2-C_{12})$-alkynylamino, N—$(C_6-C_{12})$-arylamino, N—$(C_7-C_{11})$-aralkylamino, N-alkyl-aralkylamino, N-alkyl-arylamino, $(C_1-C_{12})$-alkoxyamino, $(C_1-C_{12})$-alkoxy-N—$(C_1-C_{10})$-alkylamino, $(C_1-C_{12})$-alkylcarbonylamino, $(C_3-C_8)$-cycloalkylcarbonylamino, $(C_6-C_{12})$ arylcarbonylamino, $(C_7-C_{16})$-aralkylcarbonylamino, $(C_1-C_{12})$-alkylcarbonyl-N—$(C_1-C_{10})$-alkylamino, $(C_3-C_8)$-cycloalkylcarbonyl-N—$(C_1-C_{10})$-alkylamino, $(C_6-C_{12})$-arylcarbonyl-N—$(C_1-C_{10})$alkylamino, $(C_7-C_{11})$-aralkylcarbonyl-N—$(C_1-C_{10})$-alkylamino, $(C_1-C_{12})$-alkylcarbonylamino-$(C_1-C_8)$-alkyl, $(C_3-C_8)$-cycloalkylcarbonylamino-$(C_1-C_8)$alkyl, $(C_6-C_{12})$-arylcarbonylamino-$(C_1-C_8)$-alkyl, $(C_7-C_{12})$-aralkylcarbonylamino$(C_1-C_8)$-alkyl, amino-$(C_1-C_{10})$-alkyl, N—$(C_1-C_{10})$ alkylamino-$(C_1-C_{10})$-alkyl, N,N-di-$(C_1-C_{10})$-alkylamino-$(C_1-C_{10})$-alkyl, $(C_3-C_8)$cycloalkylamino-$(C_1-$ $C_{10}$)-alkyl, $(C_1$-$C_{12})$-alkylmercapto, $(C_1$-$C_{12})$-alkylsulfinyl, $(C_1$-$C_{12})$-alkylsulfonyl, $(C_6$-$C_{16})$-arylmercapto, $(C_6$-$C_{16})$-arylsulfinyl, $(C_6$-$C_{12})$-arylsulfonyl, $(C_7$-$C_{16})$-aralkylmercapto, $(C_7$-$C_{16})$-aralkylsulfinyl, $(C_7$-$C_{16})$-aralkylsulfonyl, sulfamoyl, N—$(C_1$-$C_{10})$-alkylsulfamoyl, N,N-di$(C_1$-$C_{10})$-alkylsulfamoyl, $(C_3$-$C_8)$-cycloalkylsulfamoyl, N—$(C_6$-$C_{12})$-alkylsulfamoyl, N—$(C_7$-$C_{16})$-aralkylsulfamoyl, N—$(C_1$-$C_{10})$-alkyl-N—$(C_6$-$C_{12})$-arylsulfamoyl, N—$(C_1$-$C_{10})$-alkyl-N—$(C_7$-$C_{16})$-aralkylsulfamoyl, $(C_1$-$C_{10})$-alkylsulfonamido, N—$((C_1$-$C_{10})$-alkyl)-$(C_1$-$C_{10})$-alkylsulfonamido, $(C_7$-$C_{16})$-aralkylsulfonamido, or N—$((C_1$-$C_{10})$-alkyl-$(C_7$-$C_{16})$-aralkylsulfonamido; wherein radicals which are aryl or contain an aryl moiety, may be substituted on the aryl by one to five identical or different hydroxyl, halogen, cyano, trifluoromethyl, nitro, carboxyl, $(C_1$-$C_{12})$-alkyl, $(C_3$-$C_8)$-cycloalkyl, $(C_6$-$C_{12})$-aryl, $(C_7$-$C_{16})$-aralkyl, $(C_1$-$C_{12})$-alkoxy, $(C_1$-$C_{12})$-alkoxy-$(C_1$-$C_{12})$alkyl, $(C_1$-$C_{12})$-alkoxy-$(C_1$-$C_{12})$ alkoxy, $(C_6$-$C_{12})$-aryloxy, $(C_7$-$C_{16})$-aralkyloxy, $(C_1$-$C_8)$-hydroxyalkyl, $(C_1$-$C_{12})$-alkylcarbonyl, $(C_3$-$C_8)$-cycloalkylcarbonyl, $(C_6$-$C_{12})$-arylcarbonyl, $(C_7$-$C_{16})$ aralkylcarbonyl, $(C_1$-$C_{12})$-alkoxycarbonyl, $(C_1$-$C_{12})$-alkoxy-$(C_1$-$C_{12})$-alkoxycarbonyl, $(C_6$-$C_{12})$-aryloxycarbonyl, $(C_7$-$C_{16})$-aralkoxycarbonyl, $(C_3$-$C_8)$-cycloalkoxycarbonyl, $(C_2$-$C_{12})$-alkenyloxycarbonyl, $(C_2$-$C_{12})$-alkynyloxycarbonyl, $(C_1$-$C_{12})$-alkylcarbonyloxy, $(C_3$-$C_8)$-cycloalkylcarbonyloxy, $(C_6$-$C_{12})$-arylcarbonyloxy, $(C_7$-$C_{16})$-aralkylcarbonyloxy, cinnamoyloxy, $(C_2$-$C_{12})$-alkenylcarbonyloxy, $(C_2$-$C_{12})$-alkynylcarbonyloxy, $(C_1$-$C_{12})$-alkoxycarbonyloxy, $(C_1$-$C_{12})$-alkoxy-$(C_1$-$C_{12})$-alkoxycarbonyloxy, $(C_6$-$C_{12})$-aryloxycarbonyloxy, $(C_7$-$C_{16})$-aralkyloxycarbonyloxy, $(C_3$-$C_8)$-cycloalkoxycarbonyloxy, $(C_2$-$C_{12})$-alkenyloxycarbonyloxy, $(C_2$-$C_{12})$-alkynyloxycarbonyloxy, carbamoyl, N—$(C_1$-$C_{12})$-alkylcarbamoyl, N,N-di-$(C_1$-$C_{12})$-alkylcarbamoyl, N—$(C_3$-$C_8)$-cycloalkylcarbamoyl, N—$(C_6$-$C_{12})$-arylcarbamoyl, N—$(C_7$-$C_{16})$-aralkylcarbamoyl, N—$(C_1$-$C_{10})$-alkyl-N—$(C_6$-$C_{12})$-arylcarbamoyl, N—$(C_1$-$C_{10})$-alkyl-N—$(C_7$-$C_{16})$-aralkylcarbamoyl, N—$((C_1$-$C_{10})$-alkoxy-$(C_1$-$C_{10})$-alkyl)-carbamoyl, N—$((C_6$-$C_{12})$-aryloxy-$(C_1$-$C_{10})$-alkyl)-carbamoyl, N—$((C_7$-$C_{16})$-aralkyloxy-$(C_1$-$C_{10})$-alkyl)-carbamoyl, N—$(C_1$-$C_{10})$-alkyl-N—$((C_1$-$C_{10})$-alkoxy-$(C_1$-$C_{10})$-alkyl)-carbamoyl, N—$(C_1$-$C_{10})$-alkyl-N—$((C_6$-$C_{12})$-aryloxy-$(C_1$-$C_{10})$-alkyl)-carbamoyl, N—$(C_1$-$C_{10})$-alkyl-N—$((C_7$-$C_{16})$-aralkyloxy-$(C_1$-$C_{10})$-alkyl)-carbamoyl, carbamoyloxy, N—$(C_1$-$C_{12})$-alkylcarbamoyloxy, N,N-di-$(C_1$-$C_{12})$-alkylcarbamoyloxy, N—$(C_3$-$C_8)$-cycloalkylcarbamoyloxy, N—$(C_6$-$C_{12})$-arylcarbamoyloxy, N—$(C_7$-$C_{16})$-aralkylcarbamoyloxy, N—$(C_1$-$C_{10})$-alkyl-N—$(C_6$-$C_{12})$-arylcarbamoyloxy, N$(C_1$-$C_{10})$-alkyl-N—$(C_7$-$C_{16})$-aralkylcarbamoyloxy, N—$((C_1$-$C_{10})$-alkyl)-carbamoyloxy, N—$((C_6$-$C_{12})$-aryloxy-$(C_1$-$C_{10})$-alkyl)-carbamoyloxy, N—$((C_7$-$C_{16})$-aralkyloxy-$(C_1$-$C_{10})$-alkyl)-carbamoyloxy, N—$(C_1$-$C_{10})$-alkyl-N—$((C_1$-$C_{10})$-alkoxy-$(C_1$-$C_{10})$-alkyl)-carbamoyloxy, N—$(C_1$-$C_{10})$-alkyl-N—$((C_6$-$C_{12})$-aryloxy-$(C_1$-$C_{10})$-alkyl)-carbamoyloxy, N—$(C_1$-$C_{10})$-alkyl-N—$((C_7$-$C_{16})$-aralkyloxy-$(C_1$-$C_{10})$-alkyl)-carbamoyloxy, amino, $(C_1$-$C_{12})$-alkylamino, di-$(C_1$-$C_{12})$-alkylamino, $(C_3$-$C_8)$-cycloalkylamino, $(C_3$-$C_{12})$-alkenylamino, $(C_3$-$C_{12})$-alkynylamino, N—$(C_6$-$C_{12})$-arylamino, N—$(C_7$-$C_{11})$-aralkylamino, N-alkylaralkylamino, N-alkyl-arylamino, $(C_1$-$C_{12})$-alkoxyamino, $(C_1$-$C_{12})$-alkoxy-N—$(C_1$-$C_{10})$-alkylamino, $(C_1$-$C_{12})$-alkylcarbonylamino, $(C_3$-$C_8)$-cycloalkylcarbonylamino, $(C_6$-$C_{12})$-arylcarbonylamino, $(C_7$-$C_{16})$-alkylcarbonylamino, $(C_1$-$C_{12})$-alkylcarbonyl-N—$(C_1$-$C_{10})$-alkylamino, $(C_3$-$C_8)$-cycloalkylcarbonyl-N—$(C_1$-$C_{10})$-alkylamino, $(C_6$-$C_{12})$-arylcarbonylamino-N—$(C_1$-$C_{10})$-alkylamino, $(C_7$-$C_{11})$-aralkylcarbonyl-N—$(C_1$-$C_{10})$-alkylamino, $(C_1$-$C_{12})$-alkylcarbonylamino-$(C_1$-$C_8)$-alkyl, $(C_3$-$C_8)$-cycloalkylcarbonylamino-$(C_1$-$C_8)$-alkyl, $(C_6$-$C_{12})$-arylcarbonylamino-$(C_1$-$C_8)$-alkyl, $(C_7$-$C_{16})$-aralkylcarbonylamino-$(C_1$-$C_8)$-alkyl, amino-$(C_1$-$C_{10})$-alkyl, N—$(C_1$-$C_{10})$-alkylamino-$(C_1$-$C_{10})$alkyl, N,N-di-$(C_1$-$C_{10})$-alkylamino-$(C_1$-$C_{10})$-alkyl, $(C_3$-$C_8)$-cycloalkylamino-$(C_1$-$C_{10})$-alkyl, $(C_1$-$C_{12})$-alkylmercapto, $(C_1$-$C_{12})$-alkylsulfinyl, $(C_1$-$C_{12})$-alkylsulfonyl, $(C_6$-$C_{12})$-arylmercapto, $(C_6$-$C_{12})$-arylsulfinyl, $(C_6$-$C_{12})$-arylsulfonyl, $(C_7$-$C_{16})$-aralkylmercapto, $(C_7$-$C_{16})$-aralkylsulfinyl, or $(C_7$-$C_{16})$-aralkylsulfonyl;

X is O or S;

Q is O, S, NR', or a bond;

where, if Q is a bond, $R^4$ is halogen, nitrile, or trifluoromethyl; or where, if Q is O, S, or NR', $R^4$ is hydrogen, $(C_1$-$C_{10})$-alkyl radical, $(C_2$-$C_{10})$-alkenyl radical, $(C_2$-$C_{10})$-alkynyl radical, wherein alkenyl or alkynyl radical contains one or two C—C multiple bonds; unsubstituted fluoroalkyl radical of the formula —$[CH_2]_x$—$C_fH_{(2f+1-g)}$—$F_g$, $(C_1$-$C_8)$-alkoxy-$(C_1$-$C_6)$-alkyl radical, $(C_1$-$C_6)$-alkoxy-$(C_1$-$C_4)$-alkoxy-$(C_1$-$C_4)$-alkyl radical, aryl radical, heteroaryl radical, $(C_7$-$C_{11})$-aralkyl radical, or a radical of the formula Z $$-[CH_2]_v-[O]_w-[CH_2]_t-E \qquad (Z)$$

where

E is a heteroaryl radical, a $(C_3$-$C_8)$-cycloalkyl radical, or a phenyl radical of the formula F

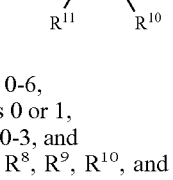

v is 0-6, w is 0 or 1, t is 0-3, and $R^7$, $R^8$, $R^9$, $R^{10}$, and $R^{11}$ are identical or different and are hydrogen, halogen, cyano, nitro, trifluoromethyl, $(C_1$-$C_6)$-alkyl, $(C_3$-$C_8)$-cycloalkyl, $(C_1$-$C_6)$-alkoxy, —O—$[CH_2]_x$—$C_fH_{(2f+1-g)}$—$F_g$, —$OCF_2$—Cl, —O—$CF_2$—CHFCl, $(C_1$-$C_6)$-alkylmercapto, $(C_1$-$C_6)$-hydroxyalkyl, $(C_1$-$C_6)$-alkoxy-$(C_1$-$C_6)$-alkoxy, $(C_1$-$C_6)$-alkoxy-$(C_1$-$C_6)$-alkyl, $(C_1$-$C_6)$-alkylsulfinyl, $(C_1$-$C_6)$-alkylsulfonyl, $(C_1$-$C_6)$-alkylcarbonyl, $(C_1$-$C_8)$-alkoxycarbonyl, carbamoyl, N—$(C_1$-$C_8)$-alkylcarbamoyl, N,N-di-$(C_1$-$C_8)$-alkylcarbamoyl, or $(C_7$-$C_{11})$-aralkylcarbamoyl, optionally substituted by fluorine, chlorine, bromine, trifluoromethyl, $(C_1$-$C_6)$-alkoxy, N—$(C_3$-$C_8)$-Cycloalkylcarbamoyl, N—$(C_3$-$C_8)$-cycloalkyl-$(C_1$-$C_4)$-alkylcarbamoyl, $(C_1$-$C_6)$-alkylcarbonyloxy, phenyl, benzyl, phenoxy, benzyloxy, NR$^y$R$^z$ wherein R$^y$ and R$^z$ are independently selected from hydrogen, $(C_1$-$C_{12})$-alkyl, $(C_1$-$C_8)$-alkoxy-$(C_1$-$C_8)$-alkyl, $(C_7$-$C_{12})$-aralkoxy-$(C_1$-$C_8)$-alkyl, $(C_6$-$C_{12})$-aryloxy-$(C_1$-$C_8)$-alkyl, $(C_3$-$C_{10})$-cycloalkyl, $(C_3$-$C_{12})$-alkenyl, $(C_3$-$C_{12})$-alkynyl, $(C_6$-$C_{12})$-aryl, $(C_7$-$C_{11})$-aralkyl, $(C_1$-$C_{12})$-alkoxy, $(C_7$-$C_{12})$aralkoxy, $(C_1$-$C_{12})$-alkylcarbonyl, $(C_3$-$C_8)$-cycloalkylcarbonyl, $(C_6$-$C_{12})$ arylcarbonyl, $(C_7$-$C_{16})$-aralkylcarbonyl; or further wherein R$^y$ and R$^z$ together are —$[CH2]_h$, in which a $CH_2$ group can be replaced by O, S, N—$(C_1$-$C_4)$-alkylcarbonylimino, or N—$(C_1$-$C_4)$-alkoxycarbonylimino; phenylmercapto, phenylsulfinyl, phenylsulfonyl, sulfamoyl, N—$(C_1$-$C_8)$-alkylsulfamoyl, or N,N-di-$(C_1$-$C_8)$-alkylsulfamoyl; or alternatively $R^7$ and $R^8$, $R^8$ and $R^9$, $R^9$ and $R^{10}$, or $R^{10}$ and $R^{11}$, together are a chain selected from —$[CH_2]_n$— or —CH=CH—

CH=CH—, where a CH$_2$ group of the chain is optionally replaced by O, S, SO, SO$_2$, or NR$^Y$; and n is 3, 4, or 5; and if E is a heteroaryl radical, said radical can carry 1-3 substituents selected from those defined for R$^7$-R$^{11}$, or if E is a cycloalkyl radical, the radical can carry one substituent selected from those defined for R$^7$-R$^{11}$;

or where, if Q is NR', R$^4$ is alternatively R", where R' and R" are identical or different and are hydrogen, (C$_6$-C$_{12}$)-aryl, (C$_7$-C$_{11}$)-aralkyl, (C$_1$-C$_8$)-alkyl, (C$_1$-C$_8$)-alkoxy-(C$_1$-C$_8$)-alkyl, (C$_7$-C$_{12}$)-aralkoxy-(C$_1$-C$_8$)-alkyl, (C$_6$-C$_{12}$)-aryloxy-(C$_1$-C$_8$)-alkyl, (C$_1$-C$_{10}$)-alkylcarbonyl, optionally substituted (C$_7$-C$_{16}$)-aralkylcarbonyl, or optionally substituted C$_6$-C$_{12}$)-arylcarbonyl; or R' and R" together are —[CH$_2$]$_h$, in which a CH$_2$ group can be replaced by O, S, N-acylimino, or N—(C$_1$-C$_{10}$)-alkoxycarbonylimino, and h is 3 to 7.

Y is N or CR$^3$;

R$^1$, R$^2$ and R$^3$ are identical or different and are hydrogen, hydroxyl, halogen, cyano, trifluoromethyl, nitro, carboxyl, (C$_1$-C$_{20}$)-alkyl, (C$_3$-C$_8$)-cycloalkyl, (C$_3$-C$_8$)cycloalkyl-(C$_1$-C$_{12}$)-alkyl, (C$_3$-C$_8$)-cycloalkoxy, (C$_3$-C$_8$)-cycloalkyl-(C$_1$-C$_{12}$)-alkoxy, (C$_3$-C$_8$)-cycloalkyloxy-(C$_1$-C$_{12}$)-alkyl, (C$_3$-C$_8$)-cycloalkyloxy-(C$_1$-C$_{12}$)-alkoxy, (C$_3$-C$_8$)-cycloalkyl-(C$_1$-C$_8$)-alkyl-(C$_1$-C$_6$)-alkoxy, (C$_3$-C$_8$)-cycloalkyl-(C$_1$-C$_8$)-alkoxy-(C$_1$-C$_6$)-alkyl, (C$_3$-C$_8$)-cycloalkyloxy-(C$_1$-C$_8$)-alkoxy-(C$_1$-C$_8$)-alkyl, (C$_3$-C$_8$)-cycloalkoxy-(C$_1$-C$_8$)-alkoxy-(C$_1$-C$_8$)-alkoxy, (C$_6$-C$_{12}$)-aryl, (C$_7$-C$_{16}$)-aralkyl, (C$_7$-C$_{16}$)-aralkenyl, (C$_7$-C$_{16}$)-aralkynyl, (C$_2$-C$_{20}$)-alkenyl, (C$_2$-C$_{20}$)-alkynyl, (C$_1$-C$_{20}$)-alkoxy, (C$_2$-C$_{20}$)-alkenyloxy, (C$_2$-C$_{20}$)-alkynyloxy, retinyloxy, (C$_1$-C$_{20}$)-alkoxy-(C$_1$-C$_{12}$)-alkyl, (C$_1$-C$_{12}$)-alkoxy-(C$_1$-C$_{12}$)-alkoxy, (C$_1$-C$_{12}$)-alkoxy-(C$_1$-C$_8$)-alkoxy-(C$_1$-C$_8$)-alkyl, (C$_6$-C$_{12}$)-aryloxy, (C$_7$-C$_{16}$)-aralkyloxy, (C$_6$-C$_{12}$)-aryloxy-(C$_1$-C$_6$)-alkoxy, (C$_7$-C$_{16}$)-aralkoxy-(C$_1$-C$_6$)-alkoxy, (C$_1$-C$_{16}$)-hydroxyalkyl, (C$_6$-C$_{16}$)-aryloxy-(C$_1$-C$_8$)-alkyl, (C$_7$-C$_{16}$)-aralkoxy-(C$_1$-C$_8$)-alkyl, (C$_6$-C$_{12}$)-aryloxy-(C$_1$-C$_8$)-alkoxy-(C$_1$-C$_6$)-alkyl, (C$_7$-C$_{12}$)-aralkyloxy-(C$_1$-C$_8$)-alkoxy-(C$_1$-C$_6$)-alkyl, (C$_2$-C$_{20}$)-alkenyloxy-(C$_1$-C$_6$)-alkyl, (C$_2$-C$_{20}$)-alkynyloxy-(C$_1$-C$_6$)-alkyl, retinyloxy-(C$_1$-C$_6$)-alkyl, —O—[CH$_2$]$_x$CfH$_{(2f+1-g)}$F$_g$, —OCF$_2$Cl, —OCF$_2$—CHFCl, (C$_1$-C$_{20}$)-alkylcarbonyl, (C$_3$-C$_8$)-cycloalkylcarbonyl, (C$_6$-C$_{12}$)-arylcarbonyl, (C$_7$-C$_{16}$)-aralkylcarbonyl, cinnamoyl, (C$_2$-C$_{20}$)-alkenylcarbonyl, (C$_2$-C$_{20}$)-alkynylcarbonyl, (C$_1$-C$_{20}$)-alkoxycarbonyl, (C$_1$-C$_{12}$)-alkoxy-(C$_1$-C$_{12}$)-alkoxycarbonyl, (C$_6$-C$_{12}$)-aryloxycarbonyl, (C$_7$-C$_{16}$)-aralkoxycarbonyl, (C$_3$-C$_8$)-cycloalkoxycarbonyl, (C$_2$-C$_{20}$)-alkenyloxycarbonyl, retinyloxycarbonyl, (C$_2$-C$_{20}$)-alkynyloxycarbonyl, (C$_6$-C$_{12}$)-aryloxy-(C$_1$-C$_6$)-alkoxycarbonyl, (C$_7$-C$_{16}$)-aralkoxy-(C$_1$-C$_6$)-alkoxycarbonyl, (C$_3$-C$_8$)-cycloalkyl-(C$_1$-C$_6$)-alkoxycarbonyl, (C$_3$-C$_8$)-cycloalkoxy-(C$_1$-C$_6$)-alkoxycarbonyl, (C$_1$-C$_{12}$)-alkylcarbonyloxy, (C$_3$-C$_8$)-cycloalkylcarbonyloxy, (C$_6$-C$_{12}$)-arylcarbonyloxy, (C$_7$-C$_{16}$)-aralkylcarbonyloxy, cinnamoyloxy, (C$_2$-C$_{12}$)-alkenylcarbonyloxy, (C$_2$-C$_{12}$)-alkynylcarbonyloxy, (C$_1$-C$_{12}$)-alkoxycarbonyloxy, (C$_1$-C$_{12}$)-alkoxy-(C$_1$-C$_{12}$)-alkoxycarbonyloxy, (C$_6$-C$_{12}$)-aryloxycarbonyloxy, (C$_7$-C$_{16}$)-aralkyloxycarbonyloxy, (C$_3$-C$_8$)-cycloalkoxycarbonyloxy, (C$_2$-C$_{12}$)-alkenyloxycarbonyloxy, (C$_2$-C$_{12}$)-alkynyloxycarbonyloxy, carbamoyl, N—(C$_1$-C$_{12}$)-alkylcarbamoyl, N,N-di-(C$_1$-C$_{12}$)-alkylcarbamoyl, N—(C$_3$-C$_8$)-cycloalkylcarbamoyl, N,N-dicyclo-(C$_3$-C$_8$)-alkylcarbamoyl, N—(C$_1$-C$_{10}$)-alkyl-N—(C$_3$-C$_8$)-cycloalkylcarbamoyl, N—((C$_3$-C$_8$)-cycloalkyl-(C$_1$-C$_6$)-alkyl)-carbamoyl, N—(C$_1$-C$_6$)-alkyl-N—((C$_3$-C$_8$)-cycloalkyl-(C$_1$-C$_6$)-alkyl)-carbamoyl, N-(+)-dehydroabietylcarbamoyl, N—(C$_1$-C$_6$)-alkyl-N-(+)-dehydroabietylcarbamoyl, N—(C$_6$-C$_{12}$)-arylcarbamoyl, N—(C$_7$-C$_{16}$)-aralkylcarbamoyl, N—(C$_1$-C$_{10}$)-alkyl-N—(C$_6$-C$_{16}$)-arylcarbamoyl, N—(C$_1$-C$_{10}$)-alkyl-N—(C$_7$-C$_{16}$)-aralkylcarbamoyl, N—((C$_1$-C$_{18}$)-alkoxy-(C$_1$-C$_{10}$)-alkyl)-carbamoyl, N—((C$_6$-C$_{16}$)-aryloxy-(C$_1$-C$_{10}$)-alkyl)-carbamoyl, N—((C$_7$-C$_{16}$)-aralkyloxy-(C$_1$-C$_{10}$)-alkyl)-carbamoyl, N—(C$_1$-C$_{10}$)-alkyl-N—((C$_1$-C$_{10}$)-alkoxy-(C$_1$-C$_{10}$)-alkyl)-carbamoyl, N—(C$_1$-C$_{10}$)-alkyl-N—((C$_6$-C$_{12}$)-aryloxy-(C$_1$-C$_{10}$)-alkyl)-carbamoyl, N—(C$_1$-C$_{10}$)-alkyl-N—((C$_7$-C$_{16}$)-aralkyloxy-(C$_1$-C$_{10}$)-alkyl)-carbamoyl; CON (CH$_2$)$_h$, in which a CH$_2$ group can be replaced by O, S, N—(C$_1$-C$_8$)-alkylimino, N—(C$_3$-C$_8$)-cycloalkylimino, N—(C$_3$-C$_8$)-cycloalkyl-(C$_1$-C$_4$)-allylimino, N—(C$_6$-C$_{12}$)-arylimino, N—(C$_7$-C$_{16}$)-aralkylimino, N—(C$_1$-C$_4$)-alkoxy-(C$_1$-C$_6$)-allylimino, and h is from 3 to 7; a carbamoyl radical of the formula R

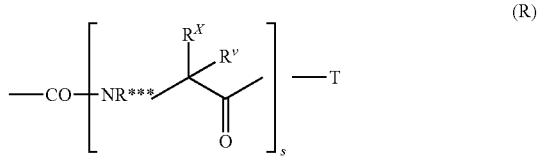

(R)

in which

R$^x$ and R$^v$ are each independently selected from hydrogen, (C$_1$-C$_6$)-alkyl, (C$_3$-C$_7$)-cycloalkyl, aryl, or the substituent of an α-carbon of an α-amino acid, to which the L- and D-amino acids belong, s is 1-5, T is OH, or NR*R**, and R*, R and R* are identical or different and are selected from hydrogen, (C$_6$-C$_{12}$)-aryl, (C$_7$-C$_{11}$)-aralkyl, (C$_1$-C$_8$)-alkyl, (C$_3$-C$_8$)-cycloalkyl, (+)-dehydroabietyl, (C$_1$-C$_8$)-alkoxy-(C$_1$-C$_8$)-alkyl, (C$_7$-C$_{12}$)-aralkoxy-(C$_1$-C$_8$)-alkyl, (C$_6$-C$_{12}$)-aryloxy-(C$_1$-C$_8$)-alkyl, (C$_1$-C$_{10}$)-alkanoyl, optionally substituted (C$_7$-C$_{16}$)-aralkanoyl, optionally substituted (C$_6$-C$_{12}$)-aroyl; or R* and R** together are —[CH$_2$]$_h$, in which a CH$_2$ group can be replaced by O, S, SO, SO$_2$, N-acylamino, N—(C$_1$-C$_{10}$)-alkoxycarbonylimino, N—(C$_1$-C$_8$)-alkylimino, N—(C$_3$-C$_8$)-cycloalkylimino, N—(C$_3$-C$_8$)-cycloalkyl-(C$_1$-C$_4$)-alkylimino, N—(C$_6$-C$_{12}$)-arylimino, N—(C$_7$-C$_{16}$)-aralkylimino, N—(C$_1$-C$_4$)-alkoxy-(C$_1$-C$_6$)-alkylimino, and h is from 3 to 7; carbamoyloxy, N—(C$_1$-C$_{12}$)-alkylcarbamoyloxy, N,N-di-(C$_1$-C$_{12}$)-alkylcarbamoyloxy, N—(C$_3$-C$_8$)-cycloalkylcarbamoyloxy, N—(C$_6$-C$_{12}$)-arylcarbamoyloxy, N—(C$_7$-c$_{16}$)-aralkylcarbamoyloxy, N—(C$_1$-C$_{10}$)-alkyl-N—(C$_6$-C$_{12}$)-arylcarbamoyloxy, N—(C$_1$-C$_{10}$)-alkyl-N—(C$_7$-C$_{16}$)-aralkylcarbamoyloxy, N—((C$_1$-C$_{10}$)-alkyl)-carbamoyloxy, N—((C$_6$-C$_{12}$)-aryloxy-(C$_1$-C$_{10}$)-alkyl)-carbamoyloxy, N—((C$_7$-C$_{16}$)-aralkyloxy-(C$_1$-C$_{10}$)-alkyl)-carbamoyloxy, N—(C$_1$-C$_{10}$)-alkyl-N—((C$_1$-C$_{10}$)-alkoxy-(C$_1$-C$_{10}$)-alkyl)-carbamoyloxy, N—(C$_1$-C$_{10}$)-alkyl-N—((C$_6$-C$_{12}$)-aryloxy-(C$_1$-C$_{10}$)-alkyl)-carbamoyloxy, N—(C$_1$-C$_{10}$)-alkyl-N—((C$_7$-C$_{16}$)-aralkyloxy-(C$_1$-C$_{10}$)-alkyl)-carbamoyloxyamino, (C$_1$-C$_{12}$)-alkylamino, di-(C$_1$-C$_{12}$)-alkylamino, (C$_3$-C$_8$)-cycloalkylamino, (C$_3$-C$_{12}$)-alkenylamino, (C$_3$-C$_{12}$)-alkynylamino, N—(C$_6$-C$_{12}$)-arylamino, N—(C$_7$-C$_{11}$)-aralkylamino, N-alkyl-aralkylamino, N-alkyl-arylamino, (C$_1$-C$_{12}$)-alkoxyamino, (C$_1$-C$_{12}$)-alkoxy-N—(C$_1$-C$_{10}$)-alkylamino, (C$_1$-C$_{12}$)-alkanoylamino, (C$_3$-C$_8$)-cycloalkanoylamino, (C$_6$-C$_{12}$)-aroylamino, (C$_7$-C$_{16}$)-aralkanoylamino, (C$_1$-C$_{12}$)-alkanoyl-N—(C$_1$-C$_{10}$)-alkylamino, (C$_3$-C$_8$)-cycloalkanoyl-N—(C$_1$-C$_{10}$)-alkylamino, (C$_6$-C$_{12}$)-aroyl-N—(C$_1$-C$_{10}$)-alkylamino, (C$_7$-C$_{11}$)-aralkanoyl-N—(C$_1$-C$_{10}$)-alkylamino, (C$_1$-C$_{12}$)-alkanoylamino-(C$_1$-C$_8$)-alkyl, (C$_3$-C$_8$)-cycloalkanoylamino-(C$_1$-C$_8$)-alkyl, (C$_6$-C$_{12}$)-aroylamino-(C$_1$-C$_8$)-alkyl, (C$_7$-C$_{16}$)-aralkanoylamino-(C$_1$-C$_8$)-alkyl, amino-(C$_1$-

$C_{10}$)-alkyl, N—($C_1$-$C_{10}$)-alkylamino-($C_1$-$C_{10}$)-alkyl, N,N-di($C_1$-$C_{10}$)-alkylamino-($C_1$-$C_{10}$)-alkyl, ($C_3$-$C_8$)-cycloalkylamino($C_1$-$C_{10}$)-alkyl, ($C_1$-$C_{20}$)-alkylmercapto, ($C_1$-$C_{20}$)-alkylsulfinyl, ($C_1$-$C_{20}$)-alkylsulfonyl, ($C_6$-$C_{12}$)-arylmercapto, ($C_6$-$C_{12}$)-arylsulfinyl, ($C_6$-$C_{12}$)-arylsulfonyl, ($C_7$-$C_{16}$)-aralkylmercapto, ($C_7$-$C_{16}$)-aralkylsulfinyl, ($C_7$-$C_{16}$)-aralkylsulfonyl, ($C_1$-$C_{12}$)-alkylmercapto-($C_1$-$C_6$)-alkyl, ($C_1$-$C_{12}$)-alkylsulfinyl-($C_1$-$C_6$)-alkyl, ($C_1$-$C_{12}$)-alkylsulfonyl-($C_1$-$C_6$)-alkyl, ($C_6$-$C_{12}$)-arylmercapto-($C_1$-$C_6$)-alkyl, ($C_6$-$C_{12}$)-arylsulfinyl-($C_1$-$C_6$)-alkyl, ($C_6$-$C_{12}$)-arylsulfonyl-($C_1$-$C_6$)-alkyl, ($C_7$-$C_{16}$)-aralkylmercapto-($C_1$-$C_6$)-alkyl, ($C_7$-$C_{16}$)-aralkylsulfinyl-($C_1$-$C_6$)-alkyl, ($C_7$-$C_{16}$)-aralkylsulfonyl-($C_1$-$C_6$)-alkyl, sulfamoyl, N—($C_1$-$C_{10}$)-alkylsulfamoyl, N,N-di-($C_1$-$C_{10}$)-alkylsulfamoyl, ($C_3$-$C_8$)-cycloalkylsulfamoyl, N—($C_6$-$C_{12}$)-arylsulfamoyl, N—($C_7$-$C_{16}$)-aralkylsulfamoyl, N—($C_1$-$C_{10}$)-alkyl-N—($C_6$-$C_{12}$)-arylsulfamoyl, N—($C_1$-$C_{10}$)-alkyl-N—($C_7$-$C_{16}$)-aralkylsulfamoyl, ($C_1$-$C_{10}$)-alkylsulfonamido, N—(($C_1$-$C_{10}$)-alkyl)-($C_1$-$C_{10}$)-alkylsulfonamido, ($C_7$-$C_{16}$)-aralkylsulfonamido, and N—(($C_1$-$C_{10}$)-alkyl-($C_7$-$C_{16}$)-aralkylsulfonamido; where an aryl radical may be substituted by 1 to 5 substituents selected from hydroxyl, halogen, cyano, trifluoromethyl, nitro, carboxyl, ($C_2$-$C_{16}$)-alkyl, ($C_3$-$C_8$)-cycloalkyl, ($C_3$-$C_8$)-cycloalkyl-($C_1$-$C_{12}$)-alkyl, ($C_3$-$C_8$)-cycloalkoxy, ($C_3$-$C_8$)-cycloalkyl-($C_1$-$C_{12}$)-alkoxy, ($C_3$-$C_8$)-cycloalkyloxy-($C_1$-$C_{12}$)-alkyl, ($C_3$-$C_8$)-cycloalkyloxy-($C_1$-$C_{12}$)-alkoxy, ($C_3$-$C_8$)-cycloalkyl-($C_1$-$C_8$)-alkyl-($C_1$-$C_6$)-alkoxy, ($C_3$-$C_8$)-cycloalkyl($C_1$-$C_8$)-alkoxy-($C_1$-$C_6$)-alkyl, ($C_3$-$C_8$)-cycloalkyloxy-($C_1$-$C_8$)-alkoxy-($C_1$-$C_6$)-alkyl, ($C_3$-$C_8$)-cycloalkoxy-($C_1$-$C_8$)-alkoxy-($C_1$-$C_8$)-alkoxy, ($C_6$-$C_{12}$)-aryl, ($C_7$-$C_{16}$)-aralkyl, ($C_2$-$C_{16}$)-alkenyl, ($C_2$-$C_{12}$)-alkynyl, ($C_1$-$C_{16}$)-alkoxy, ($C_1$-$C_{16}$)-alkenyloxy, ($C_1$-$C_{12}$)-alkoxy-($C_1$-$C_{12}$)-alkyl, ($C_1$-$C_{12}$)-alkoxy-($C_1$-$C_{12}$)-alkoxy, ($C_1$-$C_{12}$)-alkoxy, ($C_1$-$C_8$)-alkoxy-($C_1$-$C_8$)-alkyl, ($C_6$-$C_{12}$)-aryloxy, ($C_7$-$C_{16}$)-aralkyloxy, ($C_6$-$C_{12}$)-aryloxy-($C_1$-$C_6$)-alkoxy, ($C_7$-$C_{16}$)-aralkoxy-($C_1$-$C_6$)-alkoxy, ($C_1$-$C_8$)-hydroxyalkyl, ($C_6$-$C_{16}$)-aryloxy-($C_1$-$C_8$)-alkyl, ($C_7$-$C_{16}$)-aralkoxy-($C_1$-$C_8$)-alkyl, ($C_6$-$C_{12}$)-aryloxy-($C_1$-$C_8$)-alkoxy-($C_1$-$C_6$)-alkyl, ($C_7$-$C_{12}$)-aralkyloxy-($C_1$-$C_8$)-alkoxy-($C_1$-$C_6$)-alkyl, —O—[$CH_2$]$_x$$C_f$$H_{(2f+1-g)}$$F_g$, —$OCF_2Cl$, —$OCF_2$—CHFCl, ($C_1$-$C_{12}$)-alkylcarbonyl, ($C_3$-$C_8$)-cycloalkylcarbonyl, ($C_6$-$C_{12}$)-arylcarbonyl, ($C_7$-$C_{16}$)-aralkylcarbonyl, ($C_1$-$C_{12}$)-alkoxycarbonyl, ($C_1$-$C_{12}$)-alkoxy-($C_1$-$C_{12}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{12}$)-alkenyloxycarbonyl, ($C_2$-$C_{12}$)-alkynyloxycarbonyl, ($C_6$-$C_{12}$)-aryloxy-($C_1$-$C_6$)-alkoxycarbonyl, ($C_7$-$C_{16}$)-aralkoxy-($C_1$-$C_6$)-alkoxycarbonyl, ($C_3$-$C_8$)-cycloalkyl-($C_1$-$C_6$)-alkoxycarbonyl, ($C_3$-$C_8$)-cycloalkoxy-($C_1$-$C_6$)-alkoxycarbonyl, ($C_1$-$C_{12}$)-alkylcarbonyloxy, ($C_3$-$C_8$)-cycloalkylcarbonyloxy, ($C_6$-$C_{12}$)-arylcarbonyloxy, ($C_7$-$C_{16}$)-aralkylcarbonyloxy, cinnamoyloxy, ($C_2$-$C_{12}$)-alkenylcarbonyloxy, ($C_2$-$C_{12}$)-alkynylcarbonyloxy, ($C_1$-$C_{12}$)-alkoxycarbonyloxy, ($C_1$-$C_{12}$)-alkoxy-($C_1$-$C_{12}$)-alkoxycarbonyloxy, ($C_6$-$C_{12}$)-aryloxycarbonyloxy, ($C_7$-$C_{16}$)-aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxycarbonyloxy, carbamoyl, N—($C_1$-$C_{12}$)-alkylcarbamoyl, N,N-di($C_1$-$C_{12}$)-alkylcarbamoyl, N—($C_3$-$C_8$)-cycloalkylcarbamoyl, N,N-dicyclo-($C_3$-$C_8$)-alkylcarbamoyl, N—($C_1$-$C_{10}$)-alkyl-N—($C_3$-$C_8$)-cycloalkylcarbamoyl, N—(($C_3$-$C_8$)-cycloalkyl-($C_1$-$C_6$)-allyl)carbamoyl, N—($C_1$-$C_6$)-alkyl-N—(($C_3$-$C_8$)-cycloalkyl-($C_1$-$C_6$)-alkyl)carbamoyl, N-(+)-dehydroabietylcarbamoyl, N—($C_1$-$C_6$)-alkyl-N-(+)-dehydroabietylcarbamoyl, N—($C_6$-$C_{12}$)-arylcarbamoyl, N—($C_7$-$C_{16}$)-aralkylcarbamoyl, N—($C_1$-$C_{10}$)-alkyl-N—($C_6$-$C_{16}$)-arylcarbamoyl, N—($C_1$-$C_{10}$)-alkyl-N—($C_7$-$C_{16}$)-aralkylcarbamoyl, N—(($C_1$-$C_{16}$)-alkoxy-($C_1$-$C_{10}$)-alkyl)carbamoyl, N—(($C_6$-$C_{16}$)-aryloxy-($C_1$-$C_{10}$)-alkyl)carbamoyl, N—(($C_7$-$C_{16}$)-aralkyloxy-($C_1$-$C_{10}$)-alkyl)carbamoyl, N—($C_1$-$C_{10}$)-alkyl-N—(($C_1$-$C_{10}$)-alkoxy-($C_1$-$C_{10}$)-alkyl)carbamoyl, N—($C_1$-$C_{10}$)-alkyl-N—(($C_6$-$C_{12}$)-aryloxy-($C_1$-$C_{10}$)-alkyl)carbamoyl, N—($C_1$-$C_{10}$)-alkyl-N—(($C_7$-$C_{16}$)-aralkyloxy-($C_1$-$C_{10}$)-alkyl)-carbamoyl, $CON(CH_2)_h$, in which a $CH_2$ group can be replaced by, O, S, N—($C_1$-$C_8$)-alkylimino, N—($C_3$-$C_8$)-cycloalkylimino, N—($C_3$-$C_8$)-cycloalkyl-($C_1$-$C_4$)-alkylimino, N—($C_6$-$C_{12}$)-arylimino, N—($C_7$-$C_{16}$)-aralkylimino, N—($C_1$-$C_4$)-alkoxy-($C_1$-$C_6$)-allylimino, and h is from 3 to 7; carbamoyloxy, N—($C_1$-$C_{12}$)-alkylcarbamoyloxy, N,N-di-($C_1$-$C_{12}$)-alkylcarbamoyloxy, N—($C_3$-$C_8$)-cycloalkylcarbamoyloxy, N—($C_6$-$C_{16}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N—($C_1$-$C_{10}$)-alkyl-N—($C_7$-$C_{16}$)-aralkylcarbamoyloxy, N—(($C_1$-$C_{10}$)-alkyl)carbamoyloxy, N—(($C_6$-$C_{12}$)-aryloxy-($C_1$-$C_{10}$)-alkyl)carbamoyloxy, N—(($C_7$-$C_{16}$)-aralkyloxy-($C_1$-$C_{10}$)-alkyl)carbamoyloxy, N—($C_1$-$C_{10}$)-alkyl-N—(($C_1$-$C_{10}$)-alkoxy-($C_1$-$C_{10}$)-alkyl)carbamoyloxy, N—($C_1$-$C_{10}$)-alkyl-N—(($C_6$-$C_{12}$)-aryloxy-($C_1$-$C_{10}$)-alkyl)carbamoyloxy, N—($C_1$-$C_{10}$)-alkyl-N—(($C_7$-$C_{16}$)-aralkyloxy-($C_1$-$C_{10}$)-alkyl)carbamoyloxy, amino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_{12}$)-alkynylamino, N—($C_6$-$C_{12}$)-arylamino, N—($C_7$-$C_{11}$)-aralkylamino, N-alkyl-aralkylamino, N-alkyl-arylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkanoylamino, ($C_3$-$C_8$)-cycloalkanoylamino, ($C_6$-$C_{12}$)-aroylamino, ($C_7$-$C_{16}$)-aralkanoylamino, ($C_1$-$C_{12}$)-alkanoyl-N—($C_1$-$C_{10}$)-alkylamino, ($C_3$-$C_8$)-cycloalkanoyl-N—($C_1$-$C_{10}$)-alkylamino, ($C_6$-$C_{12}$)-aroyl-N—($C_1$-$C_{10}$)-alkylamino, ($C_7$-$C_{11}$)-aralkanoyl-N—($C_1$-$C_{10}$)-alkylamino, ($C_1$-$C_{12}$)-alkanoylamino-($C_1$-$C_8$)-alkyl, ($C_3$-$C_8$)-cycloalkanoylamino-($C_1$-$C_8$)-alkyl, ($C_6$-$C_{12}$)-aroylamino-($C_1$-$C_8$)-alkyl, ($C_7$-$C_{16}$)-aralkanoylamino-($C_1$-$C_8$)-alkyl, amino-($C_1$-$C_{10}$)-alkyl, N—($C_1$-$C_{10}$)-alkylamino-($C_1$-$C_{10}$)-alkyl, N,N-di-($C_1$-$C_{10}$)-alkylamino-($C_1$-$C_{10}$)-alkyl, ($C_3$-$C_8$)-cycloalkylamino-($C_1$-$C_{10}$)-alkyl, ($C_1$-$C_{12}$)-alkylmercapto, ($C_1$-$C_{12}$)-alkylsulfinyl, ($C_1$-$C_{12}$)-alkylsulfonyl, ($C_6$-$C_{16}$)-arylmercapto, ($C_6$-$C_{16}$)-arylsulfinyl, ($C_6$-$C_{16}$)-arylsulfonyl, ($C_7$-$C_{16}$)-aralkylmercapto, ($C_7$-$C_{16}$)-aralkylsulfinyl, or ($C_7$-$C_{16}$)-aralkylsulfonyl;

or wherein $R^1$ and $R^2$, or $R^2$ and $R^3$ form a chain [$CH_2$]$_o$, which is saturated or unsaturated by a C=C double bond, in which 1 or 2 $CH_2$ groups are optionally replaced by O, S, SO, $SO_2$, or NR', and R' is hydrogen, ($C_6$-$C_{12}$)-aryl, ($C_1$-$C_8$-alkyl, ($C_1$-$C_8$)-alkoxy-($C_1$-$C_8$)-alkyl, ($C_7$-$C_{12}$)-aralkoxy-($C_1$-$C_8$)-alkyl, ($C_6$-$C_{12}$)-aryloxy-($C_1$-$C_8$)-alkyl, ($C_1$-$C_{10}$)-alkanoyl, optionally substituted ($C_7$-$C_{16}$)-aralkanoyl, or optionally substituted (C6-C12)-aroyl; and o is 3, 4 or 5;

or wherein the radicals $R^1$ and $R^2$, or $R^2$ and $R^3$, together with the pyridine or pyridazine carrying them, form a 5,6,7,8-tetrahydroisoquinoline ring, a 5,6,7,8-tetrahydroquinoline ring, or a 5,6,7,8-tetrahydrocinnoline ring;

or wherein $R^1$ and $R^2$, or $R^2$ and $R^3$ form a carbocyclic or heterocyclic 5- or 6-membered aromatic ring;

or where $R^1$ and $R^2$, or $R^2$ and $R^3$, together with the pyridine or pyridazine carrying them, form an optionally substituted heterocyclic ring systems selected from thienopyridines, furanopyridines, pyridopyridines, pyrimidinopyridines, imidazopyridines, thiazolopyridines, oxazolopyridines, quinoline, isoquinoline, and cinnoline; where quinoline, isoquinoline or cinnoline preferably satisfy the formulae Ia, Ib and Ic:

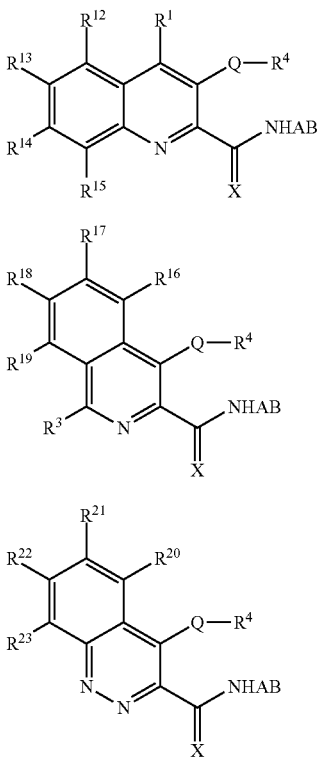

(Ia)

(Ib)

(Ic)

and the substituents $R^{12}$ to $R^{23}$ in each case independently of each other have the meaning of $R^1$, $R^2$ and $R^3$;
or wherein the radicals $R^1$ and $R^2$, together with the pyridine carrying them, form a compound of Formula Id:

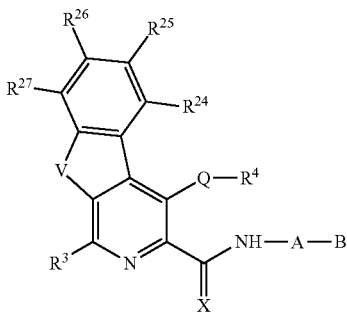

(Id)

where V is S, O, or $NR^k$, and $R^k$ is selected from hydrogen, $(C_1-C_6)$-alkyl, aryl, or benzyl; where an aryl radical may be optionally substituted by 1 to 5 substituents as defined above; and
$R^{24}$, $R^{25}$, $R^{26}$, and $R^{27}$ in each case independently of each other have the meaning of $R^1$, $R^2$ and $R^3$;
f is 1 to 8;
g is 0 or 1 to (2f+1);
x is 0 to 3; and
h is 3 to 7;
including the physiologically active salts and prodrugs derived therefrom.

In some embodiments, compounds of Formula (I) as defined above include, but are not limited to, [(3-methoxy-pyridine-2-carbonyl)-amino]-acetic acid; 3-methoxypyridine-2-carboxylic acid N-(((hexadecyloxy)-carbonyl)-methyl)-amide hydrochloride; 3-methoxypyridine-2-carboxylic acid N-(((1-octyloxy)-carbonyl)-methyl)-amide; 3-methoxypyridine-2-carboxylic acid N-(((hexyloxy)-carbonyl)-methyl)-amide; 3-methoxypyridine-2-carboxylic acid N-(((butyloxy)-carbonyl)-methyl)-amide; 3-methoxypyridine-2-carboxylic acid N-(((2-nonyloxy)-carbonyl)-methyl)-amide racemate; 3-methoxypyridine-2-carboxylic acid N-(((heptyloxy)-carbonyl)-methyl)-amide; 3-benzyloxypyridine-2-carboxylic acid N-(((octyloxy)-carbonyl)-methyl)-amide; 3-benzyloxypyridine-2-carboxylic acid N-(((butyloxy)-carbonyl)-methyl)-amide; 5-(((3-(1-butyloxy)-propyl)-amino)-carbonyl)-3-methoxypyridine-2-carboxylic acid N-((benzyloxycarbonyl)-methyl)-amide; 5-(((3-(1-butyloxy)-propyl)-amino)-carbonyl)-3-methoxypyridine-2-carboxylic acid N-(((1-butyloxy)-carbonyl)-methyl)-amide; 5-(((3-lauryloxy)-propyl)amino)-carbonyl)-3-methoxypyridine-2-carboxylic acid N-(((benzyloxy)-carbonyl)-methyl)-amide, [(3-hydroxy-pyridine-2-carbonyl)-amino]-acetic acid; and [(3-methoxy-pyridine-2-carbonyl)-amino]-acetic acid. In other embodiments, compounds of Formula (Ia) as defined above include, but are not limited to, N-((3-Hydroxy-6-isopropoxyquinoline-2-carbonyl)-amino)-acetic acid, N-((6-(1-butyloxy)-3-hydroxyquinolin-2-yl)-carbonyl)-glycine, [(3-hydroxy-6-trifluoromethoxy-quinoline-2-carbonyl)-amino]-acetic acid, N-((6-chloro-3-hydroxyquinolin-2-yl)-carbonyl)-glycine, N-((7-chloro-3-hydroxyquinolin-2-yl)-carbonyl)-glycine, and [(6-chloro-3-hydroxy-quinoline-2-carbonyl)-amino]-acetic acid. In still other embodiments, the compounds of Formula (Ib) as defined above include, but are not limited to, N-((1-chloro-4-hydroxy-7-(2-propyloxy) isoquinolin-3-yl)-carbonyl)-glycine, N-((1-chloro-4-hydroxy-6-(2-propyloxy) isoquinolin-3-yl)-carbonyl)-glycine, N-((1-chloro-4-hydroxy-isoquinoline-3-carbonyl)-amino)-acetic acid, N-((1-chloro-4-hydroxy-7-methoxyisoquinolin-3-yl)-carbonyl)-glycine, N-((1-chloro-4-hydroxy-6-methoxyisoquinolin-3-yl)-carbonyl)-glycine, N-((7-butyloxy)-1-chloro-4-hydroxyisoquinolin-3-yl)-carbonyl)-glycine, N-((6-benzyloxy-1-chloro-4-hydroxy-isoquinoline-3-carbonyl)-amino)-acetic acid, ((7-benzyloxy-1-chloro-4-hydroxyisoquinoline-3-carbonyl)-amino)-acetic acid methyl ester, N-((7-benzyloxy-1-chloro-4-hydroxy-isoquinoline-3-carbonyl)-amino)-acetic acid, N-((8-chloro-4-hydroxyisoquinolin-3-yl)-carbonyl)-glycine, N-((7-butoxy-4-hydroxy-isoquinoline-3-carbonyl)-amino)-acetic acid.

In other embodiments, compounds used in the methods of the invention are selected from a compound of the formula (II)

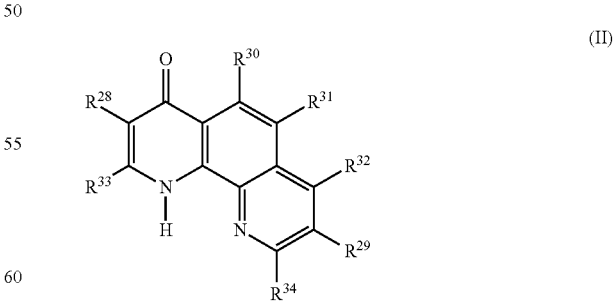

(II)

where
$R^{28}$ is hydrogen, nitro, amino, cyano, halogen, $(C_1-C_4)$-alkyl, carboxy or a metabolically labile ester derivative thereof; $(C_1-C_4)$-alkylamino, di-$(C_1-C_4)$-alkylamino, $(C_1-C_6)$-alkoxycarbonyl, $(C_2-C_4)$-alkanoyl, hydroxy-$(C_1-C_4)$-alkyl, carbamoyl, N—($C_1$-$C_4$)-alkylcarbamoyl, ($C_1$-$C_4$)-alkylthio, ($C_1$-$C_4$)-alkylsulfinyl, ($C_1$-$C_4$)-alkylsulfonyl, phenylthio, phenylsulfinyl, phenylsulfonyl, said phenyl or phenyl groups being optionally substituted with 1 to 4 identical or different halogen, ($C_1$-$C_4$)-alkyoxy, ($C_1$-$C_4$)-alkyl, cyano, hydroxy, trifluoromethyl, fluoro-($C_1$-$C_4$)-alkylthio, fluoro-($C_1$-$C_4$)-alkylsulfinyl, fluoro-($C_1$-$C_4$)-alkylsulfonyl, ($C_1$-$C_4$)-alkoxy-($C_2$-$C_4$)-alkoxycarbonyl, N,N-di-[($C_1$-$C_4$)-alkyl]carbamoyl-($C_1$-$C_4$)-alkoxycarbonyl, ($C_1$-$C_4$)-alkylamino-($C_2$-$C_4$)-alkoxycarbonyl, di-($C_1$-$C_4$)-alkylamino-($C_2$-$C_4$)-alkoxycarbonyl, ($C_1$-$C_4$)-alkoxy-($C_2$-$C_4$)-alkoxy-($C_2$-$C_4$)-alkoxycarbonyl, ($C_2$-$C_4$)-alkanoyloxy-$C_1$-$C_4$)-alkyl, or N-[amino-($C_2$-$C_8$)-alkyl]-carbamoyl;

$R^{29}$ is hydrogen, hydroxy, amino, cyano, halogen, ($C_1$-$C_4$)-alkyl, carboxy or metabolically labile ester derivative thereof, ($C_1$-$C_4$)-alkylamino, di-($C_1$-$C_4$)-alkylamino, ($C_1$-$C_6$)-alkoxycarbonyl, ($C_2$-$C_4$)-alkanoyl, ($C_1$-$C_4$)-alkoxy, carboxy-($C_1$-$C_4$)-alkoxy, ($C_1$-$C_4$)-alkoxycarbonyl-($C_1$-$C_4$)-alkoxy, carbamoyl, N—($C_1$-$C_8$)-alkylcarbamoyl, N,N-di-($C_1$-$C_8$)-alkylcarbamoyl, N-[amino-($C_2$-$C_8$)-alkyl]-carbamoyl, N—($C_1$-$C_4$)-alkylamino-($C_1$-$C_8$)-alkyl]-carbamoyl, N-[di-($C_1$-$C_4$)-alkylamino-($C_1$-$C_8$)-alkyl)]carbamoyl, N-cyclohexylcarbamoyl, N-[cyclopentyl]-carbamoyl, N—($C_1$-$C_4$)-alkylcyclohexylcarbamoyl, N—($C_1$-$C_4$)-alkylcyclopentylcarbamoyl, N-phenylcarbamoyl, N—($C_1$-$C_4$)-alkyl-N-phenylcarbamoyl, N,N-diphenylcarbamoyl, N-[phenyl-($C_1$-$C_4$)-alkyl]-carbamoyl, N—($C_1$-$C_4$)-alkyl-N-[phenyl-($C_1$-$C_4$)-alkyl]-carbamoyl, or N,N-di-[phenyl-($C_1$-$C_4$)-alkyl]-carbamoyl, said phenyl or phenyl groups being optionally substituted with 1 to 4 identical or different halogen, ($C_1$-$C_4$)-alkyoxy, cyano, hydroxy, trifluoromethyl, N—[($C_2$-$C_4$)-alkanoyl]-carbamoyl, N—[($C_1$-$C_4$)-alkoxycarbonyl]-carbamoyl, N-[fluoro-($C_2$-$C_6$)-alkyl]-carbamoyl, N,N-[fluoro-($C_2$-$C_6$)-alkyl]-N—($C_1$-$C_4$)-alkylcarbamoyl, N,N-[di-fluoro-($C_2$-$C_6$)-alkyl]carbamoyl, pyrrolidin-1-ylcarbonyl, piperidinocarbonyl, piperazin-1-ylcarbonyl, morpholinocarbonyl, wherein the heterocyclic group, is optionally substituted with 1 to 4, ($C_1$-$C_4$)-alkyl, benzyl, 1,2,3,4-tetrahydro-isoquinolin-2-ylcarbonyl, N,N-[di-($C_1$-$C_4$)-alkyl]-thiocarbamoyl, N—($C_2$-$C_4$)-alkanoylamino, or N-[($C_1$-$C_4$)-alkoxycarbonyl]-amino;

$R^{30}$ is hydrogen, ($C_1$-$C_4$)-alkyl, ($C_2$-$C_4$)-alkoxy, halo, nitro, hydroxy, fluoro-(1-4C)alkyl, or pyridinyl;

$R^{31}$ is hydrogen, ($C_1$-$C_4$)-alkyl, ($C_2$-$C_4$)-alkoxy, halo, nitro, hydroxy, fluoro-($C_1$-$C_4$)-alkyl, pyridinyl, or methoxy;

$R^{32}$ is hydrogen, hydroxy, amino, ($C_1$-$C_4$)-alkylamino, di-($C_1$-$C_4$)-alkylamino, halo, ($C_1$-$C_4$)-alkoxy-($C_2$-$C_4$)-alkoxy, fluoro-($C_1$-$C_6$)-alkoxy, pyrrolidin-1-yl, piperidino, piperazin-1-yl, or morpholino, wherein the heterocyclic group is optionally substituted with 1 to 4 identical or different ($C_1$-$C_4$)-alkyl or benzyl; and $R^{33}$ and $R^{34}$ are individually selected from hydrogen, ($C_1$-$C_4$)-alkyl, and ($C_1$-$C_4$)-alkoxy; including pharmaceutically-acceptable salts and pro-drugs derived therefrom.

In some embodiments, compounds of Formula (II) as defined above include, but are not limited to, 4-oxo-1,4-dihydro-[1,10]phenanthroline-3-carboxylic acid, 3-carboxy-5-hydroxy-4-oxo-3,4-dihydro-1,10-phenanthroline, 3-carboxy-5-methoxy-4-oxo-3,4-dihydro-1,10-phenanthroline, 5-methoxy-4-oxo-1,4-dihydro-[1,10]phenanthroline-3-carboxylic acid ethyl ester, 5-methoxy-4-oxo-1,4-dihydro-[1,10]phenanthroline-3-carboxylic acid, and 3-carboxy-8-hydroxy-4-oxo-3,4-dihydro-1,10-phenanthroline.

The compounds can be administered singly or in combination with various other therapeutic approaches. In one embodiment, the compound is administered with another 2-oxoglutarate dioxygenase inhibitor, wherein the two compounds have differential specificity for individual 2-oxoglutarate dioxygenase family members. The two compounds may be administered at the same time as a ratio of one relative to the other or may be administered consecutively during a treatment time course, e.g., following myocardial infarction. In one specific embodiment, one compound specifically inhibits HIF prolyl hydroxylase activity, and a second compound specifically inhibits procollagen prolyl 4-hydroxylase activity. In another embodiment, the compound is administered with another therapeutic agent having a different mode of action, e.g., an ACE inhibitor (ACEI), angiotensin-H receptor blocker (ARB), diuretic, and/or digoxin. In yet another embodiment, the compound is administered with carnitine.

In one aspect, a compound of the invention inhibits one or more 2-oxoglutarate dioxygenase enzymes. In one embodiment, the compound inhibits at least two 2-oxoglutarate dioxygenase family members, e.g., HIF prolyl hydroxylase and procollagen prolyl 4-hydroxylase, with either the same specificity or with differential specificity. In another embodiment, the compound is specific for one 2-oxoglutarate dioxygenase, e.g., HIF prolyl hydroxylase, and shows little to no specificity for other family members.

Preferred embodiments of the invention comprise methods using oral and transdermal delivery mechanisms. Thus, the present invention also provides an oral formulation comprising a compound of the invention. In another preferred embodiment, the present methods involve transdermal administration of a compound of the invention. Thus, the present invention also provides a transdermal patch or pad comprising a compound of the invention.

These and other embodiments of the subject invention will readily occur to those of skill in the art in light of the disclosure herein, and all such embodiments are specifically contemplated.

BRIEF DESCRIPTION OF THE DRAWINGS

FIG. 1A shows stabilization and accumulation of HIF-1α in human foreskin fibroblasts (HFF) treated with various compounds of the invention. FIG. 1B shows a dose response for HIF-1α stabilization and accumulation in different human cells treated with a compound of the invention. Cell lines shown in the figure include HFF, human microvascular endothelial cells (HMEC), venous endothelium (AG7), human umbilical vein endothelial cells (HUVEC), squamous cell carcinoma (SCC), human lung fibroblasts (HLF), mammary gland epithelial adenocarcinoma (MCF7), transformed fetal kidney cells (293A), and cervical adenocarcinoma cells (HeLa).

FIG. 2A shows 293A and human hepatocarcinoma cells (Hep3B) treated with various compounds of the invention. FIG. 2B shows a dose response for HIF-1α stabilization in Hep3B cells treated with exemplary compounds of the invention.

FIG. 3A shows single-dose and dose-response oxygen consumption in cells treated with various compounds of the invention. FIG. 3B shows cell proliferation and viability as measured by cleavage of WST-1 tetrazolium salt (Roche Diagnostics Corp., Indianapolis Ind.) in cells treated with selected compounds from FIG. 3A.

FIG. 4A shows levels of vascular endothelial growth factor (VEGF), a key gene in blood vessel formation, in human cell culture media following treatment with compounds of the invention. Cell lines shown in the figure are 293A, Hep3B, and HFF. FIG. 4B shows a time course for increase in aldolase, a key enzyme in the glycolytic pathway, in cells treated with a compound of the invention.

FIG. 5A shows a montage of angiogenic gene expression. Genes represented in the figure include vascular endothelial growth factor (VEGF)-C, Flt-1/VEGF receptor-1, adrenomedullin, endothelin-1, plasminogen activator inhibitor (PAI)-1, and Cyr61. FIG. 5B shows expression of genes encoding endothelin-1 and adrenomedullin selected from FIG. 5A.

FIG. 6A shows increased levels of transcript encoding VEGF in liver and kidney of mice treated with compounds of the invention. FIG. 6B shows levels of VEGF in mouse plasma at 2, 5, and 20 hours following final treatment with a compound of the invention relative to an untreated control group.

FIG. 7A shows a montage of glycolytic gene expression. Genes represented in the figure include aldolase-A, enolase-1, Glut1, Glut3, GAPDH, hexokinase-1 and -2, lactate dehydrogenase-A, phosphofructokinase-L and -C, phosphoglycerate kinase-1, and pyruvate kinase-M. FIG. 7B shows expression of genes encoding aldolase-A and phosphofructokinase-L selected from FIG. 7A.

FIG. 9A shows changes in the left ventricular end systolic diameter (LVESD) in a group treated with a compound of the invention relative to an untreated group at time intervals following induced myocardial infarction. FIG. 9B shows changes in the left ventricular end diastolic diameter (LVEDD) in a group treated with a compound of the invention relative to an untreated group at time intervals following induced myocardial infarction.

FIG. 10A shows changes in the left ventricular ejection fraction in a group treated with a compound of the invention relative to an untreated group at time intervals following induced myocardial infarction. FIG. 10B shows changes in the fractional shortening in a group treated with a compound of the invention relative to an untreated group at time intervals following induced myocardial infarction.

FIG. 12A shows statistically significant improvement ($p<0.05$) in fractional shortening in treated animals relative to untreated controls one week after induced myocardial infarction. FIG. 12B shows statistically significant improvement in left ventricle end-diastolic diameter (LVEDD; $p<0.005$) and left ventricular end-systolic diameter (LVESD; $p<0.001$) in treated animals relative to untreated controls one week after induced myocardial infarction.

FIG. 14A shows lower blood urea nitrogen levels in treated animals relative to untreated controls at 3 and 7 days after inducing ischemia-reperfusion injury. FIG. 14B shows lower blood cholesterol levels in treated animals relative to untreated controls at 3, 7, and 14 days after inducing ischemia-reperfusion injury.

FIG. 15A shows increased epithelialization and formation of granulation tissue in treated animals relative to untreated controls 7 and 10 days after induction of wounds. FIG. 15B shows no difference in peak-peak distance within the scar in treated animals relative to untreated controls.

DESCRIPTION OF THE INVENTION

Figure 1:
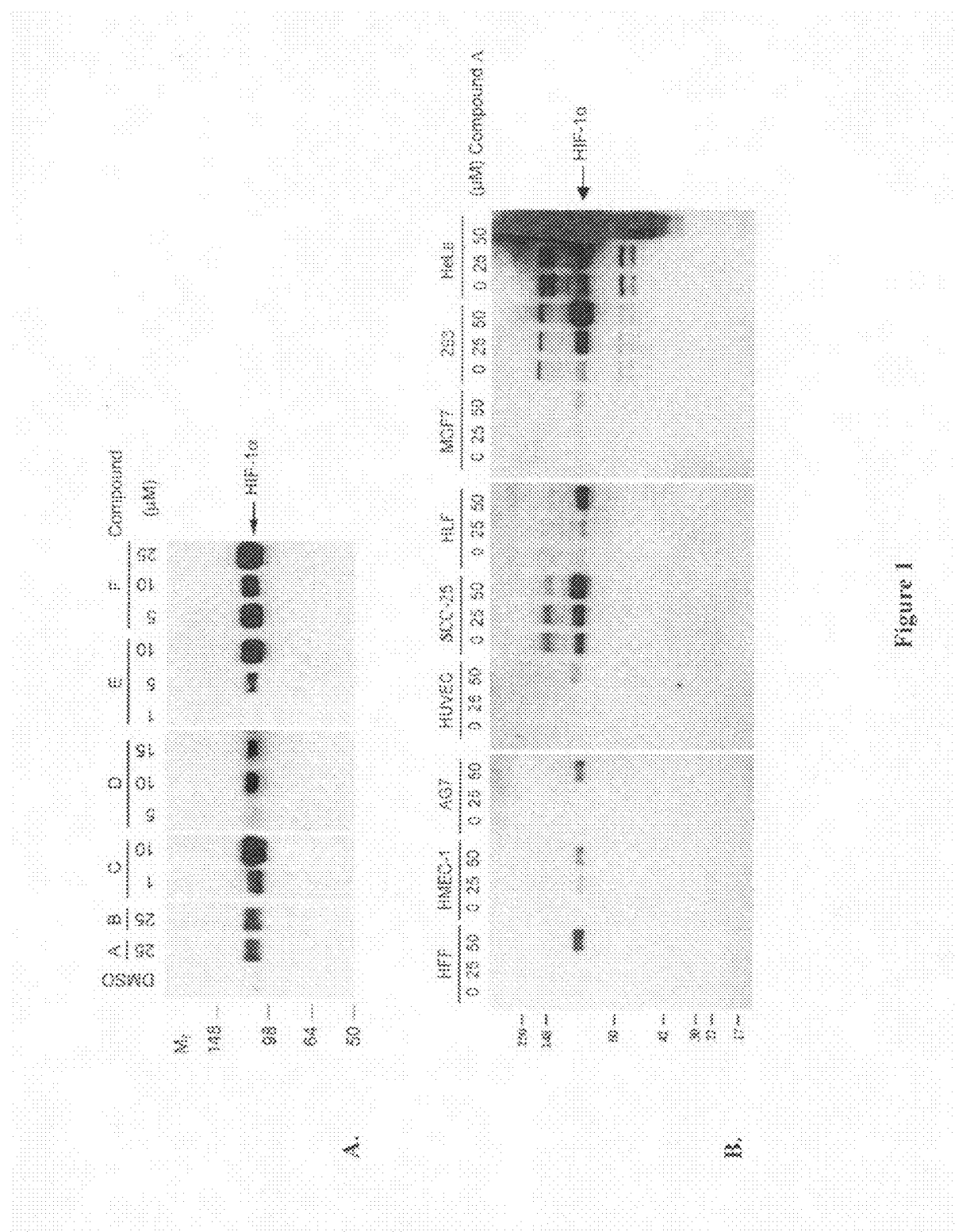
FIGS. 1A and 1B show HIF-1α stabilization in cells treated with compounds of the invention.

Before the present compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless context clearly dictates otherwise. Thus, for example, a reference to "a fragment" includes a plurality of such fragments; a reference to an "antibody" is a reference to one or more antibodies and to equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) *Remington's Pharmaceutical Sciences,* 18$^{th}$ ed., Mack Publishing Co.; Hardman, J. G., Limbird, L. E., and Gilman, A. G., eds. (2001) *The Pharmacological Basis of Therapeutics*, 10$^{th}$ ed., McGraw-Hill Co.; Colowick, S. et al., eds., *Methods In Enzymology*, Academic Press, Inc.; Weir, D. M., and Blackwell, C. C., eds. (1986) *Handbook of Experimental Immunology*, Vols. I-IV, Blackwell Scientific Publications; Maniatis, T. et al., eds. (1989) *Molecular Cloning: A Laboratory Manual*, 2$^{nd}$ edition, Vols. I-III, Cold Spring Harbor Laboratory Press; Ausubel, F. M. et al., eds. (1999) *Short Protocols in Molecular Biology*, 4$^{th}$ edition, John Wiley & Sons; Ream et al., eds. (1998) *Molecular Biology Techniques: An Intensive Laboratory Course*, Academic Press; Newton, C. R., and Graham, A., eds. (1997) *PCR (Introduction to Biotechniques Series)*, 2$^{nd}$ ed., Springer Verlag.

DEFINITIONS

The term "ischemia" refers to a reduction in blood flow. Ischemia is associated with a reduction in nutrients, including oxygen, delivered to tissues. Ischemia may arise due to conditions such as atherosclerosis, formation of a thrombus in an artery or vein, or blockage of an artery or vein by an embolus, vascular closure due to other causes, e.g., vascular spasm, etc. Such conditions may reduce blood flow, producing a state of hypoperfusion to an organ or tissue, or block blood flow completely. Other conditions that can produce ischemia include tissue damage due to trauma or injury, such as, e.g., spinal cord injury; viral infection, which can lead to, e.g., congestive heart failure, etc. The terms "ischemic conditions" and "ischemic disorders" refer to acute ischemic conditions including, but not limited to, myocardial infarction, ischemic stroke, pulmonary embolism, perinatal hypoxia, circulatory shock including, e.g., hemorrhagic, septic, cardiogenic, etc., mountain sickness, acute respiratory failure, etc., chronic ischemic conditions including atherosclerosis, chronic venous insufficiency, chronic heart failure, cardiac cirrhosis, diabetes, macular degeneration, sleep apnea, Raynaud's disease, systemic sclerosis, nonbacterial thrombotic endocarditis, occlusive artery disease, angina pectoris, TIAs, chronic alcoholic liver disease, etc. Ischemic conditions may also result when individuals are placed under general anesthesia, and can cause tissue damage in organs prepared for transplant.

The terms "hypoxia" and "hypoxic" refer to an environment with levels of oxygen below normal. Hypoxia may be induced in cells by culturing the cells in a reduced oxygen environment, or cells may be treated with compounds that mimic hypoxia. Determining oxygen levels that define hypoxia in cell culture is well within the skill in the art.

The terms "hypoxic conditions" and "hypoxic disorders" include, but are not limited to, ischemic disorders (ischemic hypoxia) such as those listed above, wherein hypoxia results from reduced circulation; pulmonary disorders (hypoxic hypoxia) such as COPD, severe pneumonia, pulmonary edema, pulmonary hypertension, hyaline membrane disease, and the like, wherein hypoxia results from reduced oxygenation of the blood in the lungs; anemic disorders (anemic hypoxia) such as gastric or duodenal ulcers, liver or renal disease, thrombocytopenia or blood coagulation disorders, cancer or other chronic illness, cancer chemotherapy and other therapeutic interventions that produce anemia, and the like, wherein hypoxia results from a decreased concentration of hemoglobin or red blood cells; and altitude sickness, etc.

The terms "disorders" and "diseases" are used inclusively and refer to any condition deviating from normal. The terms "ischemic conditions" and "ischemic disorders" refer to any condition, disease, or disorder that is associated with ischemia. The terms "hypoxic conditions" and "hypoxic disorders" refer to any condition, disease, or disorder that is associated with hypoxia. Such ischemic and hypoxic disorders include, but are not limited to, those disorders described above.

The term "HIFα" refers to the alpha subunit of hypoxia inducible factor protein. HIFα may be any human or other mammalian protein, or fragment thereof, including, but not limited to, human HIF-1α (Genbank Accession No. Q16665), HIF-2α (Genbank Accession No. AAB41495), and HIF-3α (Genbank Accession No. AAD22668); murine HIF-1α (Genbank Accession No. Q61221), HIF-2α (Genbank Accession No. BAA20130 and AAB41496), and HIF-3α (Genbank Accession No. AAC72734); rat HIF-1α (Genbank Accession No. CAA70701), HIF-2α (Genbank Accession No. CAB96612), and HIF-3α (Genbank Accession No. CAB96611); and cow HIF-1α (Genbank Accession No. BAA78675). HIFα may also be any non-mammalian protein or fragment thereof, including *Xenopus laevis* HIF-1α (Genbank Accession No. CAB96628), *Drosophila melanogaster* HIF-1α (Genbank Accession No. JC4851), and chicken HIF-1α (Genbank Accession No. BAA34234). HIFα gene sequences may also be obtained by routine cloning techniques, for example, by using all or part of a HIFα gene sequence described above as a probe to recover and determine the sequence of a HIFα gene in another species.

Fragments of HIFα include the regions defined by human HIF-1α from amino acid 401 to 603 (Huang et al., supra), amino acid 531 to 575 (Jiang et al. (1997) J Biol Chem 272:19253-19260), amino acid 556 to 575 (Tanimoto et al., supra), amino acid 557 to 571 (Srinivas et al. (1999) Biochem Biophys Res Commun 260:557-561), and amino acid 556 to 575 (Ivan and Kaelin (2001) Science 292:464-468). Further, a fragment of HIFα includes any fragment containing at least one occurrence of the motif LXXLAP, e.g., as occurs in the HIF-1α native sequence at $L_{397}$TLLAP and $L_{559}$EMLAP. Additionally, a fragment of HIFα includes any fragment retaining at least one functional or structural characteristic of HIFα. For example, a HIF peptide for use in the screening assay of Example 7 may comprise [methoxycoumarin]-DLD-LEALAPYIPADDDFQL-amide (SEQ ID NO:5).

The terms "HIF prolyl hydroxylase" and "HIF PH" refer to any enzyme capable of hydroxylating a proline residue in the HIF protein. Preferably, the proline residue hydroxylated by HIF PH includes the proline found within the motif LXXLAP, e.g., as occurs in the human HIF-1α native sequence at L397TLLAP and L559EMLAP. HIF PH includes members of the Egl-Nine (EGLN) gene family described by Taylor (2001, Gene 275:125-132), and characterized by Aravind and Koonin (2001, Genome Biol 2:RESEARCH0007), Epstein et al. (2001, Cell 107:43-54), and Bruick and McKnight (2001, Science 294:1337 1340). Examples of HIF PH enzymes include human SM-20 (EGLN1) (GenBank Accession No. AAG33965; Dupuy et al. (2000) Genomics 69:348-54), EGLN2 isoform 1 (GenBank Accession No. CAC42510; Taylor, supra), EGLN2 isoform 2 (GenBank Accession No. NP_060025), and EGLN3 (GenBank Accession No. CAC42511; Taylor, supra); mouse EGLN1 (GenBank Accession No. CAC42515), EGLN2 (GenBank Accession No. CAC42511), and EGLN3 (SM-20) (GenBank Accession No. CAC42517); and rat SM-20 (GenBank Accession No. AAA19321). Additionally, HIF PH may include *Caenorhabditis elegans* EGL-9 (GenBank Accession No. AAD56365) and *Drosophila melanogaster* CG1114 gene product (GenBank Accession No. AAF52050). HIF PH also includes any fragment retaining at least one structural or functional feature of the foregoing full-length proteins, including a fragment having hydroxylase activity.

The terms "amino acid sequence" or "polypeptide" as used herein, e.g., to refer to HIFα and fragments thereof, or HIF PH and fragments thereof, contemplate an oligopeptide, peptide, or protein sequence, or to a fragment of any of these, and to naturally occurring or synthetic molecules. "Fragments" can refer to any portion of a sequence that retains at least one structural or functional characteristic of the protein. Immunogenic fragments or antigenic fragments are fragments of polypeptides, preferably, fragments of about five to fifteen amino acids in length, that retain at least one biological or immunological activity. Where "amino acid sequence" is used to refer to the polypeptide sequence of a naturally occurring protein molecule, "amino acid sequence" and like terms are not meant to limit the amino acid sequence to the complete native sequence associated with the recited protein molecule.

The term "related proteins" as used herein, for example, to refer to proteins related to HIFα prolyl hydroxylase, encompasses other 2-oxoglutarate dioxygenase enzymes, especially those family members that similarly require $Fe^{2+}$, 2-oxoglutarate, and oxygen to maintain hydroxylase activity. Such enzymes include, but are not limited to, e.g., procollagen lysyl hydroxylase, procollagen prolyl 4-hydroxylase, and Factor Inhibiting HIF (FIH), an asparaginyl hydroxylase responsible for regulating transactivation of HIFα. (GenBank Accession No. AAL27308; Mahon et al. (2001) Genes Dev 15:2675-2686; Lando et al. (2002) Science 295:858-861; and Lando et al. (2002) Genes Dev 16:1466-1471. See, also, Elkins et al. (2002) J Biol Chem C200644200.)

The term "agonist" refers to a molecule that increases or prolongs the duration of the effect of a particular molecule, e.g., an enzyme or protein, or a particular environment, e.g., hypoxia. Agonists may include proteins, nucleic acids, carbohydrates, or any other molecules that modulate the effects of the target molecule.

The term "antagonist" refers to a molecule which decreases the extent or duration of the effect of the biological or immunological activity of a particular molecule. Antagonists may include proteins, nucleic acids, carbohydrates, antibodies, or any other molecules that decrease the effect of the target molecule.

The term "microarray" refers to any arrangement of nucleic acids, amino acids, antibodies, etc., on a substrate. The substrate can be any suitable support, e.g., beads, glass, paper, nitrocellulose, nylon, or any appropriate membrane, etc. A substrate can be any rigid or semi-rigid support including, but not limited to, membranes, filters, wafers, chips, slides, fibers, beads, including magnetic or nonmagnetic beads, gels, tubing, plates, polymers, microparticles, capillaries, etc. The substrate can provide a surface for coating and/or can have a variety of surface forms, such as wells, pins, trenches, channels, and pores, to which the nucleic acids, amino acids, etc., may be bound.

The term "excipient" as used herein means an inert or inactive substance used in the production of pharmaceutical products or other tablets, including without limitation any substance used as a binder, disintegrant, coating, compression/encapsulation aid, cream or lotion, lubricant, parenteral, sweetener or flavoring, suspending/gelling agent, or wet granulation agent. Binders include, e.g., carbopol, povidone, xanthan gum, etc.; coatings include, e.g., cellulose acetate phthalate, ethylcellulose, gellan gum, maltodextrin, etc.; compression/encapsulation aids include, e.g., calcium carbonate, dextrose, fructose dc, honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams and lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; parenterals include, e.g., mannitol, povidone, etc.; plasticizers include, e.g., dibutyl sebacate, polyvinylacetate phthalate, etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

The term "sample" is used herein in its broadest sense. Samples may be derived from any source, for example, from bodily fluids, secretions, tissues, cells, or cells in culture including, but not limited to, saliva, blood, urine, serum, plasma, vitreous, synovial fluid, cerebral spinal fluid, amniotic fluid, and organ tissue (e.g., biopsied tissue); from chromosomes, organelles, or other membranes isolated from a cell; from genomic DNA, cDNA, RNA, mRNA, etc.; and from cleared cells or tissues, or blots or imprints from such cells or tissues. Samples may be derived from any source, such as, for example, a human subject, or a non-human mammalian subject, etc. Also contemplated are samples derived from any animal model of disease. A sample can be in solution or can be, for example, fixed or bound to a substrate. A sample can refer to any material suitable for testing for the presence of HIFα or of fragments of HIFα or suitable for screening for molecules that bind to HIFα or to fragments thereof. Methods for obtaining such samples are within the level of skill in the art.

The term "subject" is used herein in its broadest sense. Subjects may include isolated cells, either prokaryotic or eukaryotic, or tissues grown in culture. Preferably, subjects include animals, particularly a mammalian species including rat, rabbit, bovine, ovine, porcine, murine, equine, and primate, particularly human.

Invention

The present invention provides methods of stabilizing HIFα, to compounds that can be used in the methods, and to the use of the methods to prevent or treat disorders associated with HIF including, but not limited to, hypoxic and/or ischemic disorders such as those described above. The present invention further relates to the discovery that stabilization of the alpha subunit of hypoxia inducible factor (HIFα) is an effective therapeutic approach with unexpected benefits when applied to treatment or prevention of conditions associated with hypoxia and/or ischemia, e.g., myocardial infarction, stroke, occlusive arterial disease, angina pectoris, cardiac cirrhosis, atherosclerosis, etc.

The present invention contemplates methods of stabilizing HIF to augment angiogenesis, the response to acute hypoxia, and adaptation to chronic hypoxia. As tissue ischemia is a major cause of morbidity and mortality, the identification of methods that stabilize HIFα is beneficial in the treatment of hypoxic conditions. Further, the methods can be used to produce the beneficial effects of, e.g., a preconditioning hypoxic response, by stabilizing HIFα in a normoxic environment prior to an ischemic or hypoxic event. The methods can also be used to induce HIFα-specific effects, as described below, including therapeutic angiogenesis to restore blood flow to damaged tissues; neuroprotection to prevent, e.g., apoptotic loss of neurons associated with neurodegenerative diseases; and protection against oxidative damage produced by reactive oxygen species resulting from, e.g., reperfusion following an ischemic or hypoxic event.

When the methods of the invention are used to treat a disorder associated with ischemia and/or hypoxia, the disorder may be an acute ischemic disorder such as pulmonary, intestinal, cerebral, and/or myocardial infarction, or a chronic ischemic condition such as occlusive arterial disease, liver cirrhosis, congestive heart failure, etc. Further, the methods of the invention can be used to treat ischemia due to a transient or acute trauma, insult, or injury such as, e.g., a spinal cord injury, or to treat a patient diagnosed with, e.g., a pulmonary disorder such as pulmonary embolism and the like.

When the methods of the invention are used to prevent tissue damage caused by HIF-associated disorders including, but not limited to, ischemic and hypoxic disorders, treatment may be predicated on predisposing conditions, e.g., hypertension, diabetes, occlusive arterial disease, chronic venous insufficiency, Raynaud's disease, systemic sclerosis, cirrhosis, congestive heart failure, etc. Similarly, the methods of the invention can be used as a pretreatment to decrease or prevent the tissue damage caused by HIF-associated disorders including, but not limited to, ischemic and hypoxic disorders. The need for pretreatment may be based on a patient's history of recurring episodes of an ischemic condition, e.g., myocardial infarction or transient ischemic attacks; based on symptoms of impending ischemia, e.g., angina pectoris; or based on physical parameters implicating possible or likely ischemia or hypoxia, such as is the case with, e.g., individuals placed under general anesthesia or temporarily working at high altitudes. The methods may also be used in the context of organ transplants to pretreat organ donors and to maintain organs removed from the body prior to implantation in a recipient.

Presented herein is the discovery that stabilization of HIFα is modulated by proline hydroxylation and that HIFα stabilization is effective for treating or preventing the development or persistence of ischemic conditions such as DVT, angina pectoris, pulmonary embolism, stroke, myocardial infarction, etc. Specifically, it has been shown that HIF-1α and a HIF-1α peptide corresponding to residues 556 to 575 [HIF(556-575)] preincubated with rabbit reticulocyte lysate (RRL) bind specifically to the von Hippel Lindau protein (pVHL), and that such binding leads to the ubiquitination and degradation of HIF-1α. It has also been shown that mutation of the highly conserved colinear sequence $M_{561}LAPYIPM$ within HIF (556-575) to eight consecutive alanines stabilized HIF(556-575) under normoxic conditions. (Srinivas et al., supra.) An alanine scan of the region showed that mutation of $P_{564}$ to alanine in the context of full-length HIF-1α or a glutathione S-transferase (GST)-HIFα oxygen degradation domain (ODD) fusion protein (Gal4-ODD) abrogated pVHL-binding activity. The modification of $P_{564}$ was identified as an hydroxylation by electrospray ion trap tandem mass spectrometry (MS/MS), and by thin layer chromatography of Gal4-HIF(555-575) that was in vitro translated using RRL in the presence of [$^3$H]proline. The functional significance of the proline hydroxylation was demonstrated by showing that $P_{564}$-hydroxylated HIFα bound pVHL, while HIF-1α mutant containing a single point mutation of $P_{564}$ to alanine was stable in COS7 cells and was insensitive to the hypoxia mimetic desferrioxamine. (See Ivan and Kaelin, supra; Jaakkola et al. (2001) Science 292:468-472.)

As HIFα is modified by proline hydroxylation, a reaction requiring oxygen and $Fe^{2+}$, the present invention contemplates in one aspect that the enzyme responsible for HIFα hydroxylation is a member of the 2-oxoglutarate dioxygenase family. Such enzymes include, but are not limited to, procollagen lysyl hydroxylase, procollagen prolyl 3-hydroxylase, procollagen prolyl 4-hydroxylase α(I) and α(II), thymine 7-hydroxylase, aspartyl (asparaginyl) β-hydroxylase, ε-N-trimethyllysine hydroxylase, and γ-butyrobetaine hydroxylase, etc. These enzymes require oxygen, $Fe^{2+}$, 2-oxoglutarate, and ascorbic acid for their hydroxylase activity. (See, e.g., Majamaa et al. (1985) Biochem J 229:127-133; Myllyharju and Kivirikko (1997) EMBO J. 16:1173-1180; Thornburg et al. (1993) 32:14023-14033; and Jia et al. (1994) Proc Natl Acad Sci USA 91:7227-7231.)

Several small molecule inhibitors of prolyl 4-hydroxylase have been identified. (See, e.g., Majamaa et al., supra; Kivirikko and Myllyharju (1998) Matrix Biol 16:357-368; Bickel et al. (1998) Hepatology 28:404-411; Friedman et al. (2000) Proc Natl Acad Sci USA 97:4736-4741; and Franklin et al. (2001) Biochem J 353:333-338; all incorporated by reference herein in their entirety.) The present invention contemplates the use of these compounds in the methods provided herein.

Compounds that can be used in the methods of the invention include, for example, structural mimetics of 2-oxoglutarate. Such compounds may inhibit the target 2-oxoglutarate dioxygenase enzyme family member competitively with respect to 2-oxoglutarate and noncompetitively with respect to iron. (Majamaa et al. (1984) Eur J Biochem 138:239-245; and Majamaa et al., supra.)

In certain embodiments, compounds used in the methods of the invention are selected from a compound of the formula (I)

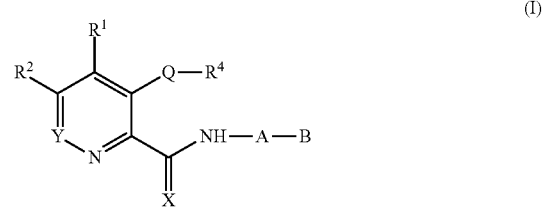

wherein
A is 1,2-arylidene, 1,3-arylidene, 1,4-arylidene; or $(C_1-C_4)$-alkylene, optionally substituted by one or two halogen, cyano, nitro, trifluoromethyl, $(C_1-C_6)$-alkyl, $(C_1-C_6)$-hydroxyalkyl, $(C_1-C_6)$-alkoxy, —O—$[CH_2]_x$—$C_fH_{(2f+1-g)}$Hal$_g$, $(C_1-C_6)$-fluoroalkoxy, $(C_1-C_8)$-fluoroalkenyloxy, $(C_1-C_8)$-fluoroalkynyloxy, —OCF$_2$Cl, —O—CF$_2$—CHFCl; $(C_1-C_6)$-allylmercapto, $(C_1-C_6)$-alkylsulfinyl, $(C_1-C_6)$-alkylsulfonyl, $(C_1-C_6)$-alkylcarbonyl, $(C_1-C_6)$-alkoxycarbonyl, carbamoyl, N—$(C_1-C_4)$-alkylcarbamoyl, N,N-di-$(C_1-C_4)$-alkylcarbamoyl, $(C_1-C_6)$-alkylcarbonyloxy, $(C_3-C_8)$-cycloalkyl, phenyl, benzyl, phenoxy, benzyloxy, anilino, N-methylanilino, phenylmercapto, phenylsulfonyl, phenylsulfinyl, sulfamoyl, N—$(C_1-C_4)$-allylsulfamoyl, N,N-di-$(C_1-C_4)$-alkylsulfamoyl; or by a substituted $(C_6-C_{12})$-aryloxy, $(C_7-C_{11})$-aralkyloxy, $(C_6-C_{12})$-aryl, $(C_7-C_{11})$-aralkyl radical, which carries in the aryl moiety one to five identical or different substituents selected from halogen, cyano, nitro, trifluoromethyl, $(C_1-C_6)$-alkyl, $(C_1-C_6)$-alkoxy, —O—$[CH_2]_x$—$C_fH_{(2f+1-g)}$Hal$_g$, —OCF$_2$Cl, —O—CF$_2$—CHFCl, $(C_1-C_6)$-alkylmercapto, $(C_1-C_6)$-alkylsulfinyl, $(C_1-C_6)$-alkylsulfonyl, $(C_1-C_6)$-alkylcarbonyl, $(C_1-C_6)$-alkoxycarbonyl, carbamoyl, N—$(C_1-C_4)$-alkylcarbamoyl, N,N-di-$(C_1-C_4)$-alkylcarbamoyl, $(C_1-C_6)$-alkylcarbonyloxy, $(C_3-C_8)$-cycloalkyl, sulfamoyl, N—$(C_1-C_4)$-alkylsulfamoyl, N,N-di-$(C_1-C_4)$-alkylsulfamoyl; or wherein A is —$CR^5R^6$ and $R^5$ and $R^6$ are each independently selected from hydrogen, $(C_1-C_6)$-alkyl, $(C_3-C_7)$-cycloalkyl, aryl, or a substituent of the α-carbon atom of an α-amino acid, wherein the amino acid is a natural L-amino acid or its D-isomer.

B is —$CO_2H$, —$NH_2$, —$NHSO_2CF_3$, tetrazolyl, imidazolyl, 3-hydroxyisoxazolyl, —CONHCOR''', —CONHSOR''', —$CONHSO_2R'''$, where R''' is aryl, heteroaryl, ($C_3$-$C_7$)-cycloalkyl, or ($C_1$-$C_4$)-alkyl, optionally monosubstituted by ($C_6$-$C_{12}$)-aryl, heteroaryl, OH, SH, ($C_1$-$C_4$)-alkyl, ($C_1$-$C_4$)-alkoxy, ($C_1$-$C_4$)-thioalkyl, ($C_1$-$C_4$)-sulfinyl, ($C_1$-$C_4$)-sulfonyl, $CF_3$, Cl, Br, F, I, NO2, —COOH, ($C_2$-$C_5$)-alkoxycarbonyl, $NH_2$, mono-($C_1$-$C_4$-alkyl)-amino, di-($C_1$-$C_4$-alkyl)-amino, or ($C_1$-$C_4$)-perfluoroalkyl; or wherein B is a $CO_2$-G carboxyl radical, where G is a radical of an alcohol G-OH in which G is selected from ($C_1$-$C_{20}$)-alkyl radical, ($C_3$-$C_8$) cycloalkyl radical, ($C_2$-$C_{20}$)-alkenyl radical, ($C_3$-$C_8$)-cycloalkenyl radical, retinyl radical, ($C_2$-$C_{20}$)-alkynyl radical, ($C_4$-$C_{20}$)-alkenynyl radical, where the alkenyl, cycloalkenyl, alkynyl, and alkenynyl radicals contain one or more multiple bonds; ($C_6$-$C_{16}$)-carbocyclic aryl radical, ($C_7$-$C_{16}$)-carbocyclic aralkyl radical, heteroaryl radical, or heteroaralkyl radical, wherein a heteroaryl radical or heteroaryl moiety of a heteroaralkyl radical contains 5 or 6 ring atoms; and wherein radicals defined for G are substituted by one or more hydroxyl, halogen, cyano, trifluoromethyl, nitro, carboxyl, ($C_1$-$C_{12}$)-alkyl, ($C_3$-$C_8$)-cycloalkyl, ($C_5$-$C_8$)-cycloalkenyl, ($C_6$-$C_{12}$)-aryl, ($C_7$-$C_{16}$)-aralkyl, ($C_2$-$C_{12}$)-alkenyl, ($C_2$-$C_{12}$)-alkynyl, ($C_1$-$C_{12}$)-alkoxy, ($C_1$-$C_{12}$)-alkoxy-($C_1$-$C_{12}$)-alkyl, ($C_1$-$C_{12}$)-alkoxy-($C_1$-$C_{12}$)-alkoxy, ($C_6$-$C_{12}$)-aryloxy, ($C_7$-$C_{16}$)-aralkyloxy, ($C_1$-$C_8$)-hydroxyalkyl, —O—$[CH_2]_x$—$C_fH_{(2f+1-g)}$—$F_g$, —$OCF_2Cl$, —$OCF_2$—CHFCl, ($C_1$-$C_{12}$)-alkylcarbonyl, ($C_3$-$C_8$)-cycloalkylcarbonyl, ($C_6$-$C_{12}$)-arylcarbonyl, ($C_7$-$C_{16}$)-aralkylcarbonyl, cinnamoyl, ($C_2$-$C_{12}$)-alkenylcarbonyl, ($C_2$-$C_{12}$)-alkynylcarbonyl, ($C_1$-$C_{12}$)-alkoxycarbonyl, ($C_1$-$C_{12}$)-alkoxy-($C_1$-$C_{12}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{12}$)-alkenyloxycarbonyl, ($C_2$-$C_{12}$)-alkynyloxycarbonyl, acyloxy, ($C_1$-$C_{12}$)-alkoxycarbonyloxy, ($C_1$-$C_{12}$)-alkoxy-($C_1$-$C_{12}$)-alkoxycarbonyloxy, ($C_6$-$C_{12}$)-aryloxycarbonyloxy, ($C_7$-$C_{16}$) aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxycarbonyloxy, carbamoyl, N—($C_1$-$C_{12}$)-allylcarbamoyl, N,N-di($C_1$-$C_{12}$)-alkylcarbamoyl, N—($C_3$-$C_8$)-cycloalkyl-carbamoyl, N—($C_6$-$C_{16}$)-arylcarbamoyl, N—($C_7$-$C_{16}$)-aralkylcarbamoyl, N—($C_1$-$C_{10}$)-alkyl-N—($C_6$-$C_{16}$)-arylcarbamoyl, N—($C_1$-$C_{10}$)-alkyl-N—($C_7$-$C_{16}$)-aralkylcarbamoyl, N—(($C_1$-$C_{10}$)-alkoxy-($C_1$-$C_{10}$)-alkyl)-carbamoyl, N—(($C_6$-$C_{12}$)-aryloxy-($C_1$-$C_{10}$)alkyl)-carbamoyl, N—(($C_7$-$C_{16}$)-aralkyloxy-($C_1$-$C_{10}$)-alkyl)-carbamoyl, N—($C_1$-$C_{10}$)-alkyl-N—(($C_1$-$C_{10}$)-alkoxy-($C_1$-$C_{10}$)-alkyl)-carbamoyl, N—($C_1$-$C_{10}$)-alkyl-N—(($C_6$-$C_{16}$)-aryloxy-($C_1$-$C_{10}$)-alkyl)-carbamoyl, N—($C_1$-$C_{10}$)-alkyl-N—(($C_7$-$C_{16}$)-aralkyloxy-($C_1$-$C_{10}$)-alkyl)-carbamoyl, carbamoyloxy, N—($C_1$-$C_{12}$)-alkylcarbamoyloxy, N,N-di-($C_1$-$C_{12}$)-alkylcarbamoyloxy, N—($C_3$-$C_8$)-cycloalkylcarbamoyloxy, N—($C_6$-$C_{12}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N($C_1$-$C_{10}$)-alkyl-N—($C_7$-$C_{16}$)-aralkylcarbamoyloxy, N—(($C_1$-$C_{10}$)-alkyl)-carbamoyloxy, N—(($C_6$-$C_{12}$)-aryloxy-($C_1$-$C_{10}$)-alkyl)-carbamoyloxy, N—(($C_7$-$C_{16}$)-aralkyloxy-($C_1$-$C_{10}$)-alkyl)-carbamoyloxy, N—($C_1$-$C_{10}$)-alkyl-N—(($C_1$-$C_{10}$)-alkoxy-($C_1$-$C_{10}$)-alkyl)-carbamoyloxy, N—($C_1$-$C_{10}$)-alkyl-N—(($C_6$-$C_{12}$)-aryloxy-($C_1$-$C_{10}$)-alkyl)-carbamoyloxy, N—($C_1$-$C_{10}$)-alkyl-N—(($C_7$-$C_{16}$)-aralkyloxy-($C_1$-$C_{10}$)-alkyl)-carbamoyloxy, amino, ($C_1$-$C_{12}$)-alkylamino, di-($C_1$-$C_{12}$)-alkylamino, ($C_3$-$C_8$)-cycloalkylamino, ($C_2$-$C_{12}$)-alkenylamino, ($C_2$-$C_{12}$)-alkynylamino, N—($C_6$-$C_{12}$)-arylamino, N—($C_7$-$C_{11}$)-aralkylamino, N-alkyl-aralkylamino, N-alkyl-arylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkylcarbonylamino, ($C_3$-$C_8$)-cycloalkylcarbonylamino, ($C_6$-$C_{12}$) arylcarbonylamino, ($C_7$-$C_{16}$)-aralkylcarbonylamino, ($C_1$-$C_{12}$)-alkylcarbonyl-N—($C_1$-$C_{10}$)-alkylamino, ($C_3$-$C_8$)-cycloalkylcarbonyl-N—($C_1$-$C_{10}$)-alkylamino, ($C_6$-$C_{12}$)-arylcarbonyl-N—($C_1$-$C_{10}$)allylamino, ($C_7$-$C_{11}$)-aralkylcarbonyl-N—($C_1$-$C_{10}$)-alkylamino, ($C_1$-$C_{12}$)-alkylcarbonylamino-($C_1$-$C_8$)-alkyl, ($C_3$-$C_8$)-cycloalkylcarbonylamino-($C_1$-$C_8$)alkyl, ($C_6$-$C_{12}$)-arylcarbonylamino-($C_1$-$C_8$)-alkyl, ($C_7$-$C_{12}$)-aralkylcarbonylamino($C_1$-$C_8$)-alkyl, amino-($C_1$-$C_{10}$)-alkyl, N—($C_1$-$C_{10}$) alkylamino-($C_1$-$C_{10}$)-alkyl, N,N-di-($C_1$-$C_{10}$)-alkylamino-($C_1$-$C_{10}$)-alkyl, ($C_3$-$C_8$)-cycloalkylamino-($C_1$-$C_{10}$)-alkyl, ($C_1$-$C_{12}$)-alkylmercapto, ($C_1$-$C_{12}$)-alkylsulfinyl, ($C_1$-$C_{12}$)-alkylsulfonyl, ($C_6$-$C_{16}$)-arylmercapto, ($C_6$-$C_{16}$)-arylsulfinyl, ($C_6$-$C_{12}$)-arylsulfonyl, ($C_7$-$C_{16}$)-aralkylmercapto, ($C_7$-$C_{16}$)-aralkylsulfinyl, ($C_7$-$C_{16}$)-aralkylsulfonyl, sulfamoyl, N—($C_1$-$C_{10}$)-alkylsulfamoyl, N,N-di($C_1$-$C_{10}$)-alkylsulfamoyl, ($C_3$-$C_8$)-cycloalkylsulfamoyl, N—($C_6$-$C_{12}$)-alkylsulfamoyl, N—($C_7$-$C_{16}$)-aralkylsulfamoyl, N—($C_1$-$C_{10}$)-alkyl-N—($C_6$-$C_{12}$)-arylsulfamoyl, N—($C_1$-$C_{10}$)-alkyl-N—($C_7$-$C_{16}$)-aralkylsulfamoyl, ($C_1$-$C_{10}$)-alkylsulfonamido, N—($C_1$-$C_{10}$)-alkyl)-($C_1$-$C_{10}$)-alkylsulfonamido, ($C_7$-$C_{16}$)-aralkylsulfonamido, or N—(($C_1$-$C_{10}$)-alkyl-($C_7$-$C_{16}$)-aralkylsulfonamido; wherein radicals which are aryl or contain an aryl moiety, may be substituted on the aryl by one to five identical or different hydroxyl, halogen, cyano, trifluoromethyl, nitro, carboxyl, ($C_1$-$C_{12}$)-alkyl, ($C_3$-$C_8$)-cycloalkyl, ($C_6$-$C_{12}$)-aryl, ($C_7$-$C_{16}$)-aralkyl, ($C_1$-$C_{12}$)-alkoxy, ($C_1$-$C_{12}$)-alkoxy-($C_1$-$C_{12}$)alkyl, ($C_1$-$C_{12}$)-alkoxy-($C_1$-$C_{12}$) alkoxy, ($C_6$-$C_{12}$)-aryloxy, ($C_7$-$C_{16}$)-aralkyloxy, ($C_1$-$C_8$)-hydroxyalkyl, ($C_1$-$C_{12}$)-alkylcarbonyl, ($C_3$-$C_8$)-cycloalkyl-carbonyl, ($C_6$-$C_{12}$)-arylcarbonyl, ($C_7$-$C_{16}$) aralkylcarbonyl, ($C_1$-$C_{12}$)-alkoxycarbonyl, ($C_1$-$C_{12}$)-alkoxy-($C_1$-$C_{12}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{12}$)-alkenyloxycarbonyl, ($C_2$-$C_{12}$)-alkynyloxycarbonyl, ($C_1$-$C_{12}$)-alkylcarbonyloxy, ($C_3$-$C_8$)-cycloalkylcarbonyloxy, ($C_6$-$C_{12}$)-arylcarbonyloxy, ($C_7$-$C_{16}$)-aralkylcarbonyloxy, cinnamoyloxy, ($C_2$-$C_{12}$)-alkenylcarbonyloxy, ($C_2$-$C_{12}$)-alkynylcarbonyloxy, ($C_1$-$C_{12}$)-alkoxycarbonyloxy, ($C_1$-$C_{12}$)-alkoxy-($C_1$-$C_{12}$)-alkoxycarbonyloxy, ($C_6$-$C_{12}$)-aryloxycarbonyloxy, ($C_7$-$C_{16}$)-aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxycarbonyloxy, carbamoyl, N—($C_1$-$C_{12}$)-alkylcarbamoyl, N,N-di-($C_1$-$C_{12}$)-alkylcarbamoyl, N—($C_3$-$C_8$)-cycloalkylcarbamoyl, N—($C_6$-$C_{12}$)-arylcarbamoyl, N—($C_7$-$C_{16}$)-aralkylcarbamoyl, N—($C_1$-$C_{10}$)-alkyl-N—($C_6$-$C_{12}$)-arylcarbamoyl, N—($C_1$-$C_{10}$)-alkyl-N—($C_7$-$C_{16}$)-aralkylcarbamoyl, N—(($C_1$-$C_{10}$)-alkoxy-($C_1$-$C_{10}$)-alkyl)-carbamoyl, N—(($C_6$-$C_{12}$)-aryloxy-($C_1$-$C_{10}$)-alkyl)-carbamoyl, N—(($C_7$-$C_{16}$)-aralkyloxy-($C_1$-$C_{10}$)-alkyl)-carbamoyl, N—($C_1$-$C_{10}$)-alkyl-N—(($C_1$-$C_{10}$)-alkoxy-($C_1$-$C_{10}$)-alkyl)-carbamoyl, N—($C_1$-$C_{10}$)-alkyl-N—(($C_6$-$C_{12}$)-aryloxy-($C_1$-$C_{10}$)-alkyl)-carbamoyl, N—($C_1$-$C_{10}$)-alkyl-N—(($C_7$-$C_{16}$)-aralkyloxy-($C_1$-$C_{10}$)-alkyl)-carbamoyl, carbamoyloxy, N—($C_1$-$C_{12}$)-alkylcarbamoyloxy, N,N-di-($C_1$-$C_{12}$)-alkylcarbamoyloxy, N—($C_3$-$C_8$)-cycloalkylcarbamoyloxy, N—($C_6$-$C_{12}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N($C_1$-$C_{10}$)-alkyl-N—($C_7$-$C_{16}$)-aralkylcarbamoyloxy, N—(($C_1$-$C_{10}$)-alkyl)-carbamoyloxy, N—(($C_6$-$C_{12}$)-aryloxy-($C_1$-$C_{10}$)-alkyl)-carbamoyloxy, N—(($C_7$-$C_{16}$)-aralkyloxy-($C_1$-$C_{10}$)-alkyl)-carbamoyloxy, N—($C_1$-$C_{10}$)-alkyl-N—(($C_1$-$C_{10}$)-alkoxy-($C_1$-$C_{10}$)-alkyl)-carbamoyloxy, N—($C_1$-$C_{10}$)-alkyl-N—(($C_6$-$C_{12}$)-aryloxy- ($C_1$-$C_{10}$)-alkyl)-carbamoyloxy, N—($C_1$-$C_{10}$)-alkyl-N—(($C_7$-$C_{16}$)-aralkyloxy-($C_1$-$C_{10}$)-alkyl)-carbamoyloxy, amino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_{12}$)-alkynylamino, N—($C_6$-$C_{12}$)-arylamino, N—($C_7$-$C_{11}$)-aralkylamino, N-alkylaralkylamino, N-alkyl-arylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkylcarbonylamino, ($C_3$-$C_8$)-cycloalkylcarbonylamino, ($C_6$-$C_{12}$)-arylcarbonylamino, ($C_7$-$C_{16}$)-alkylcarbonylamino, ($C_1$-$C_{12}$)-alkylcarbonyl-N—($C_1$-$C_{10}$)-alkylamino, ($C_3$-$C_8$)-cycloalkylcarbonyl-N—($C_1$-$C_{10}$)-alkylamino, ($C_6$-$C_{12}$)-arylcarbonyl-N—($C_1$-$C_{10}$)-alkylamino, ($C_7$-$C_{11}$)-aralkylcarbonyl-N—($C_1$-$C_{10}$)-alkylamino, ($C_1$-$C_{12}$)-alkylcarbonylamino-($C_1$-$C_8$)-alkyl, ($C_3$-$C_8$)-cycloalkylcarbonylamino-($C_1$-$C_8$)-alkyl, ($C_6$-$C_{12}$)-arylcarbonylamino-($C_1$-$C_8$)-alkyl, ($C_7$-$C_{16}$)-aralkylcarbonylamino-($C_1$-$C_8$)-alkyl, amino-($C_1$-$C_{10}$)-alkyl, N—($C_1$-$C_{10}$)-alkylamino-($C_1$-$C_{10}$)alkyl, N,N-di-($C_1$-$C_{10}$)-alkylamino-($C_1$-$C_{10}$)-alkyl, ($C_3$-$C_8$)-cycloalkylamino-($C_1$-$C_{10}$)-alkyl, ($C_1$-$C_{12}$)-alkylmercapto, ($C_1$-$C_{12}$)-alkylsulfinyl, ($C_1$-$C_{12}$)-alkylsulfonyl, ($C_6$-$C_{12}$)-arylmercapto, ($C_6$-$C_{12}$)-arylsulfinyl, ($C_6$-$C_{12}$)-arylsulfonyl, ($C_7$-$C_{16}$)-aralkylmercapto, ($C_7$-$C_{16}$)-aralkylsulfinyl, or ($C_7$-$C_{16}$)-aralkylsulfonyl;

X is O or S;

Q is O, S, NR', or a bond;

where, if Q is a bond, $R^4$ is halogen, nitrile, or trifluoromethyl; or where, if Q is O, S, or NR', $R^4$ is hydrogen, ($C_1$-$C_{10}$)-alkyl radical, ($C_2$-$C_{10}$)-alkenyl radical, ($C_2$-$C_{10}$)-alkynyl radical, wherein alkenyl or alkynyl radical contains one or two C—C multiple bonds; unsubstituted fluoroalkyl radical of the formula —$[CH_2]_x$—$C_fH_{(2f+1-g)}$—$F_g$, ($C_1$-$C_8$)-alkoxy-($C_1$-$C_6$)-alkyl radical, ($C_1$-$C_6$)-alkoxy-($C_1$-$C_4$)-alkoxy-($C_1$-$C_4$)-alkyl radical, aryl radical, heteroaryl radical, ($C_7$-$C_{11}$)-aralkyl radical, or a radical of the formula Z

$$—[CH_2]_v—[O]_w—[CH_2]_t-E \quad (Z)$$

where

E is a heteroaryl radical, a ($C_3$-$C_8$)-cycloalkyl radical, or a phenyl radical of the formula F

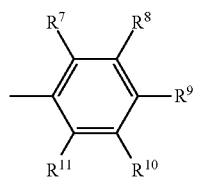

(F)

v is 0-6, w is 0 or 1, t is 0-3, and $R^7$, $R^8$, $R^9$, $R^{10}$, and $R^{11}$ are identical or different and are hydrogen, halogen, cyano, nitro, trifluoromethyl, ($C_1$-$C_6$)-alkyl, ($C_3$-$C_8$)-cycloalkyl, ($C_1$-$C_6$)-alkoxy, —O—$[CH_2]_x$—$C_fH_{(2f+1-g)}$—$F_g$, —$OCF_2$—Cl, —O—$CF_2$—CHFCl, ($C_1$-$C_6$)-alkylmercapto, ($C_1$-$C_6$)-hydroxyalkyl, ($C_1$-$C_6$)-alkoxy-($C_1$-$C_6$)-alkoxy, ($C_1$-$C_6$)-alkoxy-($C_1$-$C_6$)-alkyl, ($C_1$-$C_6$)-alkylsulfinyl, ($C_1$-$C_6$)-alkylsulfonyl, ($C_1$-$C_6$)-alkylcarbonyl, ($C_1$-$C_8$)-alkoxycarbonyl, carbamoyl, N—($C_1$-$C_8$)-alkylcarbamoyl, N,N-di-($C_1$-$C_8$)-alkylcarbamoyl, or ($C_7$-$C_{11}$)-aralkylcarbamoyl, optionally substituted by fluorine, chlorine, bromine, trifluoromethyl, ($C_1$-$C_6$)-alkoxy, N—($C_3$-$C_8$)-cycloalkylcarbamoyl, N—($C_3$-$C_8$)-cycloalkyl-($C_1$-$C_4$)-alkylcarbamoyl, ($C_1$-$C_6$)-alkylcarbonyloxy, phenyl, benzyl, phenoxy, benzyloxy, $NR^yR^z$ wherein $R^y$ and $R^z$ are independently selected from hydrogen, ($C_1$-$C_{12}$)-alkyl, ($C_1$-$C_8$)-alkoxy-($C_1$-$C_8$)-alkyl, ($C_7$-$C_{12}$)-aralkoxy-($C_1$-$C_8$)-alkyl, ($C_6$-$C_{12}$)-aryloxy-($C_1$-$C_8$)-alkyl, ($C_3$-$C_{10}$)-cycloalkyl, ($C_3$-$C_{12}$)-alkenyl, ($C_3$-$C_{12}$)-alkynyl, ($C_6$-$C_{12}$)-aryl, ($C_7$-$C_{11}$)-aralkyl, ($C_1$-$C_{12}$)-alkoxy, ($C_7$-$C_{12}$)aralkoxy, ($C_1$-$C_{12}$)-alkylcarbonyl, ($C_3$-$C_8$)-cycloalkylcarbonyl, ($C_6$-$C_{12}$)-arylcarbonyl, ($C_7$-$C_{16}$)-aralkylcarbonyl; or further wherein $R^y$ and $R^z$ together are —$[CH2]_n$—, in which a $CH_2$ group can be replaced by O, S, N—($C_1$-$C_4$)-alkylcarbonylimino, or N—($C_1$-$C_4$)-alkoxycarbonylimino; phenylmercapto, phenylsulfonyl, phenylsulfinyl, sulfamoyl, N—($C_1$-$C_8$)-allylsulfamoyl, or N,N-di-($C_1$-$C_8$)-alkylsulfamoyl; or alternatively $R^7$ and $R^8$, $R^8$ and $R^9$, $R^9$ and $R^{10}$, or $R^{10}$ and $R^{11}$, together are a chain selected from —$[CH_2]_n$— or —CH=CH—CH=CH—, where a $CH_2$ group of the chain is optionally replaced by O, S, SO, $SO_2$, or $NR^Y$; and n is 3, 4, or 5; and if E is a heteroaryl radical, said radical can carry 1-3 substituents selected from those defined for $R^7$-$R^{11}$, or if E is a cycloalkyl radical, the radical can carry one substituent selected from those defined for $R^7$-$R^{11}$;

or where, if Q is NR', $R^4$ is alternatively R", where R' and R" are identical or different and are hydrogen, ($C_6$-$C_{12}$)-aryl, ($C_7$-$C_{11}$)-aralkyl, ($C_1$-$C_8$)-alkyl, ($C_1$-$C_8$)-alkoxy-($C_1$-$C_8$)-alkyl, ($C_7$-$C_{12}$)-aralkoxy-($C_1$-$C_8$)-alkyl, ($C_6$-$C_{12}$)-aryloxy-($C_1$-$C_8$)-alkyl, ($C_1$-$C_{10}$)-alkylcarbonyl, optionally substituted ($C_7$-$C_{16}$)-aralkylcarbonyl, or optionally substituted $C_6$-$C_{12}$)-arylcarbonyl; or R' and R" together are —$[CH_2]_n$, in which a $CH_2$ group can be replaced by O, S, N-acylimino, or N—($C_1$-$C_{10}$)-alkoxycarbonylimino, and h is 3 to 7.

Y is N or $CR^3$;

$R^1$, $R^2$ and $R^3$ are identical or different and are hydrogen, hydroxyl, halogen, cyano, trifluoromethyl, nitro, carboxyl, ($C_1$-$C_{20}$)-alkyl, ($C_3$-$C_8$)-cycloalkyl, ($C_3$-$C_8$)cycloalkyl-($C_1$-$C_{12}$)-alkyl, ($C_3$-$C_8$)-cycloalkoxy, ($C_3$-$C_8$)-cycloalkyl-($C_1$-$C_{12}$)-alkoxy, ($C_3$-$C_8$)-cycloalkyloxy-($C_1$-$C_{12}$)-alkyl, ($C_3$-$C_8$)-cycloalkyloxy-($C_1$-$C_{12}$)-alkoxy, ($C_3$-$C_8$)-cycloalkyl-($C_1$-$C_8$)-alkyl-($C_1$-$C_6$)-alkoxy, ($C_3$-$C_8$)-cycloalkyl-($C_1$-$C_8$)-alkoxy-($C_1$-$C_6$)-alkyl, ($C_3$-$C_8$)-cycloalkyloxy-($C_1$-$C_8$)-alkoxy-($C_1$-$C_6$)-alkyl, ($C_3$-$C_8$)cycloalkoxy-($C_1$-$C_8$)-alkoxy-($C_1$-$C_8$)-alkoxy, ($C_6$-$C_{12}$)-aryl, ($C_7$-$C_{16}$)-aralkyl, ($C_7$-$C_{16}$)-aralkenyl, ($C_7$-$C_{16}$)-aralkynyl, ($C_2$-$C_{20}$)-alkenyl, ($C_2$-$C_{20}$)-alkynyl, ($C_1$-$C_{20}$)-alkoxy, ($C_2$-$C_{20}$)-alkenyloxy, ($C_2$-$C_{20}$)-alkynyloxy, retinyloxy, ($C_1$-$C_{20}$)-alkoxy-($C_1$-$C_{12}$)-alkyl, ($C_1$-$C_{12}$)-alkoxy-($C_1$-$C_{12}$)-alkoxy, ($C_1$-$C_{12}$)alkoxy-($C_1$-$C_8$)-alkoxy-($C_1$-$C_8$)-alkyl, ($C_6$-$C_{12}$)-aryloxy, ($C_7$-$C_{16}$)-aralkyloxy, ($C_6$-$C_{12}$)-aryloxy($C_1$-$C_6$)-alkoxy, ($C_7$-$C_{16}$)-aralkoxy-($C_1$-$C_6$)-alkoxy, ($C_1$-$C_{16}$)-hydroxyalkyl, ($C_6$-$C_{16}$)-aryloxy-($C_1$-$C_8$)-alkyl, ($C_7$-$C_{16}$)-aralkoxy-($C_1$-$C_8$)-alkyl, ($C_6$-$C_{12}$)-aryloxy-($C_1$-$C_8$)-alkoxy-($C_1$-$C_6$)-alkyl, ($C_7$-$C_{12}$)-aralkyloxy-($C_1$-$C_8$)-alkoxy-($C_1$-$C_6$)-alkyl, ($C_2$-$C_{20}$)-alkenyloxy-($C_1$-$C_6$)-alkyl, ($C_2$-$C_{20}$)-alkynyloxy-($C_1$-$C_6$)-alkyl, retinyloxy-($C_1$-$C_6$)-alkyl, —O—$[CH_2]_xC_fH_{(2f+1-g)}F_g$, —$OCF_2$Cl, —$OCF_2$—CHFCl, ($C_1$-$C_{20}$)-alkylcarbonyl, ($C_3$-$C_8$)-cycloalkylcarbonyl, ($C_6$-$C_{12}$)-arylcarbonyl, ($C_7$-$C_{16}$)-aralkylcarbonyl, cinnamoyl, ($C_2$-$C_{20}$)-alkenylcarbonyl, ($C_2$-$C_{20}$)-alkynylcarbonyl, ($C_1$-$C_{20}$)-alkoxycarbonyl, ($C_1$-$C_{12}$)-alkoxy-($C_1$-$C_{12}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{20}$)-alkenyloxycarbonyl, retinyloxycarbonyl, ($C_2$-$C_{20}$)-alkynyloxycarbonyl, ($C_6$-$C_{12}$)-aryloxy-($C_1$-$C_6$)-alkoxycarbonyl, ($C_7$-$C_{16}$)-aralkoxy-($C_1$-$C_6$)-alkoxycarbonyl, ($C_3$-$C_8$)cycloalkyl-($C_1$-$C_6$)-alkoxycarbonyl, ($C_3$-$C_8$)-cycloalkoxy-($C_1$-$C_6$)-alkoxycarbonyl, ($C_1$-$C_{12}$)-alkylcarbonyloxy, ($C_3$-$C_8$)-cycloalkylcarbonyloxy, ($C_6$-$C_{12}$)-arylcarbonyloxy, ($C_7$-$C_{16}$)-aralkylcarbonyloxy, cinnamoyloxy, ($C_2$-$C_{12}$)-alkenylcarbonyloxy, ($C_2$-$C_{12}$)-alkynylcarbonyloxy, ($C_1$-$C_{12}$)-alkoxycarbonyloxy, ($C_1$-$C_{12}$)- alkoxy-$(C_1$-$C_{12})$-alkoxycarbonyloxy, $(C_6$-$C_{12})$-aryloxycarbonyloxy, $(C_7$-$C_{16})$-aralkyloxycarbonyloxy, $(C_3$-$C_8)$-cycloalkoxycarbonyloxy, $(C_2$-$C_{12})$-alkenyloxycarbonyloxy, $(C_2$-$C_{12})$-alkynyloxycarbonyloxy, carbamoyl, N—$(C_1$-$C_{12})$-allylcarbamoyl, N,N-di-$(C_1$-$C_{12})$-alkylcarbamoyl, N—$(C_3$-$C_8)$-cycloalkylcarbamoyl, N,N-dicyclo-$(C_3$-$C_8)$-alkylcarbamoyl, N—$(C_1$-$C_{10})$-alkyl-N—$(C_3$-$C_8)$-cycloalkylcarbamoyl, N—$((C_3$-$C_8)$-cycloalkyl-$(C_1$-$C_6)$-alkyl)-carbamoyl, N—$(C_1$-$C_6)$-alkyl-N—$((C_3$-$C_8)$-cycloalkyl-$(C_1$-$C_6)$-alkyl)-carbamoyl, N-(+)-dehydroabietylcarbamoyl, N—$(C_1$-$C_6)$-alkyl-N-(+)-dehydroabietylcarbamoyl, N—$(C_6$-$C_{12})$-arylcarbamoyl, N—$(C_7$-$C_{16})$-aralkylcarbamoyl, N—$(C_1$-$C_{10})$-alkyl-N—$(C_6$-$C_{16})$-arylcarbamoyl, N—$(C_1$-$C_{10})$-alkyl-N—$(C_7$-$C_{16})$-aralkylcarbamoyl, N—$((C_1$-$C_{18})$-alkoxy-$(C_1$-$C_{10})$-alkyl)-carbamoyl, N—$((C_6$-$C_{16})$-aryloxy-$(C_1$-$C_{10})$-alkyl)-carbamoyl, N—$((C_7$-$C_{16})$-aralkyloxy-$(C_1$-$C_{10})$-alkyl)-carbamoyl, N—$(C_1$-$C_{10})$alkyl-N—$((C_1$-$C_{10})$-alkoxy-$(C_1$-$C_{10})$-alkyl)-carbamoyl, N—$(C_1$-$C_{10})$-alkyl-N—$((C_6$-$C_{12})$-aryloxy-$(C_1$-$C_{10})$-alkyl)-carbamoyl, N—$(C_1$-$C_{10})$-alkyl-N—$((C_7$-$C_{16})$-aralkyloxy-$(C_1$-$C_{10})$-alkyl)-carbamoyl; CON$(CH_2)_h$, in which a $CH_2$ group can be replaced by O, S, N—$(C_1$-$C_8)$-alkylimino, N—$(C_3$-$C_8)$-cycloalkylimino, N—$(C_3$-$C_8)$-cycloalkyl-$(C_1$-$C_4)$-alkylimino, N—$(C_6$-$C_{12})$-arylimino, N—$(C_7$-$C_{16})$-aralkylimino, N—$(C_1$-$C_4)$-alkoxy-$(C_1$-$C_6)$-alkylimino, and h is from 3 to 7; a carbamoyl radical of the formula R

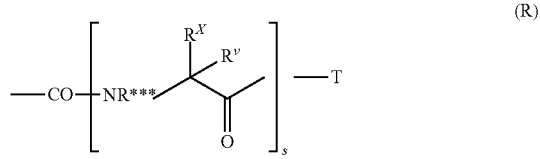

(R)

in which
$R^x$ and $R^v$ are each independently selected from hydrogen, $(C_1$-$C_6)$-alkyl, $(C_3$-$C_7)$-cycloalkyl, aryl, or the substituent of an α-carbon of an α-amino acid, to which the L- and D-amino acids belong,
s is 1-5,
T is OH, or NR*R**, and R*, R and R* are identical or different and are selected from hydrogen, $(C_6$-$C_{12})$-aryl, $(C_7$-$C_{11})$-aralkyl, $(C_1$-$C_8)$-alkyl, $(C_3$-$C_8)$-cycloalkyl, (+)-dehydroabietyl, $(C_1$-$C_8)$-alkoxy-$(C_1$-$C_8)$-alkyl, $(C_7$-$C_{12})$-aralkoxy-$(C_1$-$C_8)$-alkyl, $(C_6$-$C_{12})$-aryloxy-$(C_1$-$C_8)$-alkyl, $(C_1$-$C_{10})$-alkanoyl, optionally substituted $(C_7$-$C_{16})$-aralkanoyl, optionally substituted $(C_6$-$C_{12})$-aroyl; or R* and R** together are —$[CH_2]_h$, in which a $CH_2$ group can be replaced by O, S, SO, $SO_2$, N-acylamino, N—$(C_1$-$C_{10})$-alkoxycarbonylimino, N—$(C_1$-$C_8)$-alkylimino, N—$(C_3$-$C_8)$-cycloalkylimino, N—$(C_3$-$C_8)$-cycloalkyl-$(C_1$-$C_4)$-alkylimino, N—$(C_6$-$C_{12})$-arylimino, N—$(C_7$-$C_{16})$-aralkylimino, N—$(C_1$-$C_4)$-alkoxy-$(C_1$-$C_6)$-alkylimino, and h is from 3 to 7; carbamoyloxy, N—$(C_1$-$C_{12})$-alkylcarbamoyloxy, N,N-di-$(C_1$-$C_{12})$-alkylcarbamoyloxy, N—$(C_3$-$C_8)$-cycloalkylcarbamoyloxy, N—$(C_6$-$C_{12})$-arylcarbamoyloxy, N—$(C_7$-$c_{16})$-aralkylcarbamoyloxy, N—$(C_1$-$C_{10})$-alkyl-N—$(C_6$-$C_{12})$-arylcarbamoyloxy, N—$(C_1$-$C_{10})$-alkyl-N—$(C_7$-$C_{16})$-aralkylcarbamoyloxy, N—$((C_1$-$C_{10})$-alkyl)-carbamoyloxy, N—$((C_6$-$C_{12})$-aryloxy-$(C_1$-$C_{10})$-alkyl)carbamoyloxy, N—$((C_7$-$C_{16})$-aralkyloxy-$(C_1$-$C_{10})$-alkyl)-carbamoyloxy, N—$(C_1$-$C_{10})$-alkyl-N—$((C_1$-$C_{10})$-alkoxy-$(C_1$-$C_{10})$-alkyl)-carbamoyloxy, N—$(C_1$-$C_{10})$-alkyl-N—$((C_6$-$C_{12})$-aryloxy-$(C_1$-$C_{10})$-alkyl)-carbamoyloxy, N—$(C_1$-$C_{10})$-alkyl-N—$((C_7$-$C_{16})$-aralkyloxy-$(C_1$-$C_{10})$-alkyl)-carbamoyloxyamino, $(C_1$-$C_{12})$-alkylamino, di-$(C_1$-$C_{12})$-alkylamino, $(C_3$-$C_8)$-cycloalkylamino, $(C_3$-$C_{12})$-alkenylamino, $(C_3$-$C_{12})$-alkynylamino, N—$(C_6$-$C_{12})$-arylamino, N—$(C_7$-$C_{11})$-aralkylamino, N-alkyl-aralkylamino, N-alkyl-arylamino, $(C_1$-$C_{12})$-alkoxyamino, $(C_1$-$C_{12})$-alkoxy-N—$(C_1$-$C_{10})$-alkylamino, $(C_1$-$C_{12})$-alkanoylamino, $(C_3$-$C_8)$-cycloalkanoylamino, $(C_6$-$C_{12})$-aroylamino, $(C_7$-$C_{16})$-aralkanoylamino, $(C_1$-$C_{12})$-alkanoyl-N—$(C_1$-$C_{10})$-alkylamino, $(C_3$-$C_8)$-cycloalkanoyl-N—$(C_1$-$C_{10})$-alkylamino, $(C_6$-$C_{12})$-aroyl-N—$(C_1$-$C_{10})$-alkylamino, $(C_7$-$C_{11})$-aralkanoyl-N—$(C_1$-$C_{10})$-alkylamino, $(C_1$-$C_{12})$-alkanoylamino-$(C_1$-$C_8)$-alkyl, $(C_3$-$C_8)$-cycloalkanoylamino-$(C_1$-$C_8)$-alkyl, $(C_6$-$C_{12})$-aroylamino-$(C_1$-$C_8)$-alkyl, $(C_7$-$C_{16})$-aralkanoylamino-$(C_1$-$C_8)$-alkyl, amino-$(C_1$-$C_{10})$-alkyl, N—$(C_1$-$C_{10})$-alkylamino-$(C_1$-$C_{10})$-alkyl, N,N-di$(C_1$-$C_{10})$-alkylamino-$(C_1$-$C_{10})$-alkyl, $(C_3$-$C_8)$-cycloalkylamino$(C_1$-$C_{10})$-alkyl, $(C_1$-$C_{20})$-alkylmercapto, $(C_1$-$C_{20})$-alkylsulfinyl, $(C_1$-$C_{20})$-alkylsulfonyl, $(C_6$-$C_{12})$-arylmercapto, $(C_6$-$C_{12})$-arylsulfinyl, $(C_6$-$C_{12})$-arylsulfonyl, $(C_7$-$C_{16})$-aralkylmercapto, $(C_7$-$C_{16})$-aralkylsulfinyl, $(C_7$-$C_{16})$-aralkylsulfonyl, $(C_1$-$C_{12})$-alkylmercapto-$(C_1$-$C_6)$-alkyl, $(C_1$-$C_{12})$-alkylsulfinyl-$(C_1$-$C_6)$-alkyl, $(C_1$-$C_{12})$-alkylsulfonyl-$(C_1$-$C_6)$-alkyl, $(C_6$-$C_{12})$-arylmercapto-$(C_1$-$C_6)$-alkyl, $(C_6$-$C_{12})$-arylsulfinyl-$(C_1$-$C_6)$-alkyl, $(C_6$-$C_{12})$-arylsulfonyl-$(C_1$-$C_6)$-alkyl, $(C_7$-$C_{16})$-aralkyl mercapto-$(C_1$-$C_6)$-alkyl, $(C_7$-$C_{16})$-aralkylsulfinyl-$(C_1$-$C_6)$-alkyl, $(C_7$-$C_{16})$-aralkylsulfonyl-$(C_1$-$C_6)$-alkyl, sulfamoyl, N—$(C_1$-$C_{10})$-alkylsulfamoyl, N,N-di-$(C_1$-$C_{10})$-alkylsulfamoyl, $(C_3$-$C_8)$-cycloalkylsulfamoyl, N—$(C_6$-$C_{12})$-arylsulfamoyl, N—$(C_7$-$C_{16})$-aralkylsulfamoyl, N—$(C_1$-$C_{10})$-alkyl-N—$(C_6$-$C_{12})$-arylsulfamoyl, N—$(C_1$-$C_{10})$-alkyl-N—$(C_7$-$C_{16})$-aralkylsulfamoyl, $(C_1$-$C_{10})$-alkylsulfonamido, N—$((C_1$-$C_{10})$-alkyl)-$(C_1$-$C_{10})$-alkylsulfonamido, $(C_7$-$C_{16})$-aralkylsulfonamido, and N—$((C_1$-$C_{10})$-alkyl-$(C_7$-$C_{16})$-aralkylsulfonamido; where an aryl radical may be substituted by 1 to 5 substituents selected from hydroxyl, halogen, cyano, trifluoromethyl, nitro, carboxyl, $(C_2$-$C_{16})$-alkyl, $(C_3$-$C_8)$-cycloalkyl, $(C_3$-$C_8)$-cycloalkyl-$(C_1$-$C_{12})$-alkyl, $(C_3$-$C_8)$-cycloalkoxy, $(C_3$-$C_8)$-cycloalkyl-$(C_1$-$C_{12})$-alkoxy, $(C_3$-$C_8)$-cycloalkyloxy-$(C_1$-$C_{12})$-alkyl, $(C_3$-$C_8)$-cycloalkyloxy-$(C_1$-$C_{12})$-alkoxy, $(C_3$-$C_8)$-cycloalkyl-$(C_1$-$C_8)$-alkyl-$(C_1$-$C_6)$-alkoxy, $(C_3$-$C_8)$-cycloalkyl$(C_1$-$C_8)$-alkoxy-$(C_1$-$C_6)$-alkyl, $(C_3$-$C_8)$-cycloalkyloxy-$(C_1$-$C_8)$-alkoxy-$(C_1$-$C_6)$-alkyl, $(C_3$-$C_8)$-cycloalkoxy-$(C_1$-$C_8)$-alkoxy-$(C_1$-$C_8)$-alkoxy, $(C_6$-$C_{12})$-aryl, $(C_7$-$C_{16})$-aralkyl, $(C_2$-$C_{16})$-alkenyl, $(C_2$-$C_{12})$-alkynyl, $(C_1$-$C_{16})$-alkoxy, $(C_1$-$C_{16})$-alkenyloxy, $(C_1$-$C_{12})$-alkoxy-$(C_1$-$C_{12})$-alkyl, $(C_1$-$C_{12})$-alkoxy-$(C_1$-$C_{12})$-alkoxy, $(C_1$-$C_{12})$-alkoxy$(C_1$-$C_8)$-alkoxy-$(C_1$-$C_8)$-alkyl, $(C_6$-$C_{12})$-aryloxy, $(C_7$-$C_{16})$-aralkyloxy, $(C_6$-$C_{12})$-aryloxy-$(C_1$-$C_6)$-alkoxy, $(C_7$-$C_{16})$-aralkoxy-$(C_1$-$C_6)$-alkoxy, $(C_1$-$C_8)$-hydroxyalkyl, $(C_6$-$C_{16})$-aryloxy-$(C_1$-$C_8)$-alkyl, $(C_7$-$C_{16})$-aralkoxy-$(C_1$-$C_8)$-alkyl, $(C_6$-$C_{12})$-aryloxy-$(C_1$-$C_8)$-alkoxy-$(C_1$-$C_6)$-alkyl, $(C_7$-$C_{12})$-aralkyloxy-$(C_1$-$C_8)$-alkoxy-$(C_1$-$C_6)$-alkyl, —O—$[CH_2]_x C_f H_{(2f+1-g)} F_g$, —$OCF_2Cl$, —$OCF_2$—$CHFCl$, $(C_1$-$C_{12})$-alkylcarbonyl, $(C_3$-$C_8)$-cycloalkylcarbonyl, $(C_6$-$C_{12})$-arylcarbonyl, $(C_7$-$C_{16})$-aralkylcarbonyl, $(C_1$-$C_{12})$-alkoxycarbonyl, $(C_1$-$C_{12})$-alkoxy-$(C_1$-$C_{12})$-alkoxycarbonyl, $(C_6$-$C_{12})$-aryloxycarbonyl, $(C_7$-$C_{16})$-aralkoxycarbonyl, $(C_3$-$C_8)$-cycloalkoxycarbonyl, $(C_2$-$C_{12})$-alkenyloxycarbonyl, $(C_2$-$C_{12})$-alkynyloxycarbonyl, $(C_6$-$C_{12})$-aryloxy-$(C_1$-$C_6)$-alkoxycarbonyl, $(C_7$-$C_{16})$-aralkoxy-$(C_1$-$C_6)$-alkoxycarbonyl, $(C_3$-$C_8)$-cycloalkyl-$(C_1$-$C_6)$-alkoxycarbonyl, $(C_3$-$C_8)$-cycloalkoxy-$(C_1$-$C_6)$-alkoxycarbonyl, $(C_1$-$C_{12})$-alkylcarbonyloxy, $(C_3$-$C_8)$-cycloalkylcarbonyloxy, $(C_6$-$C_{12})$-arylcarbonyloxy, $(C_7$-$C_{16})$-aralkylcarbonyloxy, cinnamoyloxy, $(C_2$-$C_{12})$-alkenylcarbonyloxy, $(C_2$-$C_{12})$-alkynylcarbonyloxy, $(C_1$-$C_{12})$-alkoxycarbonyloxy, $(C_1$-$C_{12})$- alkoxy-($C_1$-$C_{12}$)-alkoxycarbonyloxy, ($C_6$-$C_{12}$)-aryloxycarbonyloxy, ($C_7$-$C_{16}$)-aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxycarbonyloxy, carbamoyl, N—($C_1$-$C_{12}$)-alkylcarbamoyl, N,N-di($C_1$-$C_{12}$)-alkylcarbamoyl, N—($C_3$-$C_8$)-cycloalkylcarbamoyl, N,N-dicyclo-($C_3$-$C_8$)-alkylcarbamoyl, N—($C_1$-$C_{10}$)-alkyl-N—($C_3$-$C_8$)-cycloalkylcarbamoyl, N—(($C_3$-$C_8$)-cycloalkyl-($C_1$-$C_6$)-alkyl)carbamoyl, N—($C_1$-$C_6$)-alkyl-N—(($C_3$-$C_8$)-cycloalkyl-($C_1$-$C_6$)-alkyl)carbamoyl, N-(+)-dehydroabietylcarbamoyl, N—($C_1$-$C_6$)-alkyl-N-(+)-dehydroabietylcarbamoyl, N—($C_6$-$C_{12}$)-arylcarbamoyl, N—($C_7$-$C_{16}$)-aralkylcarbamoyl, N—($C_1$-$C_{10}$)-alkyl-N—($C_6$-$C_{12}$)-arylcarbamoyl, N—($C_1$-$C_{10}$)-alkyl-N—($C_7$-$C_{16}$)-aralkylcarbamoyl, N—(($C_1$-$C_{16}$)-alkoxy-($C_1$-$C_{10}$)-alkyl)carbamoyl, N—(($C_6$-$C_{16}$)-aryloxy-($C_1$-$C_{10}$)-alkyl)carbamoyl, N—(($C_7$-$C_{16}$)-aralkyloxy-($C_1$-$C_{10}$)-alkyl)carbamoyl, N—($C_1$-$C_{10}$)-alkyl-N—(($C_1$-$C_{10}$)-alkoxy-($C_1$-$C_{10}$)-alkyl)carbamoyl, N—($C_1$-$C_{10}$)-alkyl-N—(($C_6$-$C_{12}$)-aryloxy-($C_1$-$C_{10}$)-alkyl)carbamoyl, N—($C_1$-$C_{10}$)-alkyl-N—(($C_7$-$C_{16}$)-aralkyloxy-($C_1$-$C_{10}$)-alkyl)-carbamoyl, CON($CH_2$)$_h$, in which a $CH_2$ group can be replaced by, O, S, N—($C_1$-$C_8$)-alkylimino, N—($C_3$-$C_8$)-cycloalkylimino, N—($C_3$-$C_8$)-cycloalkyl-($C_1$-$C_4$)-alkylimino, N—($C_6$-$C_{12}$)-arylimino, N—($C_7$-$C_{16}$)-aralkylimino, N—($C_1$-$C_4$)-alkoxy-($C_1$-$C_6$)-alkylimino, and h is from 3 to 7; carbamoyloxy, N—($C_1$-$C_{12}$)-alkylcarbamoyloxy, N,N-di-($C_1$-$C_{12}$)-alkylcarbamoyloxy, N—($C_3$-$C_8$)-cycloalkylcarbamoyloxy, N—($C_6$-$C_{16}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N—($C_1$-$C_{10}$)-alkyl-N—($C_7$-$C_{16}$)-aralkylcarbamoyloxy, N—(($C_1$-$C_{10}$)-alkyl)carbamoyloxy, N—(($C_6$-$C_{12}$)-aryloxy-($C_1$-$C_{10}$)-alkyl)carbamoyloxy, N—(($C_7$-$C_{16}$)-aralkyloxy-($C_1$-$C_{10}$)-alkyl)carbamoyloxy, N—($C_1$-$C_{10}$)-alkyl-N—(($C_1$-$C_{10}$)-alkoxy-($C_1$-$C_{10}$)-allyl)carbamoyloxy, N—($C_1$-$C_{10}$)-alkyl-N—(($C_6$-$C_{12}$)-aryloxy-($C_1$-$C_{10}$)-alkyl)carbamoyloxy, N—($C_1$-$C_{10}$)-alkyl-N—(($C_7$-$C_{16}$)-aralkyloxy-($C_1$-$C_{10}$)-alkyl) carbamoyloxy, amino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_{12}$)-alkynylamino, N—($C_6$-$C_{12}$)-arylamino, N—($C_7$-$C_{11}$)-aralkylamino, N-alkyl-aralkylamino, N-alkyl-arylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkanoylamino, ($C_3$-$C_8$)-cycloalkanoylamino, ($C_6$-$C_{12}$)-aroylamino, ($C_7$-$C_{16}$)-aralkanoylamino, ($C_1$-$C_{12}$)-alkanoyl-N—($C_1$-$C_{10}$)-alkylamino, ($C_3$-$C_8$)-cycloalkanoyl-N—($C_1$-$C_{10}$)-alkylamino, ($C_6$-$C_{12}$)-aroyl-N—($C_1$-$C_{10}$)-alkylamino, ($C_7$-$C_{11}$)-aralkanoyl-N—($C_1$-$C_{10}$)-alkylamino, ($C_1$-$C_{12}$)-alkanoylamino-($C_1$-$C_8$)-alkyl, ($C_3$-$C_8$)-cycloalkanoylamino-($C_1$-$C_8$)-alkyl, ($C_6$-$C_{12}$)-aroylamino-($C_1$-$C_8$)-alkyl, ($C_7$-$C_{16}$)-aralkanoylamino-($C_1$-$C_8$)-alkyl, amino-($C_1$-$C_{10}$)-alkyl, N—($C_1$-$C_{10}$)-alkylamino-($C_1$-$C_{10}$)-alkyl, N,N-di-($C_1$-$C_{10}$)-alkylamino-($C_1$-$C_{10}$)-alkyl, ($C_3$-$C_8$)-cycloalkylamino-($C_1$-$C_{10}$)-alkyl, ($C_1$-$C_{12}$)-alkylmercapto, ($C_1$-$C_{12}$)-alkylsulfinyl, ($C_1$-$C_{12}$)-alkylsulfonyl, ($C_6$-$C_{16}$)-arylmercapto, ($C_6$-$C_{16}$)-arylsulfinyl, ($C_6$-$C_{16}$)-arylsulfonyl, ($C_7$-$C_{16}$)-aralkylmercapto, ($C_7$-$C_{16}$)-aralkylsulfinyl, or ($C_7$-$C_{16}$)-aralkylsulfonyl;

or wherein $R^1$ and $R^2$, or $R^2$ and $R^3$ form a chain [$CH_2$]$_o$, which is saturated or unsaturated by a C=C double bond, in which 1 or 2 $CH_2$ groups are optionally replaced by O, S, SO, $SO_2$, or NR', and R' is hydrogen, ($C_6$-$C_{12}$)-aryl, ($C_1$-$C_8$)-alkyl, ($C_1$-$C_8$)-alkoxy-($C_1$-$C_8$)-alkyl, ($C_7$-$C_{12}$)-aralkoxy-($C_1$-$C_8$)-alkyl, ($C_6$-$C_{12}$)-aryloxy-($C_1$-$C_8$)-alkyl, ($C_1$-$C_{10}$)-alkanoyl, optionally substituted ($C_7$-$C_{16}$)-aralkanoyl, or optionally substituted (C6-C12)-aroyl; and o is 3, 4 or 5;

or wherein the radicals $R^1$ and $R^2$, or $R^2$ and $R^3$, together with the pyridine or pyridazine carrying them, form a 5,6,7,8-tetrahydroisoquinoline ring, a 5,6,7,8-tetrahydroquinoline ring, or a 5,6,7,8-tetrahydrocinnoline ring;

or wherein $R^1$ and $R^2$, or $R^2$ and $R^3$ form a carbocyclic or heterocyclic 5- or 6-membered aromatic ring;

or where $R^1$ and $R^2$, or $R^2$ and $R^3$, together with the pyridine or pyridazine carrying them, form an optionally substituted heterocyclic ring systems selected from thienopyridines, furanopyridines, pyridopyridines, pyrimidinopyridines, imidazopyridines, thiazolopyridines, oxazolopyridines, quinoline, isoquinoline, and cinnoline; where quinoline, isoquinoline or cinnoline preferably satisfy the formulae Ia, Ib and Ic:

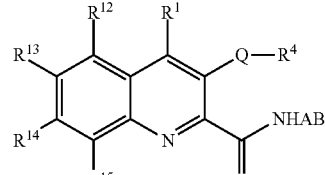

(Ia)

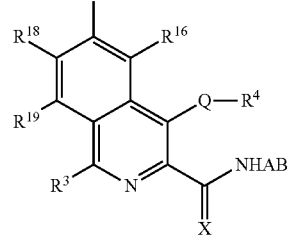

(Ib)

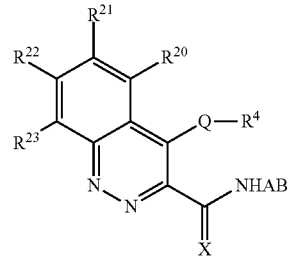

(Ic)

and the substituents $R^{12}$ to $R^{23}$ in each case independently of each other have the meaning of $R^1$, $R^2$ and $R^3$;

or wherein the radicals $R^1$ and $R^2$, together with the pyridine carrying them, form a compound of Formula Id:

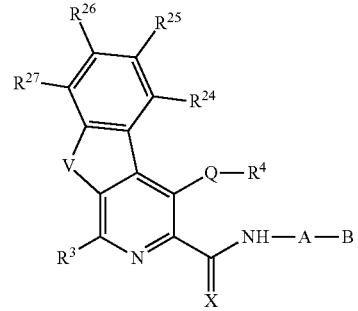

(Id)

where V is S, O, or NR$^k$, and R$^k$ is selected from hydrogen, ($C_1$-$C_6$)-alkyl, aryl, or benzyl; where an aryl radical may be optionally substituted by 1 to 5 substituents as defined above; and $R^{24}$, $R^{25}$, $R^{26}$, and $R^{27}$ in each case independently of each other have the meaning of $R^1$, $R^2$ and $R^3$;

f is 1 to 8;
g is 0 or 1 to (2f+1);
x is 0 to 3; and
h is 3 to 7;
including the physiologically active salts and prodrugs derived therefrom.

Exemplary compounds according to Formula (I) are described in European Patent Nos. EP0650960 and EP0650961. All compounds listed in EP0650960 and EP0650961, in particular, those listed in the compound claims and the final products of the working examples, are hereby incorporated into the present application by reference herein. Exemplary compounds of Formula (I) include, but are not limited to, [(3-Hydroxy-pyridine-2-carbonyl)-amino]-acetic acid (Compound G) and [(3-methoxy-pyridine-2-carbonyl)-amino]-acetic acid (Compound P).

Additionally, exemplary compounds according to Formula (I) are described in U.S. Pat. No. 5,658,933. All compounds listed in U.S. Pat. No. 5,658,933, in particular, those listed in the compound claims and the final products of the working examples, are hereby incorporated into the present application by reference herein. Exemplary compounds of Formula (I) include, but are not limited to, 3-methoxypyridine-2-carboxylic acid N-(((hexadecyloxy)-carbonyl)-methyl)-amide hydrochloride, 3-methoxypyridine-2-carboxylic acid N-(((1-octyloxy)-carbonyl)-methyl)-amide, 3-methoxypyridine-2-carboxylic acid N-(((hexyloxy)-carbonyl)-methyl)-amide, 3-methoxypyridine-2-carboxylic acid N-(((butyloxy)-carbonyl)-methyl)-amide, 3-methoxypyridine-2-carboxylic acid N-(((2-nonyloxy)-carbonyl)-methyl)-amide racemate, 3-methoxypyridine-2-carboxylic acid N-(((heptyloxy)-carbonyl)-methyl)-amide, 3-benzyloxypyridine-2-carboxylic acid N-(((octyloxy)-carbonyl)-methyl)-amide, 3-benzyloxypyridine-2-carboxylic acid N-(((butyloxy)-carbonyl)-methyl)-amide, 5-(((3-(1-butyloxy)-propyl)-amino)-carbonyl)-3-methoxypyridine-2-carboxylic acid N-((benzyloxycarbonyl)-methyl)-amide, 5-(((3-(1-butyloxy)-propyl)-amino)-carbonyl)-3-methoxypyridine-2-carboxylic acid N-(((1-butyloxy)-carbonyl)-methyl)-amide, and 5-(((3-lauryloxy)-propyl)amino)-carbonyl)-3-methoxypyridine-2-carboxylic acid N-(((benzyloxy)-carbonyl)-methyl)-amide.

Additional compounds according to Formula (I) are substituted heterocyclic carboxyamides described in U.S. Pat. No. 5,620,995; 3-hydroxypyridine-2-carboxamidoesters described in U.S. Pat. No. 6,020,350; sulfonamidocarbonylpyridine-2-carboxamides described in U.S. Pat. No. 5,607,954; and sulfonamidocarbonyl-pyridine-2-carboxamides and sulfonamidocarbonyl-pyridine-2-carboxamide esters described in U.S. Pat. Nos. 5,610,172 and 5,620,996. All compounds listed in these patents, in particular, those compounds listed in the compound claims and the final products of the working examples, are hereby incorporated into the present application by reference herein.

Exemplary compounds according to Formula (Ia) are described in U.S. Pat. Nos. 5,719,164 and 5,726,305. All compounds listed in the foregoing patents, in particular, those listed in the compound claims and the final products of the working examples, are hereby incorporated into the present application by reference herein. Exemplary compounds of Formula (1a) include, but are not limited to, N-((3-hydroxy-6-isopropoxy-quinoline-2-carbonyl)-amino)-acetic acid (Compound H), N-((6-(1-butyloxy)-3-hydroxyquinolin-2-yl)-carbonyl)-glycine, [(3-hydroxy-6-trifluoromethoxy-quinoline-2-carbonyl)-amino]-acetic acid (Compound I), N-((6-chloro-3-hydroxyquinolin-2-yl)-carbonyl)-glycine, N-((7-chloro-3-hydroxyquinolin-2-yl)-carbonyl)-glycine, and [(6-chloro-3-hydroxy-quinoline-2-carbonyl)-amino]-acetic acid (Compound O).

Exemplary compounds according to Formula (Ib) are described in U.S. Pat. No. 6,093,730. All compounds listed in U.S. Pat. No. 6,093,730, in particular, those listed in the compound claims and the final products of the working examples, are hereby incorporated into the present application by reference herein. Exemplary compounds of Formula (1b) include, but are not limited to, N-((1-chloro-4-hydroxy-7-(2-propyloxy) isoquinolin-3-yl)-carbonyl)-glycine, N-((1-chloro-4-hydroxy-6-(2-propyloxy) isoquinolin-3-yl)-carbonyl)-glycine, N-((1-chloro-4-hydroxy-isoquinoline-3-carbonyl)-amino)-acetic acid (Compound B), N-((1-chloro-4-hydroxy-7-methoxyisoquinolin-3-yl)-carbonyl)-glycine, N-((1-chloro-4-hydroxy-6-methoxyisoquinolin-3-yl)-carbonyl)-glycine, N-((7-butyloxy)-1-chloro-4-hydroxyisoquinolin-3-yl)-carbonyl)-glycine, N-((6-benzyloxy-1-chloro-4-hydroxy-isoquinoline-3-carbonyl)-amino)-acetic acid (Compound J), ((7-benzyloxy-1-chloro-4-hydroxy-isoquinoline-3-carbonyl)-amino)-acetic acid methyl ester (Compound K), N-((7-benzyloxy-1-chloro-4-hydroxy-isoquinoline-3-carbonyl)-amino)-acetic acid (Compound L), N-((8-chloro-4-hydroxyisoquinolin-3-yl)-carbonyl)-glycine, N-((7-butoxy-4-hydroxy-isoquinoline-3-carbonyl)-amino)-acetic acid (Compound M).

Additionally, compounds related to Formula (I) that can also be used in the methods of the invention include, but are not limited to, 6-cyclohexyl-1-hydroxy-4-methyl-1H-pyridin-2-one (Compound N), 7-(4-methyl-piperazin-1-ylmethyl)-5-phenylsulfanylmethyl-quinolin-8-ol (Compound D), 4-nitro-quinolin-8-ol (Compound E), and 5-butoxymethyl-quinolin-8-ol (Compound F). Further, the invention provides additional exemplary compounds wherein, e.g., position A and B together may be, e.g., hexanoic acid, cyanomethyl, 2-aminoethyl, benzoic acid, 1H-benzoimidazol-2-ylmethyl, etc.

In other embodiments, compounds used in the methods of the invention are selected from a compound of the formula (II)

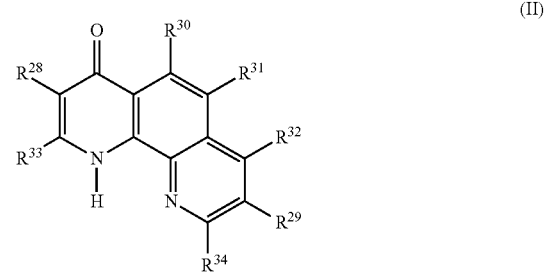

where
$R^{28}$ is hydrogen, nitro, amino, cyano, halogen, $(C_1-C_4)$-alkyl, carboxy or a metabolically labile ester derivative thereof; $(C_1-C_4)$-alkylamino, di-$(C_1-C_4)$-alkylamino, $(C_1-C_6)$-alkoxycarbonyl, $(C_2-C_4)$-alkanoyl, hydroxy-$(C_1-C_4)$-alkyl, carbamoyl, N—$(C_1-C_4)$-alkylcarbamoyl, $(C_1-C_4)$-alkylthio, $(C_1-C_4)$-alkylsulfinyl, alkylsulfonyl, phenylthio, phenylsulfinyl, phenylsulfonyl, said phenyl or phenyl groups being optionally substituted with 1 to 4 identical or different halogen, $(C_1-C_4)$-alkyoxy, $(C_1-C_4)$-alkyl, cyano, hydroxy, trifluoromethyl, fluoro-$(C_1-C_4)$-allylthio, fluoro-$(C_1-C_4)$-alkylsulfinyl, fluoro-$(C_1-C_4)$-alkylsulfonyl, $(C_1-C_4)$-alkoxy-$(C_2-C_4)$-alkoxycarbonyl, N,N-di-[$(C_1-C_4)$-alkyl]carbamoyl-$(C_1-C_4)$-alkoxycarbonyl, $(C_1-C_4)$-alkylamino-$(C_2-C_4)$-alkoxycarbonyl, di-$(C_1-C_4)$-alkylamino-$(C_2-C_4)$-alkoxycarbonyl, $(C_1-C_4)$-alkoxy-$(C_2-C_4)$-alkoxy-$(C_2-C_4)$-alkoxycarbonyl, $(C_2-C_4)$-alkanoyloxy-$C_1-C_4$)-alkyl, or N-[amino-$(C_2-C_8)$-alkyl]-carbamoyl;
$R^{29}$ is hydrogen, hydroxy, amino, cyano, halogen, $(C_1-C_4)$-alkyl, carboxy or metabolically labile ester derivative thereof, $(C_1-C_4)$-alkylamino, di-$(C_1-C_4)$-alkylamino, $(C_1-C_6)$- alkoxycarbonyl, $(C_2-C_4)$-alkanoyl, $(C_1-C_4)$-alkoxy, carboxy-$(C_1-C_4)$-alkoxy, $(C_1-C_4)$-alkoxycarbonyl-$(C_1-C_4)$-alkoxy, carbamoyl, N—$(C_1-C_8)$-alkylcarbamoyl, N,N-di-$(C_1-C_8)$-alkylcarbamoyl, N-[amino-$(C_2-C_8)$-alkyl]-carbamoyl, N—$(C_1-C_4)$-alkylamino-$(C_1-C_8)$-alkyl]-carbamoyl, N-[di-$(C_1-C_4)$-alkylamino-$(C_1-C_8)$-alkyl)]-carbamoyl, N-cyclohexylcarbamoyl, N-[cyclopentyl]-carbamoyl, N—$(C_1-C_4)$-alkylcyclohexylcarbamoyl, N—$(C_1-C_4)$-alkylcyclopentylcarbamoyl, N-phenylcarbamoyl, N—$(C_1-C_4)$-alkyl-N-phenylcarbamoyl, N,N-diphenylcarbamoyl, N-[phenyl-$(C_1-C_4)$-alkyl]-carbamoyl, N—$(C_1-C_4)$-alkyl-N-[phenyl-$(C_1-C_4)$-alkyl]-carbamoyl, or N,N-di-[phenyl-$(C_1-C_4)$-alkyl]-carbamoyl, said phenyl or phenyl groups being optionally substituted with 1 to 4 identical or different halogen, $(C_1-C_4)$-alkyloxy, $(C_1-C_4)$-alkyl, cyano, hydroxy, trifluoromethyl, N—[$(C_2-C_4)$-alkanoyl]-carbamoyl, N—[$(C_1-C_4)$-alkoxycarbonyl]-carbamoyl, N-[fluoro-$(C_2-C_6)$-alkyl]-carbamoyl, N,N-[fluoro-$(C_2-C_6)$-alkyl]-N—$(C_1-C_4)$-allylcarbamoyl, N,N-[di-fluoro-$(C_2-C_6)$-alkyl]carbamoyl, pyrrolidin-1-ylcarbonyl, piperidinocarbonyl, piperazin-1-ylcarbonyl, morpholinocarbonyl, wherein the heterocyclic group, is optionally substituted with 1 to 4, $(C_1-C_4)$-alkyl, benzyl, 1,2,3,4-tetrahydro-isoquinolin-2-ylcarbonyl, N,N-[di-$(C_1-C_4)$-alkyl]-thiocarbamoyl, N—$(C_2-C_4)$-alkanoylamino, or N-[$(C_1-C_4)$-alkoxycarbonyl]-amino;

$R^{30}$ is hydrogen, $(C_1-C_4)$-alkyl, $(C_2-C_4)$-alkoxy, halo, nitro, hydroxy, fluoro-(1-4C)alkyl, or pyridinyl;

$R^{31}$ is hydrogen, $(C_1-C_4)$-alkyl, $(C_2-C_4)$-alkoxy, halo, nitro, hydroxy, fluoro-$(C_1-C_4)$-alkyl, pyridinyl, or methoxy;

$R^{32}$ is hydrogen, hydroxy, amino, $(C_1-C_4)$-alkylamino, di-$(C_1-C_4)$-alkylamino, halo, $(C_1-C_4)$-alkoxy-$(C_2-C_4)$-alkoxy, fluoro-$(C_1-C_6)$-alkoxy, pyrrolidin-1-yl, piperidino, piperazin-1-yl, or morpholino, wherein the heterocyclic group is optionally substituted with 1 to 4 identical or different $(C_1-C_4)$-alkyl or benzyl; and $R^{33}$ and $R^{34}$ are individually selected from hydrogen, $(C_1-C_4)$-alkyl, and $(C_1-C_4)$-alkoxy;

including pharmaceutically-acceptable salts and pro-drugs derived therefrom.

Exemplary compounds of Formula (II) are described in U.S. Pat. Nos. 5,916,898 and 6,200,974, and International Publication No. WO 99/21860. All compounds listed in the foregoing patents and publication, in particular, those listed in the compound claims and the final products of the working examples, are hereby incorporated into the present application by reference herein. Exemplary compounds of Formula (II) include 4-oxo-1,4-dihydro-[1,10]phenanthroline-3-carboxylic acid (Compound A) (see, e.g., Seki et al. (1974) Chem Abstracts 81:424, No. 21), 3-carboxy-5-hydroxy-4-oxo-3,4-dihydro-1,10-phenanthroline, 3-carboxy-5-methoxy-4-oxo-3,4-dihydro-1,10-phenanthroline, 5-methoxy-4-oxo-1,4-dihydro-[1,10]phenanthroline-3-carboxylic acid ethyl ester, 5-methoxy-4-oxo-1,4-dihydro-[1,10]phenanthroline-3-carboxylic acid (Compound Q), and 3-carboxy-8-hydroxy-4-oxo-3,4-dihydro-1,10-phenanthroline.

In other embodiments, compounds used in the methods of the invention are selected from a compound of the formula (III)

(III)

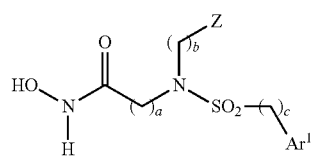

or pharmaceutically acceptable salts thereof, wherein:
a is an integer from 1 to 4;
b is an integer from 0 to 4;
c is an integer from 0 to 4;

Z is selected from the group consisting of $(C_3-C_{10})$ cycloalkyl, $(C_3-C_{10})$ cycloalkyl independently substituted with one or more $Y^1$, 3-10 membered heterocycloalkyl and 3-10 membered heterocycloalkyl independently substituted with one or more $Y^1$; $(C_5-C_{20})$ aryl, $(C_5-C_{20})$ aryl independently substituted with one or more $Y^1$, 5-20 membered heteroaryl and 5-20 membered heteroaryl independently substituted with one or more $Y^1$;

$Ar^1$ is selected from the group consisting of $(C_5-C_{20})$ aryl, $(C_5-C_{20})$ aryl independently substituted with one or more $Y^2$, 5-20 membered heteroaryl and 5-20 membered heteroaryl independently substituted with one or more $Y^2$;

each $Y^1$ is independently selected from the group consisting of a lipophilic functional group, $(C_5-C_{20})$ aryl, $(C_6-C_{26})$ alkaryl, 5-20 membered heteroaryl and 6-26 membered alkheteroaryl;

each $Y^2$ is independently selected from the group consisting of —R', —OR', —OR", —SR', —SR", —NR'R', —NO$_2$, —CN, -halogen, -trihalomethyl, trihalomethoxy, —C(O)R', —C(O)OR', —C(O)NR'R', —C(O)NR'OR', —C(NR'R')=NOR', —NR'—C(O)R', —SO$_2$R', —SO$_2$R", —NR'—SO$_2$—R', —NR'—C(O)—NR'R', tetrazol-5-yl, —NR'—C(O)—OR', —C(NR'R')=NR', —S(O)—R', —S(O)—R", and —NR'—C(S)—NR'R'; and each R' is independently selected from the group consisting of —H, $(C_1-C_8)$ alkyl, $(C_2-C_8)$ alkenyl, and $(C_2-C_8)$ alkynyl; and each R" is independently selected from the group consisting of $(C_5-C_{20})$ aryl and $(C_5-C_{20})$ aryl independently substituted with one or more —OR', —SR', —NR'R', —NO$_2$, —CN, halogen or trihalomethyl groups, or wherein c is 0 and $Ar^1$ is an N' substituted urea-aryl, the compound has the structural formula (IIIa):

(IIIa)

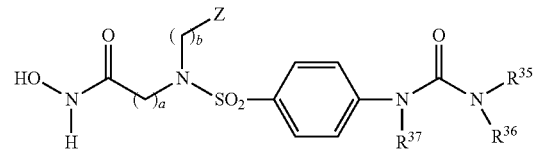

or pharmaceutically acceptable salts thereof, wherein:
a, b, and Z are as defined above; and
$R^{35}$ and $R^{36}$ are each independently selected from the group consisting of hydrogen, $(C_1-C_8)$ alkyl, $(C_2-C_8)$ alkenyl, $(C_2-C_8)$ alkynyl, $(C_3-C_{10})$ cycloalkyl, $(C_5-C_{20})$ aryl, $(C_5-C_{20})$ substituted aryl, $(C_6-C_{26})$ alkaryl, $(C_6-C_{26})$ substituted alkaryl, 5-20 membered heteroaryl, 5-20 membered substituted heteroaryl, 6-26 membered alk-heteroaryl, and 6-26 membered substituted alk-heteroaryl; and
$R^{37}$ is independently selected from the group consisting of hydrogen, $(C_1-C_8)$ alkyl, $(C_2-C_8)$ alkenyl, and $(C_2-C_8)$ alkynyl.

Exemplary compounds of Formula (III) are described in International Publication No. WO 00/50390. All compounds listed in WO 00/50390, in particular, those listed in the compound claims and the final products of the working examples, are hereby incorporated into the present application by reference herein. Exemplary compounds of Formula (III) include 3-{[4-(3,3-dibenzyl-ureido)-benzenesulfonyl]-[2-(4-methoxy-phenyl)-ethyl]-amino}-N-hydroxy-propionamide (Compound C), 3-{{4-[3-(4-chloro-phenyl)-ureido]-benzenesulfonyl}-[2-(4-methoxy-phenyl)-ethyl]-amino}-N-hydroxy-propionamide, and 3-{{4-[3-(1,2-diphenyl-ethyl)-ureido]-benzenesulfonyl}-[2-(4-methoxy-phenyl)-ethyl]-amino}-N-hydroxy-propionamide.

Based on the common mechanism of action of the 2-oxoglutarate dioxygenase family members, such as dependence on $Fe^{2+}$ and 2-oxoglutarate for activity, in certain aspects the invention is directed to use of compounds, including the compounds described herein, to inhibit HIFα hydroxylation and thus stabilize HIFα in an oxygen-independent manner. Further, the examples and figures of the present invention demonstrate that application of such compounds stabilize HIFα and subsequently induce HIF-regulated gene products in vitro and in vivo. In specific embodiments, these compounds are used to produce a specific benefit in the prevention and treatment of ischemic and hypoxic conditions.

The methods of the present invention stabilize HIFα in a dose-dependent manner in cells grown in a normoxic environment. Although different cell types show different levels of HIFα in the presence of a compound of the invention, all of the cell lines tested showed some level of HIFα stabilization. The level of HIFα in untreated cells is usually low to undetectable.

Stabilization of HIFα leads to HIF-dependent gene expression in vitro and in vivo, including genes encoding angiogenic factors such as VEGF, Flt-1, EG-VEGF, PAI-1, adrenomedullin, and Cyr61. Thus, the ability to stabilize HIFα has potential benefits in the induction of angiogenesis and prevention of tissue damage due to ischemia and hypoxia. For example, transgenic mice expressing constitutively active HIF-1α in the epidermis show enhanced expression of each VEGF isoform and a significant increase in dermal capillaries. Unlike overexpression of one VEGF isoform alone, the hypervascularity induced by HIFα shows no edema, inflammation, or vascular leakage. (See, Elson et al. (2001) Genes Dev 15:2520-2532; Detmar et al. (1998) J Invest Derm 111:1-6; Larcher et al. (1998) Oncogene 17:303-311; and Thurston et al. (1999) Science 286:2511-2514.) Therefore, in certain aspects, methods of the invention can be used to induce therapeutic angiogenesis, which involves the development of collateral blood vessels to revascularize ischemic tissues.

Additionally, the methods of the invention produce a dose-dependent decrease in oxygen consumption in cells without any affect on cell viability. Stable HIF complexes activate expression of proteins involved in glucose uptake and utilization, such as glucose transporter (GluT)-1 and GluT-3; aldolase-A, enolase-1, hexokinase-1 and -2, and phosphofructokinase-L and -C. The reduction in oxygen consumption associated with HIFα stabilization is potentially due to a shift in cellular metabolism from aerobic to anaerobic energy production. The present methods can thus be applied to generate energy under low oxygen conditions, beneficial in ischemic and hypoxic conditions such as, for example, peripheral arterial disease, DVT, angina pectoris, pulmonary embolism, stroke, and myocardial infarction. Methods of increasing glucose uptake and utilization by cells of the body, generally applicable to the treatment of other conditions, e.g., diabetes, are also provided.

The invention further provides methods for increasing oxygen-carrying capacity by inducing erythropoiesis, and facilitating iron transport and utilization. Specifically, methods of the invention increase expression of erythropoietin (EPO), a naturally occurring hormone that stimulates the production of red blood cells. (See, e.g., commonly owned, copending U.S. Patent Application Publication No. 2003/0153503, incorporated herein by reference in its entirety.) Methods for increasing expression of enzymes and proteins involved in iron uptake, transport, and processing are specifically contemplated. Such enzymes and proteins include, but are not limited to, transferrin and transferrin receptor, which together facilitate iron transport to and uptake by, e.g., erythroid tissue; and ceruloplasmin, a ferroxidase required to oxidize ferrous iron to ferric iron. As transferrin can only bind and transport ferric iron, ceruloplasmin is important for supply of iron to tissues. The ability of the methods of the invention to increase both endogenous erythropoietin and transport and utilization of iron provides specific advantage in oxygen delivery in both normoxic and hypoxic environments.

In one aspect, the invention includes methods that provide neuroprotective benefits, e.g., by stabilizing HIFα. For example, both VEGF and EPO have been shown to be neuroprotective. (See, e.g., Jin et al. (2000) Proc Natl Acad Sci USA. 97:10242-10247; Bocker-Meffert et al. (2002) Invest Ophthalmol V is Sci 43:2021-2026; Buemi et al. (2002) Clin Sci (Lond) 103:275-282; and Siren et al. (2001) Proc Natl Acad Sci USA 98:4044-4049.) EPO also facilitates recovery from spinal cord injuries and provides neuroprotective benefits when induced prior to an ischemic event. (See, e.g., Gorio et al. (2002) Proc Natl Acad Sci USA 99:9450-9455; and Dawson (2002) Lancet 359:96-97.) As the methods of the invention increase expression of neuroprotective factors such as VEGF and EPO, the methods provide neuroprotective benefit that can be applied to treatment, pretreatment, or prevention of conditions including, e.g., diabetic neuropathy, stroke, neurodegenerative disease, trauma, injury, e.g., concussions, spinal cord injuries, etc., or prior to surgical procedures, e.g., wherein cerebral ischemic reperfusion injury may result.

Hypoxic preconditioning has been shown to effectively protect against subsequent acute ischemic insult. As the primary effect of hypoxia is stabilization of HIFα and subsequent activation of HIF-regulated genes, the methods of the invention will mimic hypoxic preconditioning in a normoxic environment. For example, the methods may be used prior to surgery, wherein ischemic-reperfusion injury may be expected to produce deleterious results in the patient. Such preventive therapy, when applied prior to an ischemic event, can be provided at any time point prior to the event, in a single or repeated dose format.

The methods of the invention also coordinately upregulate genes involved in oxidative stress and vascular tone. Such genes include, e.g., inducible nitric oxide synthase (iNOS), and heme oxygenase 1. Production of iNOS has also been associated with the beneficial effects of hypoxic preconditioning in several animal models. (See, e.g., Serracino-Inglott et al. (2002) BMC Gastroenterol 2:22-27; Kuntscher et al. (2002) Br J Plast Surg 55:430-433.) Significantly, blocking iNOS activity attenuates but does not abrogate the beneficial effects of preconditioning, whereas nonspecifically blocking protein production completely abrogates the benefits of preconditioning. (Wang et al. (2002) Cardiovasc Res 56:33-42.) This suggests that iNOS is an important component of the physiological response to preconditioning, but is not the only factor. As the methods of the invention coordinately regulate various factors, including iNOS, involved in hypoxic response, the methods of the invention will more accurately replicate the beneficial effects of hypoxic preconditioning.

Methods of Using the Compounds of the Invention

The present invention provides methods of inhibiting HIFα hydroxylation, thereby stabilizing HIF and activating HIF-regulated gene expression. The methods can be applied to the prevention, pretreatment, or treatment of conditions associated with HIF including ischemic and hypoxic conditions. Such conditions include, for example, myocardial infarction, liver ischemia, renal ischemia, and stroke; peripheral vascular disorders, ulcers, burns, and chronic wounds; pulmonary embolism; and ischemic-reperfusion injury, including, for example, ischemic-reperfusion injury associated with surgery and organ transplantation. In one embodiment, the present invention provides methods of stabilizing HIFα before, during, or immediately after ischemia or hypoxia, particularly in association with myocardial infarction, stroke, or renal ischemic-reperfusion injury.

In one aspect, the invention provides methods for treating various ischemic and hypoxic conditions, in particular, using the compounds described herein. In one embodiment, the methods of the invention produce therapeutic benefit when administered following ischemia or hypoxia. For example, the methods of the invention produce a dramatic decrease in morbidity and mortality following myocardial infarction, and a significant improvement in heart architecture and performance. Further, the methods of the invention improve liver function when administered following hepatic toxic-ischemic injury. Hypoxia is a significant component of liver disease, especially in chronic liver disease associated with hepatotoxic compounds such as ethanol. Additionally, expression of genes known to be induced by HIFα, e.g., nitric oxide synthase and glucose transporter-1, is increased in alcoholic liver disease. (See, e.g., Areel et al. (1997) Hepatology 25:920-926; Strubelt (1984) Fundam Appl Toxicol 4:144-151; Sato (1983) Pharmacol Biochem Behav 18 (Suppl 1):443-447; Nanji et al. (1995) Am J Pathol 146:329-334; and Morio et al. (2001) Toxicol Appl Pharmacol 172:44-51.)

Therefore, the present invention provides methods of treating conditions associated with ischemia or hypoxia, the method comprising administering a therapeutically effective amount of a compound or a pharmaceutically acceptable salt thereof, alone or in combination with a pharmaceutically acceptable excipient, to a subject. In one embodiment, the compound is administered immediately following a condition producing acute ischemia, e.g., myocardial infarction, pulmonary embolism, intestinal infarction, ischemic stroke, and renal ischemic-reperfusion injury. In another embodiment, the compound is administered to a patient diagnosed with a condition associated with the development of chronic ischemia, e.g., cardiac cirrhosis, macular degeneration, pulmonary embolism, acute respiratory failure, neonatal respiratory distress syndrome, and congestive heart failure. In yet another embodiment, the compound is administered immediately after a trauma or injury.

In another aspect, the invention provides methods for treating a patient at risk of developing an ischemic or hypoxic condition, e.g., individuals at high risk for atherosclerosis, etc., using the compounds described herein. Risk factors for atherosclerosis include, e.g., hyperlipidemia, cigarette smoking, hypertension, diabetes mellitus, hyperinsulinemia, and abdominal obesity. Therefore, the present invention provides methods of preventing ischemic tissue injury, the method comprising administering a therapeutically effective amount of a compound or a pharmaceutically acceptable salt thereof, alone or in combination with a pharmaceutically acceptable excipient, to a patient in need. In one embodiment, the compound can be administered based on predisposing conditions, e.g., hypertension, diabetes, occlusive arterial disease, chronic venous insufficiency, Raynaud's disease, chronic skin ulcers, cirrhosis, congestive heart failure, and systemic sclerosis.

In one specific embodiment, the methods are used to increase vascularization and/or granulation tissue formation in damaged tissue, wounds, and ulcers. For example, compounds of the invention have been shown to be effective in stimulating granulation tissue formation in wound healing. Granulation tissue contains newly formed, leaky blood vessels and a provisional stroma of plasma proteins, such as fibrinogen and plasma fibronectin. Release of growth factors from inflammatory cells, platelets, and activated endothelium, stimulates fibroblast and endothelial cell migration and proliferation within the granulation tissue. Ulceration can occur if vascularization or neuronal stimulation is impaired. The methods of the invention are effective at promoting granulation tissue formation. Thus, the invention provides methods for treating a patient having tissue damage due to, e.g., an infarct, having wounds induced by, e.g., trauma or injury, or having chronic wounds or ulcers produced as a consequence of a disorder, e.g., diabetes. The method comprises administering a therapeutically effective amount of a compound or a pharmaceutically acceptable salt thereof, alone or in combination with a pharmaceutically acceptable excipient, to a patient in need.

In another aspect, the invention provides methods of using the compounds to pretreat a subject to decrease or prevent the development of tissue damage associated with ischemia or hypoxia. The methods of the invention produce therapeutic benefit when administered immediately before a condition involving ischemia or hypoxia. For example, application of the methods of the invention prior to induction of myocardial infarction shows statistically significant improvement in heart architecture and performance. Further, the methods of the invention produce therapeutic benefit when administered immediately before and during ischemic-reperfusion injury, significantly reducing diagnostic parameters associated with renal failure.

Therefore, the invention provides methods of pretreating a subject to decrease or prevent the tissue damage associated with ischemia or hypoxia, the method comprising administering a therapeutically effective amount of a compound or a pharmaceutically acceptable salt thereof, alone or in combination with a pharmaceutically acceptable excipient, to a patient with a history of ischemic disorders, e.g., myocardial infarctions, or having symptoms of impending ischemia, e.g., angina pectoris. In another embodiment, the compound can be administered based on physical parameters implicating possible ischemia, e.g., individuals placed under general anesthesia or temporarily working at high altitudes. In yet another embodiment, the compounds may be used in organ transplants to pretreat organ donors and to maintain organs removed from the body prior to implantation in the recipient.

Previous studies have shown that certain compounds used in the methods of the present invention are effective inhibitors of procollagen prolyl 4-hydroxylase. While it is recognized that recovery from an initial infarct or wound requires connective tissue deposition within the necrotic region, the present invention demonstrates no adverse affects of treatment with respect to scar formation. Thus, based on the benefits provided by certain compounds of the invention on treatment and prevention of hypoxic tissue damage and fibrosis, the present invention contemplates a "dual-therapy" approach to treatment or prevention of conditions involving ischemia or hypoxia, including ischemia or hypoxia associated with subsequent reactive fibrosis, e.g., myocardial infarction and resultant congestive heart failure. The method may use one compound that inhibits more than one 2-oxoglutarate dioxygenase enzyme, e.g., HIF prolyl hydroxylase and procollagen prolyl 4-hydroxylase, with either the same specificity or with different specificities. Alternatively, the method may use a combination of compounds wherein each compound specifically inhibits only one 2-oxoglutarate dioxygenase enzyme, e.g., one compound specifically inhibits HIF prolyl hydroxylase and a second compound specifically inhibits procollagen prolyl 4-hydroxylase.

In one aspect, a compound of the invention inhibits one or more 2-oxoglutarate dioxygenase enzymes. In one embodiment, the compound inhibits at least two 2-oxoglutarate dioxygenase family members, e.g., HIF prolyl hydroxylase and HIF asparagine-hydroxylase (FIH-1), with either the same specificity or with differential specificity. In another embodiment, the compound is specific for one 2-oxoglutarate dioxygenase, e.g., HIF prolyl hydroxylase, and shows little to no specificity for other family members.

The compounds can be administered in combination with various other therapeutic approaches. In one embodiment, the compound is administered with another 2-oxoglutarate dioxygenase inhibitor, wherein the two compounds have differential specificity for individual 2-oxoglutarate dioxygenase family members. The two compounds may be administered at the same time as a ratio of one relative to the other. Determination of a ratio appropriate to a given course of treatment or a particular subject is within the level of skill in the art. Alternatively, the two compounds may be administered consecutively during a treatment time course, e.g., following myocardial infarction. In a particular embodiment, one compound specifically inhibits HIF prolyl hydroxylase enzyme activity, and a second compound specifically inhibits procollagen prolyl 4-hydroxylase enzyme activity. In another specific embodiment, one compound specifically inhibits HIF prolyl hydroxylase enzyme activity, and a second compound specifically inhibits HIF asparaginyl-hydroxylase enzyme activity. In another embodiment, the compound is administered with another therapeutic agent having a different mode of action, e.g., an ACE inhibitor (ACEI), angiotensin-II receptor blocker (ARB), statin, diuretic, digoxin, carnitine, etc.

Pharmaceutical Formulations and Routes of Administration

The compositions of the present invention can be delivered directly or in pharmaceutical compositions along with suitable carriers or excipients, as is well known in the art. Present methods of treatment can comprise administration of an effective amount of a compound of the invention to a subject having or at risk for an ischemic condition, e.g., congestive heart failure, atherosclerosis, etc. In a preferred embodiment, the subject is a mammalian subject, and in a most preferred embodiment, the subject is a human subject. Preferred routes of administration include oral and transdermal delivery mechanisms.

An effective amount of such agents can readily be determined by routine experimentation, as can the most effective and convenient route of administration and the most appropriate formulation. Various formulations and drug delivery systems are available and selection of an appropriate formulation is within the level of skill in the art. (See, e.g., Gennaro, ed. (1995) *Remington's Pharmaceutical Sciences*, supra; and Hardman, Limbird, and Gilman, eds. (2001) *The Pharmacological Basis of Therapeutics*, supra.)

Suitable routes of administration may, for example, include oral, rectal, transmucosal, nasal, or intestinal administration and parenteral delivery, including intramuscular, subcutaneous, intramedullary injections, as well as intrathecal, direct intraventricular, intravenous, intraperitoneal, intranasal, or intraocular injections. The agent or composition thereof may be administered in a local rather than a systemic manner. For example, a suitable agent can be delivered via injection or in a targeted drug delivery system, such as a depot or sustained release formulation.

The pharmaceutical compositions of the present invention may be manufactured by any of the methods well-known in the art, such as by conventional mixing, dissolving, granulating, dragee-making, levigating, emulsifying, encapsulating, entrapping, or lyophilizing processes. As noted above, the compositions of the present invention can include one or more physiologically acceptable carriers such as excipients and auxiliaries that facilitate processing of active molecules into preparations for pharmaceutical use.

Proper formulation is dependent upon the route of administration chosen. For injection, for example, the composition may be formulated in aqueous solutions, preferably in physiologically compatible buffers such as Hanks's solution, Ringer's solution, or physiological saline buffer. For transmucosal or nasal administration, penetrants appropriate to the barrier to be permeated are used in the formulation. Such penetrants are generally known in the art. For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject. The compounds may also be formulated in rectal compositions such as suppositories or retention enemas, e.g., containing conventional suppository bases such as cocoa butter or other glycerides.

Pharmaceutical preparations for oral use can be obtained as solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

In one embodiment, the compounds of the present invention can be administered transdermally, such as through a skin patch, or topically. In one aspect, the transdermal or topical formulations of the present invention can additionally comprise one or multiple penetration enhancers or other effectors, including agents that enhance migration of the delivered compound. Transdermal or topical administration could be preferred, for example, in situations in which location specific delivery is desired.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide, or any other suitable gas. In the case of a pressurized aerosol, the appropriate dosage unit may be determined by providing a valve to deliver a metered amount. Capsules and cartridges of, for example, gelatin, for use in an inhaler or insufflator may be formulated. These typically contain a powder mix of the compound and a suitable powder base such as lactose or starch.

Compositions formulated for parenteral administration by injection, e.g., by bolus injection or continuous infusion, can be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Formulations for parenteral administration include aqueous solutions or other compositions in water-soluble form.

Suspensions of the active compounds may also be prepared as appropriate oily injection suspensions. Suitable lipophilic solvents or vehicles include fatty oils such as sesame oil and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Alternatively, the active ingredient may be in powder form for constitution with a suitable vehicle, e.g., sterile pyrogen-free water, before use.

As mentioned above, the compositions of the present invention may also be formulated as a depot preparation. Such long acting formulations may be administered by implantation (for example, subcutaneously or intramuscular) or by intramuscular injection. Thus, for example, the present compounds may be formulated with suitable polymeric or hydrophobic materials (for example as an emulsion in an acceptable oil) or ion exchange resins, or as sparingly soluble derivatives, for example, as a sparingly soluble salt.

Suitable carriers for the hydrophobic molecules of the invention are well-known in the art and include co-solvent systems comprising, for example, benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system is effective in dissolving hydrophobic compounds and produces low toxicity upon systemic administration. Naturally, the proportions of a co-solvent system may be varied considerably without destroying its solubility and toxicity characteristics. Furthermore, the identity of the co-solvent components may be varied. For example, other low-toxicity nonpolar surfactants may be used instead of polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic molecules may be employed. Liposomes and emulsions are well known examples of delivery vehicles or carriers for hydrophobic drugs. Liposomal delivery systems are discussed above in the context of gene-delivery systems. Certain organic solvents such as dimethylsulfoxide also may be employed, although usually at the cost of greater toxicity. Additionally, the compounds may be delivered using sustained-release systems, such as semi-permeable matrices of solid hydrophobic polymers containing the effective amount of the composition to be administered. Various sustained-release materials are established and available to those of skill in the art. Sustained-release capsules may, depending on their chemical nature, release the compounds for a few weeks up to over 100 days. Depending on the chemical nature and the biological stability of the therapeutic reagent, additional strategies for protein stabilization may be employed.

For any composition used in the present methods of treatment, a therapeutically effective dose can be estimated initially using a variety of techniques well known in the art. For example, based on information obtained from a cell culture assay, a dose can be formulated in animal models to achieve a circulating concentration range that includes the $IC_{50}$. Similarly, dosage ranges appropriate for human subjects can be determined, for example, using data obtained from cell culture assays and other animal studies.

A therapeutically effective dose of an agent refers to that amount of the agent that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}, ED_{50}$. Agents that exhibit high therapeutic indices are preferred.

Dosages preferably fall within a range of circulating concentrations that includes the $ED_{50}$ with little or no toxicity. Dosages may vary within this range depending upon the dosage form employed and the route of administration utilized. The exact formulation, route of administration, and dosage should be chosen, according to methods known in the art, in view of the specifics of a subject's condition.

Dosage amount and interval may be adjusted individually to provide plasma levels of the active moiety that are sufficient to modulate HIFα stabilization and HIF-regulated gene induction, as desired, i.e., minimal effective concentration (MEC). The MEC will vary for each compound but can be estimated from, for example, in vitro data. Dosages necessary to achieve the MEC will depend on individual characteristics of the compound and the route of administration. Agents or compositions thereof should be administered using a regimen which maintains plasma levels above the MEC for about 10-90% of the duration of treatment, preferably about 30-90% of the duration of treatment, and most preferably between 50-90%. In cases of local administration or selective uptake, the effective local concentration of the drug may not be related to plasma concentration.

The amount of agent or composition administered will, of course, be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition. Suitable conditions indicated on the label may include treatment of disorders or diseases in which ischemia or hypoxia is a major indication.

Compound Screening and Identification

The present invention further provides methods of screening for and identifying additional compounds that inhibit HIFα hydroxylation, or that stabilize HIFα, etc.

Various assays and screening techniques, including those described below, can be used to identify small molecules that modulate (e.g., increase or decrease) the level or activity of HIFα. Assays will typically provide for detectable signals associated with the consumption of a reaction substrate or production of a reaction product. Detection can involve, for example, fluorophores, radioactive isotopes, enzyme conjugates, and other detectable labels well known in the art. The results may be qualitative or quantitative. Isolation of the reaction product may be facilitated by a label, such as biotin or a histidine tag that allows purification from other reaction components via precipitation or affinity chromatography.

Assays for HIFα hydroxylation may involve measuring hydroxylated proline or lysine residues in HIFα or a fragment thereof (see, e.g., Palmerini et al. (1985) J Chromatogr 339: 285-292), or measuring formation of succinate from 2-oxoglutarate in the presence of enzyme and HIFα or a fragment thereof (see, e.g., Cunliffe et al. (1986) Biochem J 240:617-619). Exemplary procedures that measure HIFα hydroxylation are described in Ivan et al. (supra) and Example 10. An exemplary procedure that measures production of succinate from 2-oxoglutarate is described by Kaule and Gunzler. (1990; Anal Biochem 184:291-297.) Substrate molecules may include HIFα or a fragment thereof, e.g., HIF(556-575); for example, an exemplary substrate for use in the assay described in Example 10 is [methoxycoumarin]-DLDLEAL-APYIPADDDFQL-amide (SEQ ID NO:5). Enzyme may include, e.g., HIFα prolyl hydroxylase (see, e.g., GenBank Accession No. AAG33965, etc.), obtained from any source. Enzyme may also be present in a crude cell lysate or in a partially purified form. Compounds that stabilize HIFα or that inhibit hydroxylation of HIFα may be identified by measuring and comparing enzyme activity in the absence and presence of the compound.

Additionally and in combination with the above methods, compounds can be identified by any of a variety of screening techniques known in the art. Such screening methods may allow for target polypeptides or the compounds to be free in solution, affixed to a solid support, borne on a cell surface, or located within a cell. For example, test compounds may be arrayed on a surface and analyzed for activity in a manner analogous to array methods currently available in the art. (See, e.g., Shalon et al. (1995) International Publication No. WO 95/35505; Baldeschweiler et al. (1995) International Publication No. WO 95/251116; Brennan et al. (1995) U.S. Pat. No. 5,474,796; and Heller et al. (1997) U.S. Pat. No. 5,605,662.)

These and other embodiments of the present invention will readily occur to those of ordinary skill in the art in view of the disclosure herein, and are specifically contemplated.

EXAMPLES

The invention is understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Example 1

HIFα Stabilization in Cells In Vitro

Human cells derived from adenovirus-transformed fetal kidney epithelium (293A), cervical epithelial adenocarcinoma (HeLa), hepatocellular carcinoma (Hep3B), foreskin fibroblast (HFF), mammary gland epithelial adenocarcinoma (MCF7), umbilical vein endothelium (HUVEC), microvascular endothelium (HMEC-1), squamous carcinoma (SSC-25), lung fibroblast (HLF), and venous endothelium (AG10774B) tissues (see, e.g., American Type Culture Collection, Manassas Va.; and Qbiogene, Carlsbad Calif.) were separately seeded into 35 mm culture dishes and grown at 37° C., 20% $O_2$, 5% $CO_2$ in media as follows: HeLa cells in Dulbecco's Modification of Eagle's Medium (DMEM), 2% fetal bovine serum (FBS); HFF and HLF cells in DMEM, 10% FBS; 293A cells in DMEM, 5% FBS; HUVEC and AG10774B cells in Endothelial Growth Media (EGM-2; BioWhittaker, Inc., Walkersville Md.); and HMEC-1 in RPMI 1640, 10% FBS; and Hep3B cells in Minimal Essential Medium (MEM), Earle's BSS (Mediatech Inc., Herndon Va.), 2 mM L-glutamine, 0.1 mM non-essential amino acids, 1 mM sodium pyruvate, 10% FBS. When cell layers reached confluence, the media was replaced with OPTI-MEM media (Invitrogen Life Technologies, Carlsbad Calif.) and cell layers were incubated for approximately 24 hours in 20% $O_2$, 5% $CO_2$ at 37° C. Compound of the invention (one of compounds A to O) or DMSO (0.5 to 1%) was then added to existing medium, and incubation was continued overnight.

Following incubation, the media was removed, centrifuged, and stored for analysis (see below). The cells were washed two times in cold phosphate buffered saline (PBS) and then lysed in 1 ml of 10 mM Tris (pH 7.4), 1 mM EDTA, 150 mM NaCl, 0.5% IGEPAL (Sigma-Aldrich, St. Louis Mo.), and a protease inhibitor mix (Roche Molecular Biochemicals) for 15 minutes on ice. Cell lysates were centrifuged at 3,000×g for 5 minutes at 4° C., and the cytosolic fractions (supernatant) were collected. The nuclei (pellet) were resuspended and lysed in 100 µl of 20 mM HEPES (pH 7.2), 400 mM NaCl, 1 mM EDTA, 1 mM dithiothreitol, and a protease mix (Roche Molecular Biochemicals), centrifuged at 13,000×g for 5 minutes at 4° C., and the nuclear protein fractions (supernatant) were collected.

Nuclear fractions were normalized based on protein concentration and loaded onto a 4-12% TG gel and fractionated under reducing conditions. Proteins were transferred to a PVDF membrane (Invitrogen Corp., Carlsbad Calif.) at 500 mA for 1.5 hours. The membrane was blocked in T-TBS, 2% milk for 1 hour at room temperature and incubated overnight with mouse anti-human HIF-1α antibody (BD Biosciences, Bedford Mass.), diluted 1:250 in T-TBS, 2% milk. The blot was developed using SUPERSIGNAL WEST chemiluminescent substrate (Pierce, Rockford Ill.). As can be seen in FIG. 1A, various compounds of the invention (Compounds A to F) stabilized HIFα in a normoxic environment in a dose-dependent manner, allowing HIFα to accumulate within the cell. As seen in FIG. 1B, various cell types, including fibroblasts, epithelial cells, endothelial cells, and hepatocytes from various sources, showed dose-dependent stabilization of HIFα when treated with a compound of the invention in a normoxic environment.

Figure 2:
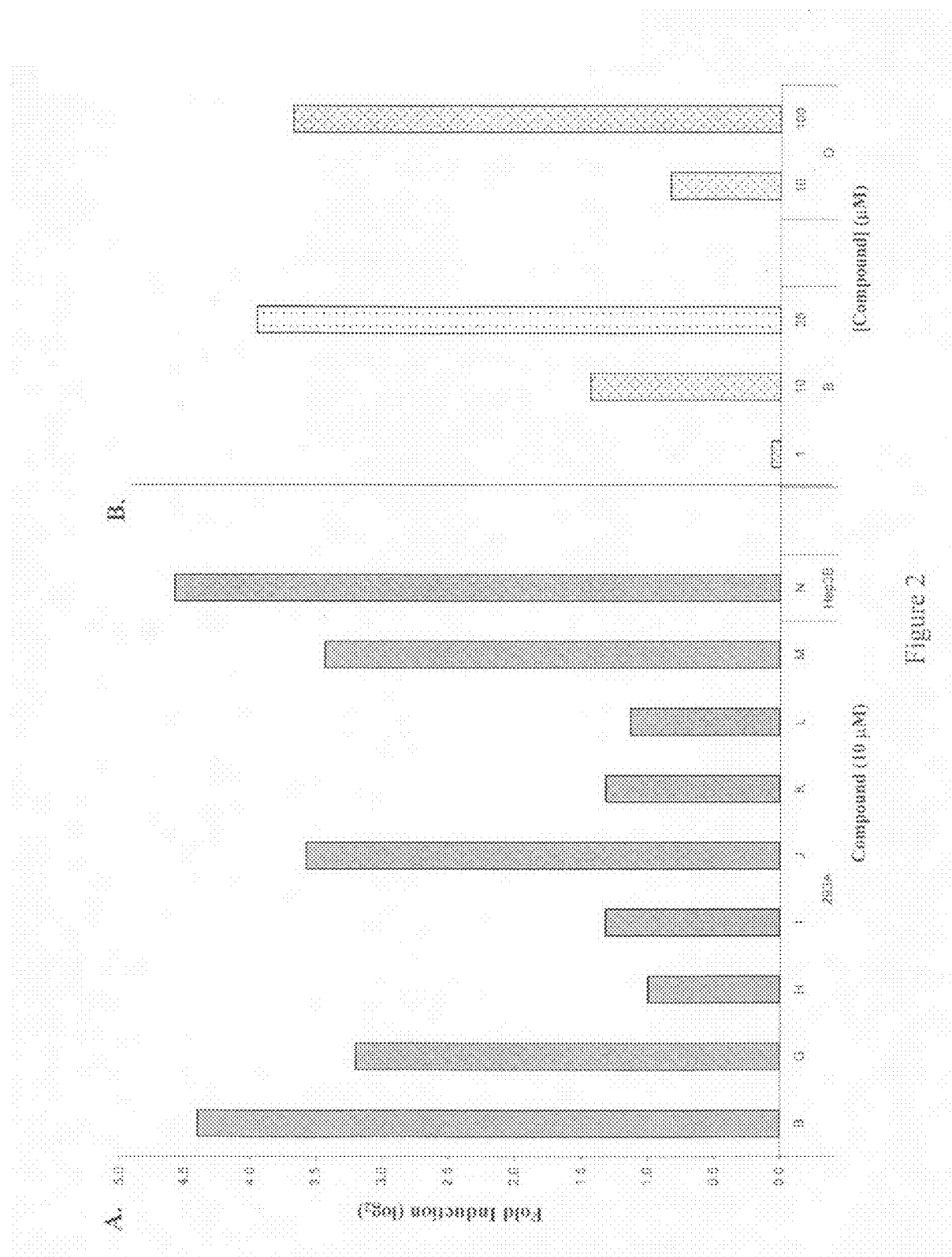
FIGS. 2A and 2B show HIF-1α stabilization and accumulation in human cells treated with compounds of the invention.

Alternatively, nuclear and cytosolic fractions as prepared above were analyzed for HIF-1α using a QUANTIKINE immunoassay (R&D Systems, Inc., Minneapolis Minn.) according to the manufacturer's instructions. As shown in FIG. 2A, epithelial cells (293A) and hepatocytes (Hep3B) treated with various compounds of the invention (Compounds B and G to O) showed stabilization and accumulation of HIFα as compared to vehicle-treated control cells. As shown in FIG. 2B, cells treated with compounds of the invention showed dose-dependent stabilization of HIFα.

Example 2

Effect on Oxygen Consumption

Oxygen Sensor cell culture plates (BD Biosciences, Bedford Mass.) contain a ruthenium complex which is more fluorescent in the absence of oxygen. Therefore, the fluorescent read-out is increased by the presence of oxygen-consuming cells in the plate, which change the equilibrium to lower oxygen saturation and higher fluorescence. A compound that stabilizes HIF by inhibiting hydroxylation is expected to decrease oxygen consumption by decreasing oxygen consumed by the hydroxylation event itself and/or by shifting cellular metabolism from aerobic to anaerobic energy production.

Human cells derived from adenovirus-transformed fetal kidney epithelium (293A) or cervical epithelial adenocarcinoma (HeLa) (American Type Culture Collection) were grown to confluence in media (high glucose DMEM (Mediatech, Inc., Herndon Va.), 1% penicillin/streptomycin mixture (Mediatech), 1% fetal bovine serum) at 37° C., 10% $CO_2$. Cells were collected and resuspended in media at a density of 500,000 cells/ml. The cell suspension was distributed at 0.2 ml/well into each well of an Oxygen Biosensor 96-well cell culture plate (BD Biosciences). The following treatments were added in 10 µl volumes to triplicate sets of wells: (1) 0.5% DMSO; (2) 200 µM sodium dodecyl sulfate; or (3) 1, 10, or 50 µM compound (one of compounds B, G, or a prodrug of compound V [pV]).

Cultures were incubated at 37° C., 10% $CO_2$ for 72 hours and plates were then read in an FL600 flourimeter (Biotek Instruments, Inc., Winooski Vt.) at an excitation wavelength of 485 nm and emission wavelength of 590 nm. Data was plotted as a function of fold change relative to DMSO control ($O_2$ consumption) or absorbance at a wavelength of 450 nm (WST-1) and descriptive statistical analysis was performed using EXCEL software (Microsoft Corporation, Bellevue Wash.).

Figure 3:
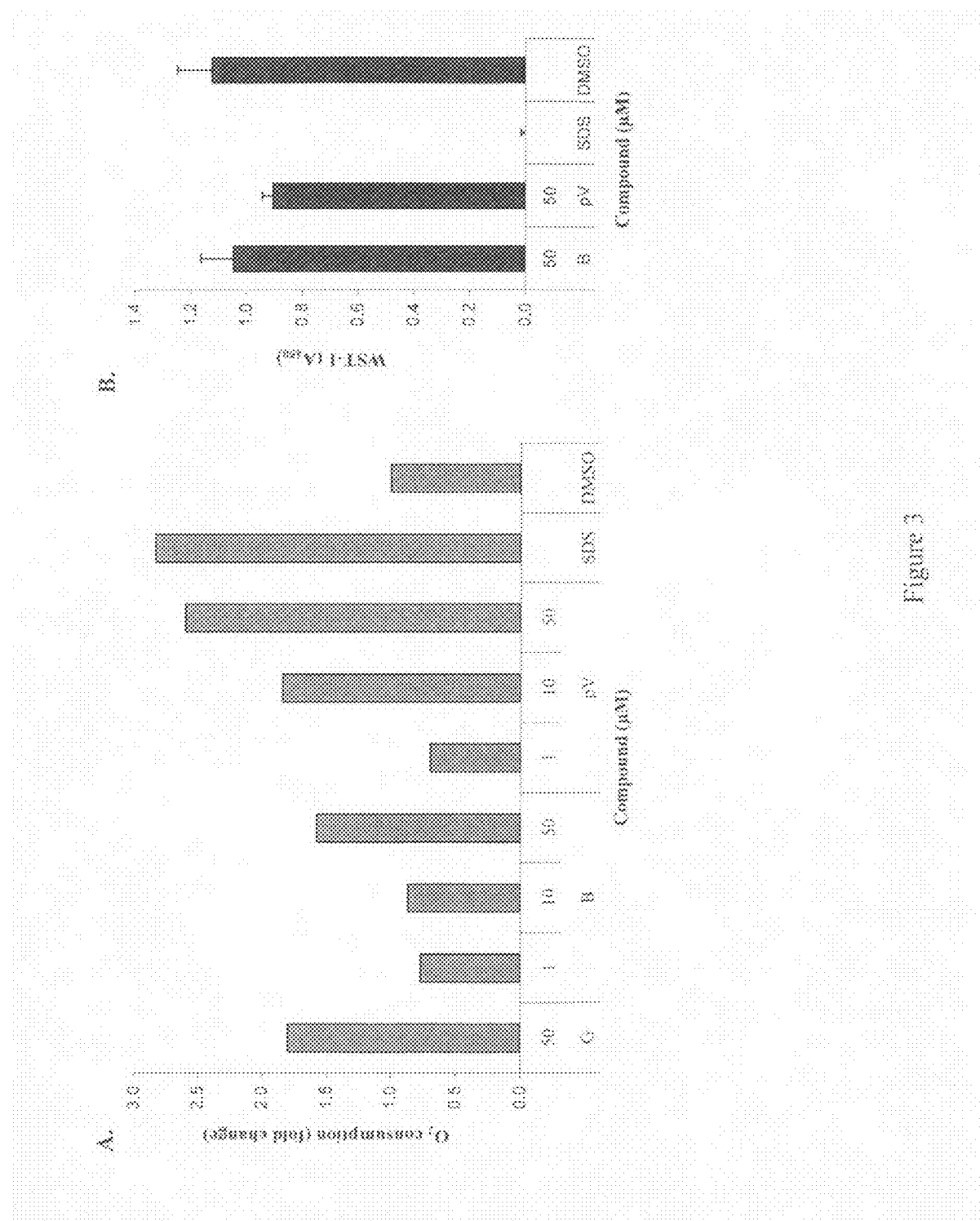
FIGS. 3A and 3B show oxygen consumption and cell viability in human cells treated with compounds of the invention.

FIG. 3A shows the fold change in oxygen consumption in cells treated with compound relative to control cells. As can be seen in the figure, all of the compounds produced a decrease in oxygen consumption to some degree. Further, the reduction in oxygen consumption was dose-dependent (FIG. 3A), and even at the highest doses little to no loss of cell viability was detected (FIG. 1B). Additional experiments (not shown) in various cell culture test systems, including incorporation of 3H-thymidine and total incorporation of amino acids, confirmed that the decrease in oxygen consumption was not associated with cytotoxicity.

Example 3

Expression of HIF-Regulated Genes In Vitro

Figure 4:
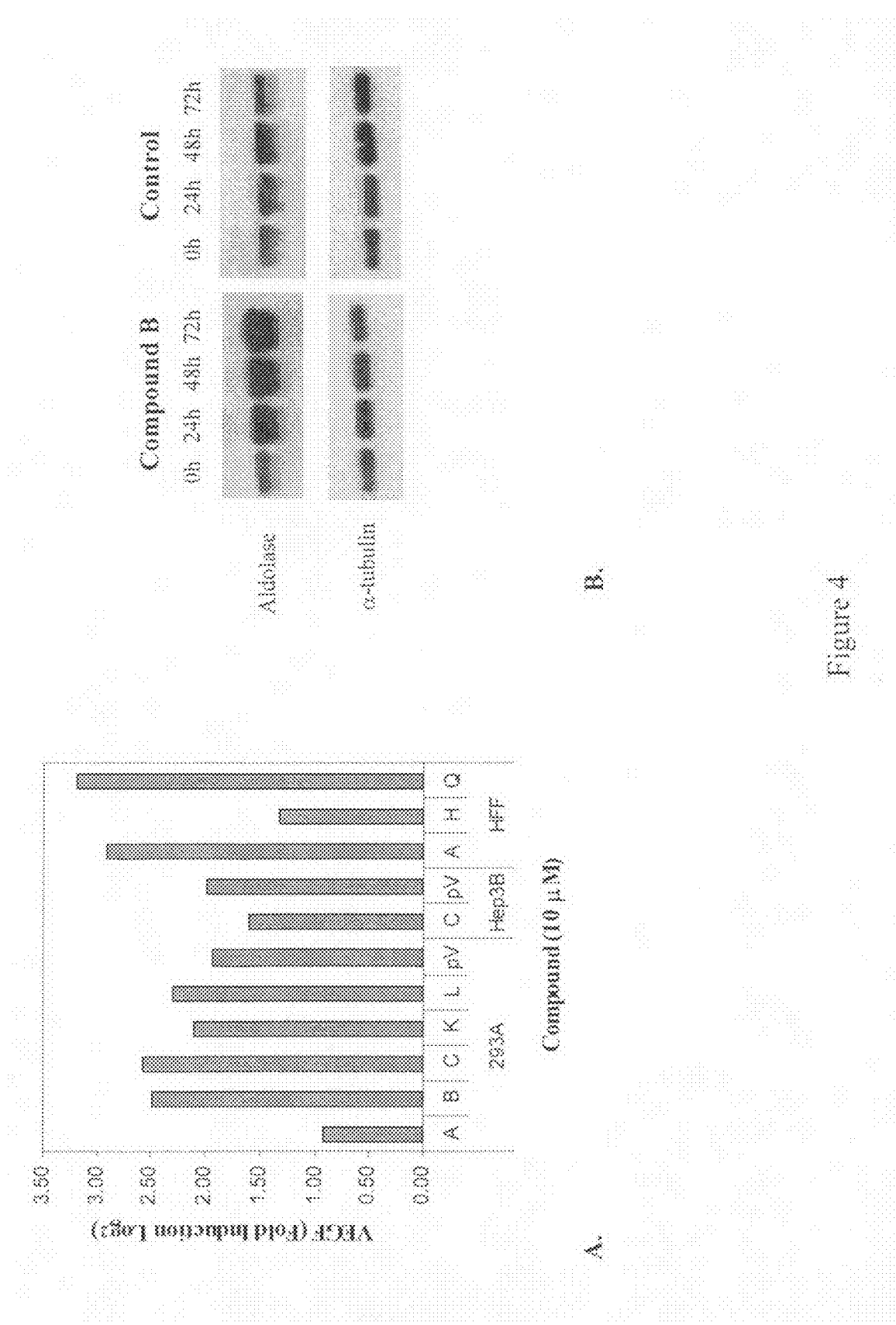
FIGS. 4A and 4B show increased expression of HIF-responsive genes in human cells treated with compounds of the invention.

Conditioned media collected from cell cultures grown as in Example 1 was analyzed for vascular endothelial growth factor (VEGF) expression using a QUANTIKINE immunoassay (R&D Systems) according to the manufacturer's instructions. As seen in FIG. 4A, fibroblasts (HFF), epithelial cells (293A), and hepatocytes (Hep3B) treated with various compounds of the invention (one of compounds A, B, C, H, K, L, Q, and a prodrug of compound V [pV]) showed an increase in VEGF expression (FIG. 4A). Values on the y-axis represent fold-induction relative to control and are reported on a $\log_2$ scale, such that a value of 1 represents 2-fold induction.

Alternatively, human cells derived from adenovirus-transformed fetal kidney epithelium (293A) were cultured in DMEM, 5% FBS, 1% Penicillin-Streptomycin at 37° C. and 10% $CO_2$. After 48 hours, the cells were harvested and were plated confluent in 35 mm culture dishes in regular culture media, and after 1 day the media was changed to Opti-Mem I. After 18 to 24 hours, compound B was added to the media and incubation was continued for an additional 18 hours. Culture supernatant was then removed, the plates were placed on ice, lysis buffer (LB)-1 was added and the cells were harvested by scraping. The scraped cells were collected and incubated for 15 minutes on ice followed by centrifugation at 3000 g for 5 minutes at 4° C. The supernatant, which represents the cytosolic fraction, was collected and cytosolic proteins were separated under denaturing and reducing conditions using SDS polyacrylamide gels that were loaded with equal amounts of protein per lane.

Gel electrophoresis was conducted at 150 V for 2 hours, and after SDS-PAGE the proteins were transferred to a PVDF membrane for 1.5 hours at 400 mA at 4° C. The membrane was then incubated in blocking buffer, washed once with T-TBS, and then anti-aldolase antibody diluted to working concentration in blocking buffer was added and the blots were incubated over night with gentle agitation at 4° C. The membrane was then washed 4 times with T-TBS, followed by incubation for one hour at room temperature with blocking buffer containing labeled secondary antibody. The membrane was then washed four times with T-TBS. The antigen specific for the primary antibody was visualized by exposing X-ray-film and developed using the ECL SUPERSIGNAL WEST FEMTO or PICO chemiluminescent substrate (Pierce, Rockford Ill.) according to the manufacturer's instructions.

FIG. 4B shows that the compound increased expression of aldolase, an enzyme involved in glycolysis, over time. Thus, stabilization of HIFα by compounds of the invention leads to subsequent increase in expression of HIF-regulated genes.

Example 4

HIFα Stabilization in Cells In Vivo

Swiss Webster male mice (30-32 g) are obtained, e.g., from Charles River Laboratories, Inc. (Wilmington Mass.), or Simonsen, Inc. (Gilroy, Calif.), and treated by oral gavage one or more times per day for at least one day with a 2 ml/kg volume of either 0.5% carboxymethyl cellulose (CMC; Sigma-Aldrich) (control) or 5.0% compound (0.5% CMC). At one or more time points after the final dose, e.g., two and five hours, animals are anesthetized with isoflurane and 0.1 ml blood is collected, e.g., from the orbital sinus into a heparinized tube. After all selected time points have been reached, animals are subjected to a sub-lethal dose of $CO_2$ and blood is collected from the abdominal vein into a heparinized tube. All blood samples are stored at −80° C.

Tissues isolated from animals treated with compounds of the invention as described above are analyzed for HIFα protein levels as follows. Tissues are homogenized in 3 ml of 10 mM Tris (pH 7.4), 1 mM EDTA, 150 mM NaCl, 0.5%

IGEPAL (Sigma-Aldrich), and a protease inhibitor mix (Roche Molecular Biochemicals) for 15 seconds using a POLYTRON PT-1200 homogenizer (Brinkmann Instruments, Inc., Westbury N.Y.). Cell lysates are centrifuged at 3,000×g for 5 minutes at 4° C., and the cytosolic fraction (supernatant) is collected. The nuclei (pellet) are resuspended and lysed in 100 µl of 20 mM HEPES (pH 7.2), 400 mM NaCl, 1 mM EDTA, 1 mM dithiothreitol, and a protease mix (Roche Molecular Biochemicals), centrifuged at 13,000×g for 5 minutes at 4° C., and the nuclear protein fraction (supernatant) is collected.

Nuclear fractions are normalized based on protein concentration and loaded onto a 4 to 12% TG gel and fractionated under reducing conditions. Proteins are transferred to a PVDF membrane (Invitrogen Life Technologies) at 500 mA for 1.5 hours. The membrane is blocked in T-TBS, 2% milk for 1 hour at room temperature and incubated overnight with anti-HIFα antibody diluted in T-TBS, 2% milk. The blot is developed using SUPERSIGNAL WEST PICO chemiluminescent substrate (Pierce, Rockford Ill.).

Alternatively, nuclear and cytosolic fractions as prepared above are analyzed for HIF-1α using a QUANTIKINE immunoassay (R&D Systems) according to the manufacturer's instructions.

Example 5

Expression of HIF-Regulated Genes In Vivo

Experiment I

Twenty four Swiss Webster male mice (30-32 g) were obtained from Simonsen, Inc., and treated by oral gavage with a 4 ml/kg volume of either 0.5% CMC (Sigma-Aldrich) (0 mg/kg/day) or 1.25% Compound A (25 mg/ml in 0.5% CMC) (100 mg/kg). At 4, 8, 16, 24, 48, or 72 hours after the final dose, animals were anesthetized with isoflurane and a blood sample was collected from the abdominal vein. The blood sample was collected into a MICROTAINER serum separator tube (Becton-Dickinson, Franklin Lakes N.J.), incubated at room temperature for 30 minutes, centrifuged at 8,000 rpm at 4° C. for 10 min, and cell pellet was resuspended in RNALATER solution (Ambion) and stored at −80° C. The mice were then sacrificed and tissue samples of kidney, liver, brain, lung, and heart were isolated and stored in RNALATER solution (Ambion) at −80° C.

RNA isolation was carried out using the following protocol. A 50 mg section of each organ was diced, 875 µl of RLT buffer (RNEASY kit; Qiagen Inc., Valencia Calif.) was added, and the pieces were homogenized for about 20 seconds using a rotor-stator POLYTRON homogenizer (Kinematica, Inc., Cincinnati Ohio). The homogenate was microcentrifuged for 3 minutes to pellet insoluble material, the supernatant was transferred to a new tube and RNA was isolated using an RNEASY kit (Qiagen) according to the manufacturer's instructions. The RNA was eluted into 80 µL of water and quantitated with RIBOGREEN reagent (Molecular Probes, Eugene Oreg.). Genomic DNA was then removed from the RNA using a DNA-FREE kit (Ambion Inc., Austin Tex.) according to the manufacturer's instructions. The absorbance at 260 and 280 nm was measured to determine RNA purity and concentration.

Alternatively, tissue samples were diced and homogenized in TRIZOL reagent (Invitrogen Life Technologies, Carlsbad Calif.) using a rotor-stator POLYTRON homogenizer (Kinematica). Homogenates were brought to room temperature, 0.2 volumes chloroform was added, and samples were mixed vigorously. Mixtures were incubated at room temperature for several minutes and then were centrifuged at 12,000 g for 15 min at 4° C. The aqueous phase was collected and 0.5 volumes of isopropanol were added. Samples were mixed, incubated at room temperature for 10 minutes, and centrifuged for 10 min at 12,000 g at 4° C. The supernatant was removed and the pellet was washed with 75% EtOH and centrifuged at 7,500 g for 5 min at 4° C. Genomic DNA was then removed from the RNA using a DNA-FREE kit (Ambion Inc., Austin Tex.) according to the manufacturer's instructions. The absorbance at 260 and 280 nm was measured to determine RNA purity and concentration.

RNA was precipitated in 0.3 M sodium acetate (pH 5.2), 50 ng/ml glycogen, and 2.5 volumes of ethanol for one hour at −20° C. Samples were centrifuged and pellets were washed with cold 80% ethanol, dried, and resuspend in water. Double stranded cDNA was synthesized using a T7-(dT)24 first strand primer (Affymetrix, Inc., Santa Clara Calif.) and the SUPERSCRIPT CHOICE system (Invitrogen) according to the manufacturer's instructions. The final cDNA was extracted with an equal volume of 25:24:1 phenol:chloroform:isoamyl alcohol using a PHASE LOCK GEL insert (Brinkman, Inc., Westbury N.Y.). The aqueous phase was collected and cDNA was precipitated using 0.5 volumes of 7.5 M ammonium acetate and 2.5 volumes of ethanol. Alternatively, cDNA was purified using the GENECHIP sample cleanup module (Affymetrix) according to the manufacturer's instructions.

Biotin-labeled cRNA was synthesized from the cDNA in an in vitro translation (IVT) reaction using a BIOARRAY HighYield RNA transcript labeling kit (Enzo Diagnostics, Inc., Farmingdale N.Y.) according to the manufacturer's instructions. Final labeled product was purified and fragmented using the GENECHIP sample cleanup module (Affymetrix) according to the manufacturer's instructions.

Hybridization cocktail was prepared by bringing 5 µg probe to 100 µl in 1× hybridization buffer (100 mM MES, 1 M [Na$^+$], 20 mM EDTA, 0.01% Tween 20), 100 µg/ml herring sperm DNA, 500 µg/ml acetylated BSA, 0.03 nM control oligo B2 (Affymetrix), and 1× GENECHIP eukaryotic hybridization control (Affymetrix). The cocktail was sequentially incubated at 99° C. for 5 minutes and 45° C. for 5 minutes, and then centrifuged for 5 minutes. The Murine genome U74AV2 array (MG-U74Av2; Affymetrix) was brought to room temperature and then prehybridized with 1× hybridization buffer at 45° C. for 10 minutes with rotation. The buffer was then replaced with 80 µl hybridization cocktail and the array was hybridized for 16 hours at 45° C. at 60 rpm with counter balance. Following hybridization, arrays were washed once with 6×SSPE, 0.1% Tween 20, and then washed and stained using R-phycoerythrin-conjugated streptavidin (Molecular Probes, Eugene Oreg.), goat anti-streptavidin antibody (Vector Laboratories, Burlingame Calif.), and a GENECHIP Fluidics Station 400 instrument (Affymetrix) according to the manufacturer's micro_1vl protocol (Affymetrix). Arrays were analyzed using a GENEARRAY scanner (Affymetrix) and Microarray Suite software (Affymetrix).

The Murine Genome U74AV2 array (Affymetrix) represents all sequences (~6,000) in Mouse UniGene database build 74 (National Center for Biotechnology Information, Bethesda Md.) that have been functionally characterized and approximately 6,000 unannotated expressed sequence tag (EST) clusters.

Figure 5:
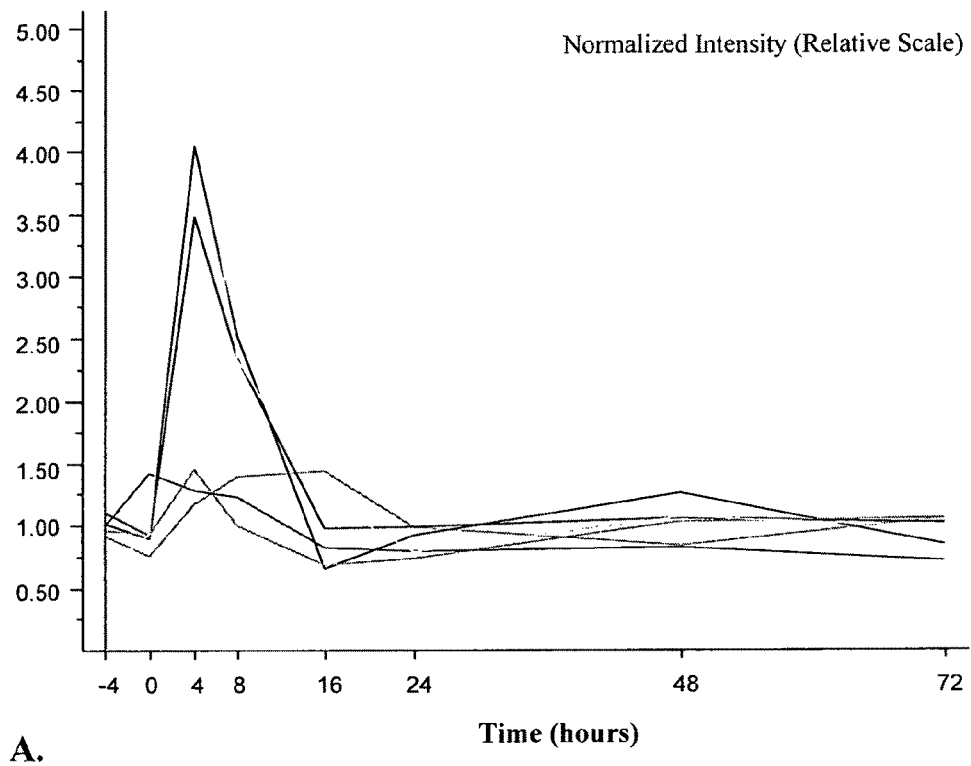
FIGS. 5A and 5B show increase in expression of angiogenic proteins in the lung of animals treated with a compound of the invention.
Figure 5:
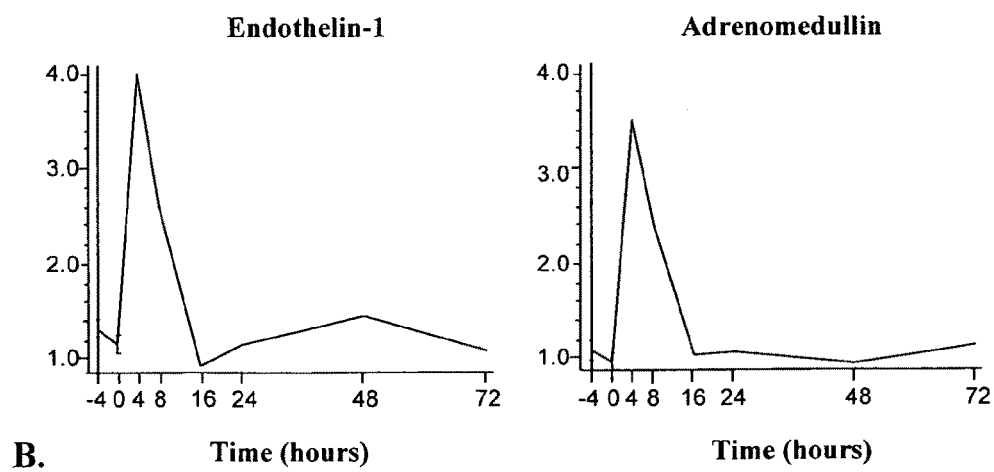

As seen in FIG. 5A, expression of genes encoding angiogenic proteins was increased in a coordinated fashion after treatment with a compound of the invention in lung, a representative organ. Transcript patterns represented in the figure include VEGF-C, Flt-1/VEGF receptor-1, adrenomedullin, endothelin-1, plasminogen activator inhibitor (PAI)-1, and Cyr61. In the time course, mRNA levels peak early, then return to control levels after 24 hours. FIG. 5B shows the specific expression time course for two genes, endothelin-1 and adrenomedullin, representative of the cluster of genes shown in FIG. 5A. In similar experiments, a significant increase was also seen for additional HIF-regulated genes including, e.g., phosphofructokinase, enolase 1, lactate dehydrogenase, glucose transporter 1, acyl CoA thioesterase, heme oxygenase, transferrin receptor, IGFBP-1, nip3, nix, and cyclin G3.

Figure 7:
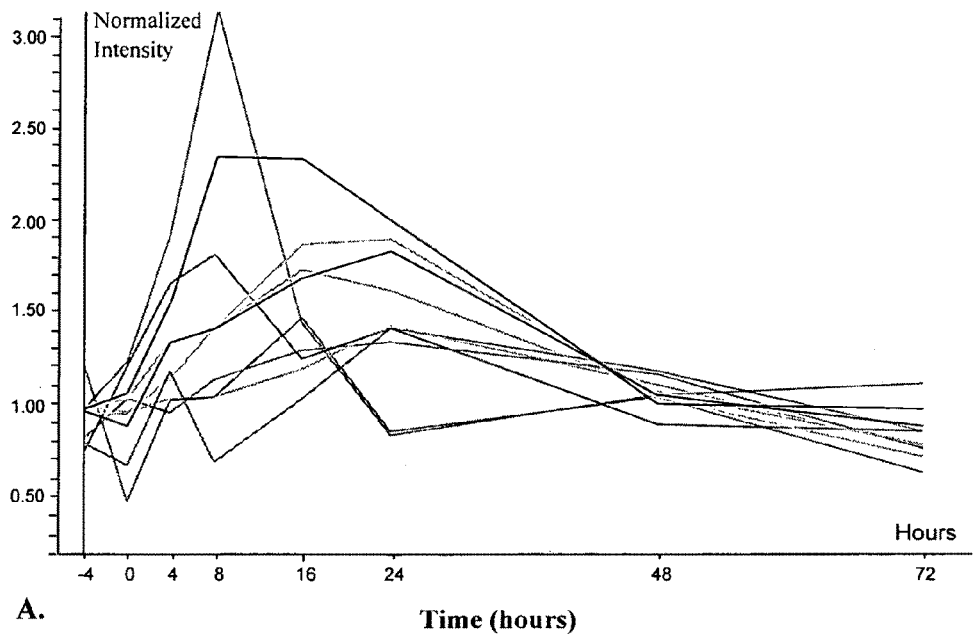
FIGS. 7A and 7B show increase in expression of glycolytic enzymes in the kidney of animals treated with a compound of the invention.
Figure 7:
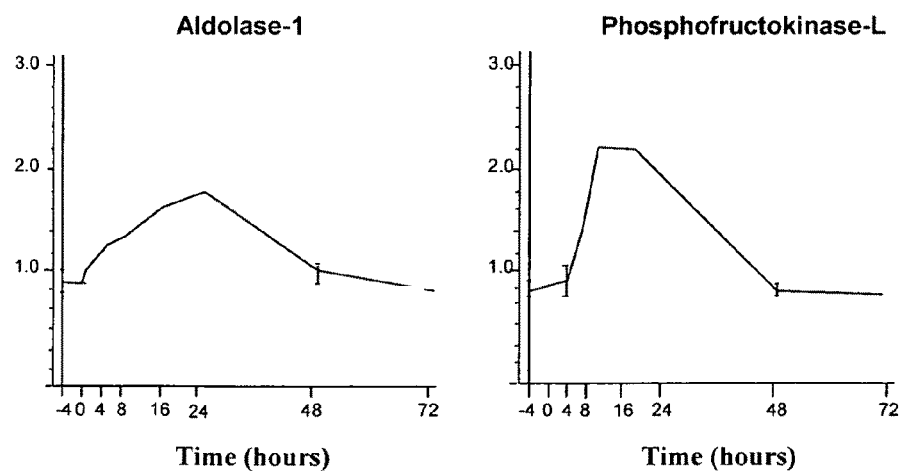

As can be seen in FIG. 7A, expression of genes encoding glycolytic enzymes was increased in a coordinated fashion after treatment with a compound of the invention in kidney, a representative organ. Transcript patterns represented in the figure include aldolase-A, enolase-1, glucose transporters (GluT)-1 and -3, GAPDH, hexokinase-1 and -2, lactate dehydrogenase-A, phosphofructokinase-L and -C, phosphoglycerate kinase-1, and pyruvate kinase-M. In the time course, mRNA levels peak early, then return to control levels after 24 hours. FIG. 7B shows the specific expression time course for two genes, aldolase and phosphofructokinase, representative of the cluster of genes shown in FIG. 7A.

Experiment II

Twelve Swiss Webster male mice (30-32 g) were obtained from Simonsen, Inc., and treated by oral gavage two times per day for 2.5 days (5 doses) with a 4 ml/kg volume of either 0.5% CMC (Sigma-Aldrich) (0 mg/kg/day) or 2.5% compound (B or E; 25 mg/ml in 0.5% CMC) (200 mg/kg/day). Four hours after the final dose, animals were anesthetized with isoflurane and a blood sample was collected from the abdominal vein. The blood sample was collected into a MICROTAINER serum separator tube (Becton-Dickinson), incubated at room temperature for 30 minutes, centrifuged at 8,000 rpm at 4° C. for 10 min, and then the serum fraction was processed and analyzed for vascular endothelial growth factor (VEGF) expression using a QUANTIKINE immunoassay (R&D Systems) according to the manufacturer's instructions. The mice were then sacrificed and approximately 150 mg of liver and each kidney were isolated and stored in RNALATER solution (Ambion) at −20° C.

RNA isolation was carried out using the following protocol. Tissue slices were cut into small pieces, 1.75 ml of RLT lysis buffer (RNEASY kit; Qiagen) was added, and the pieces were homogenized for about 20 seconds using a rotor-stator POLYTRON homogenizer (Kinematica, Inc., Cincinnati Ohio). A 350 μl volume of homogenate was micro-centrifuged for 3 minutes to pellet insoluble material, the supernatant was transferred to a new tube and RNA was isolated using an RNEASY kit (Qiagen) according to the manufacturer's instructions. The RNA was eluted into 80 μL of water and quantitated with RIBOGREEN reagent (Molecular Probes, Eugene Oreg.). Genomic DNA was then removed from the RNA using a DNA-FREE kit (Ambion) according to the manufacturer's instructions. The absorbance at 260 and 280 nm was measured to determine RNA purity and concentration.

cDNA synthesis was performed using 1W random hexamer primers, 1 μg of total RNA, and OMNISCRIPT reverse transcriptase (Qiagen), according to the manufacturer's instructions. Resulting cDNA was diluted 5-fold with water to give 100 μL final volume. Analysis of the relative level of vascular endothelial growth factor (VEGF) gene expression was performed by quantitative PCR using a FASTSTART DNA MASTER SYBR GREEN I kit (Roche Molecular Biochemicals) and VEGF-specific primers, using a LIGHTCYCLER system (Roche Molecular Biochemicals), according to manufacturer's instructions. Samples were heated to 94° C. for 6 minutes and then cycled through 95° C. for 15 seconds, 60° C. for 5 seconds, and 72° C. for 10 seconds for a total of 42 cycles. VEGF-specific primers were as follows:

```
m-VEGF-F1  GTTGCAAGGCGAGGCAGCTT    (SEQ ID NO: 1)

m-VEGF-R1  TGACGATGATGGCATGGTGGT   (SEQ ID NO: 2)
```

The relative level of 18S ribosomal RNA gene expression was measured as a control. Quantitative PCR was performed using a QUANTITECT SYBR GREEN PCR kit (Qiagen) and 18S rRNA-specific primers, using a LIGHTCYCLER system (Roche Molecular Biochemicals), according to manufacturer's instructions. Samples were heated to 95° C. for 15 minutes and then cycled through 94° C. for 15 seconds, 60° C. for 20 seconds, 72° C. for 10 seconds for a total of 42 cycles. Ribosomal RNA-specific primers were as follows:

```
18S-rat-2B  TAGGCACGGCGACTACCATCGA  (SEQ ID NO: 3)

18S-rat-2A  CGGCGGCTTTGGTGACTCTAGAT (SEQ ID NO: 4)
```

Each PCR run included a standard curve and water blank. In addition, a melt curve was run after completion of each PCR run to assess the specificity of the amplification. VEGF gene expression was normalized relative to the expression level of 18S ribosomal RNA for that sample.

Figure 6:
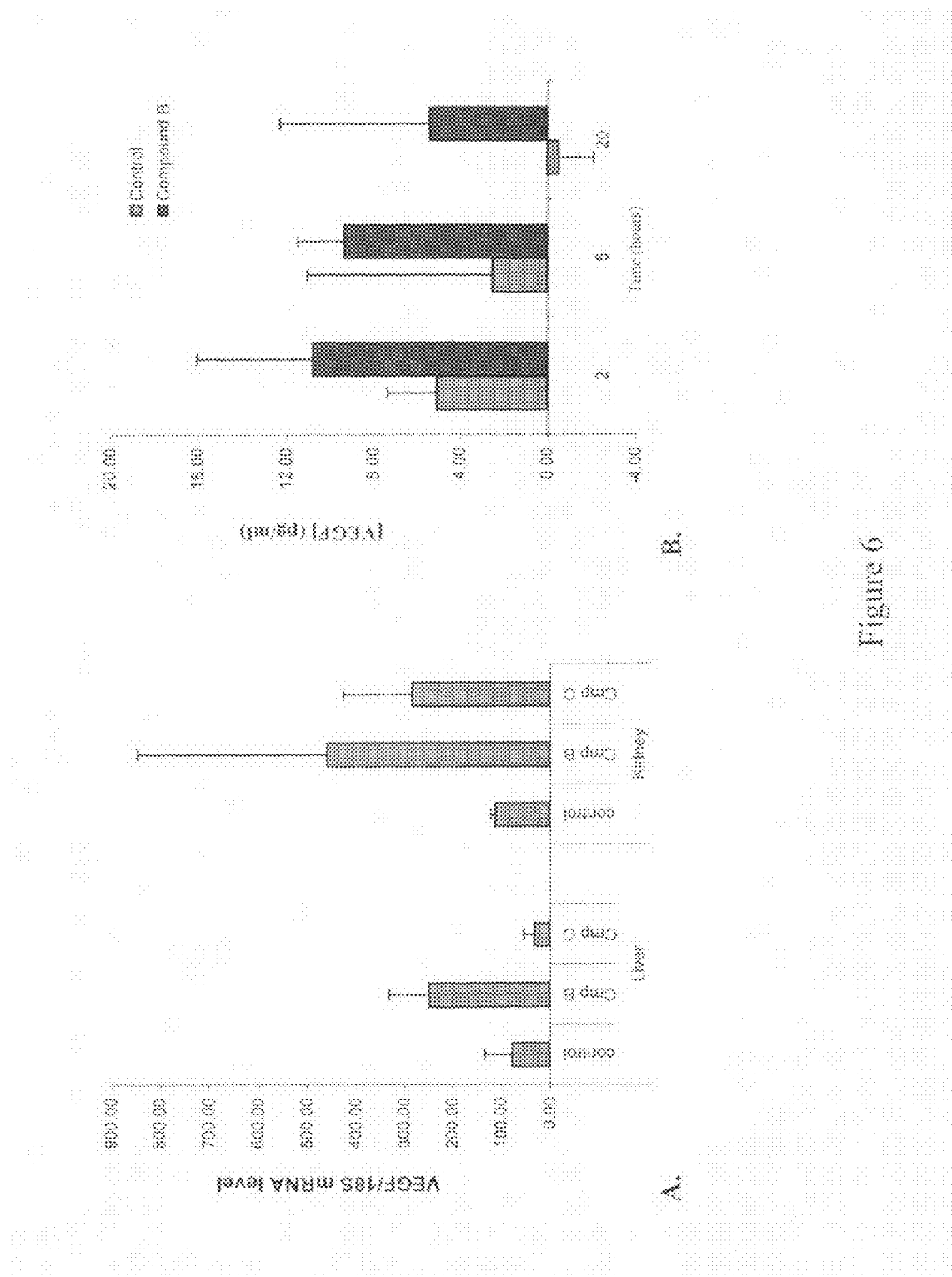
FIGS. 6A and 6B show increased expression of HIF-responsive genes in vivo.

FIG. 6A shows compound E increased VEGF expression in kidney and compound B increased VEGF expression in liver and kidney. As can be seen in FIG. 6B, levels of VEGF in the plasma of animals treated with compound are significantly increased relative to untreated control animals at 2, 5, and 20 hours after the final dose.

Example 6

Cardiac Ischemia

Experiment I

Nwogu et al. (2001; Circulation 104:2216-2221) reported the use of a compound of the invention following myocardial infarction. Although the authors interpreted their results relative to the compounds affect on fibrosis, the present invention clearly shows that the primary benefit on heart performance is due to stabilization of HIFα. Experiments are as described in Nwogu et al. (supra) and as described below.

Seventy adult male Wistar rats (200-250 g) were anaesthetized and subjected to left coronary artery occlusion to produce acute myocardial infarction (AMI). Nine animals were subjected to identical surgery without coronary artery ligation. Twenty-four to forty-eight hours after surgery, electrocardiogram (ECG) electrodes were applied to the paws and a 15 MHz linear probe (Acuson Corp., Mountain View Calif.) was applied to the chest to obtain short axis transthoracic echocardiography (2DE) images at the mid-papillary muscle level. The probe was moved cephalad or caudad and angulated until clear endocardial visualization of the left ventricular cavity was detected. Images were obtained using the *Sequoia* ultrasound system (Acuson). Animals with less than 20% fractional shortening and regional wall motion abnormality on the 2DE were randomized to treatment with compound A (n=14) or vehicle (n=12). The sham controls were also randomized to treatment with compound A (n=4) or vehicle (n=5).

Animals were treated by gavage 2 times per day for the duration of the experiment with compound A at 50 mg/kg or with vehicle alone. Serum level of drug was determined periodically to establish that treated animals received sufficient and consistent amount of drug and that the measured levels were sufficient to inhibit prolyl 4-hydroxylase, a representative 2-oxoglutarate dioxygenase.

Serial 2DE images were obtained weekly. Three short axis 2DE digital clips containing 5 or more systolic and diastolic frames were captured and stored. Two observers blinded to treatment did measurements off-line. For the measurements, the digital images were slowed and frozen at end systole and end diastole. Two systolic and two diastolic frames from each of the three digital clips were measured by consensus and averaged. The anterior wall in systole (AWS) and diastole (AWD), posterior wall in systole (PWS) and diastole (PWD), and left ventricular end systolic (LVESD) and end diastolic (LVEDD) were measured according to the American Society for Echocardiology (ASE) leading-edge method. For consistency, measurements were done from the anterior to the posterior mid points of the left ventricular cavity and were randomly repeated to ensure reproducibility (reproducibility was approximately 96%).

At four weeks of treatment, in vivo hemodynamic measurements were determined, as described below, both before and after infusion (0.2 ml over 1 minute) of $10^7$ M isoproterenol via the femoral vein. Hearts were then excised and weighed as described below.

Alternatively, one hundred forty adult male Wistar rats (200-250 g) were anaesthetized and subjected to left coronary artery occlusion to produce AMI. Forty-eight hours after surgery, 2DE images were obtained and animals with a significant area of infarction were randomized to treatment with compound A (n=34) or vehicle (n=34).

Animals were treated by gavage 2 times per day for the duration of the experiment with compound A at 50 mg/kg or with vehicle alone. Serum level of drug was determined periodically to establish that treated animals received sufficient and consistent amount of drug and that the measured levels were sufficient to inhibit prolyl 4-hydroxylase.

Digital mid-papillary muscle and apical four chamber 2DE images were obtained biweekly on half of the animals in each group until week 8. Two observers blinded to treatment did measurements off-line. For the measurements, the digital images were slowed and frozen at end systole and end diastole. Two to three endocardial surfaces were traced in both the short axis and four chamber views and averaged. The left ventricular area in systole and diastole, ejection fraction, fractional area change, wall thickness, mitral peak E wave velocity, aortic peak velocity, and infarct size were measured.

After 10 weeks of treatment, in vivo hemodynamic measurements were determined and hearts were excised and weighed as described below.

To collect in vivo hemodynamic measurements, animals were anaesthetized and the right carotid artery was dissected free from surrounding tissues and canulated with an SPR-671 ultra-miniature pressure transducer (Millar Instruments, Inc., Houston Tex.). The catheter was then advanced into the left ventricle. After steady state was established, baseline heart rate (HR), developed pressure (DP), contractile index (CI), left ventricle systolic pressure (SBP) and end diastolic pressure (LVEDP), and maximal rate of pressure rise and fall (+dP/dt and −dP/dt, respectively) were recorded.

Following hemodynamic measurement, hearts were excised and weighed. Pieces of scarred myocardium, and right ventricle and left ventricle myocardium distant from the site of infarct were dissected out and weighed. Hydroxyproline and proline were determined by the method of Palmerini et al. (1985, J Chromatogr 339:285-92) except that L-azetidine-2-carboxylic acid (Sigma-Aldrich) was substituted for 3,4-dehydroproline as the internal standard.

Figure 8:
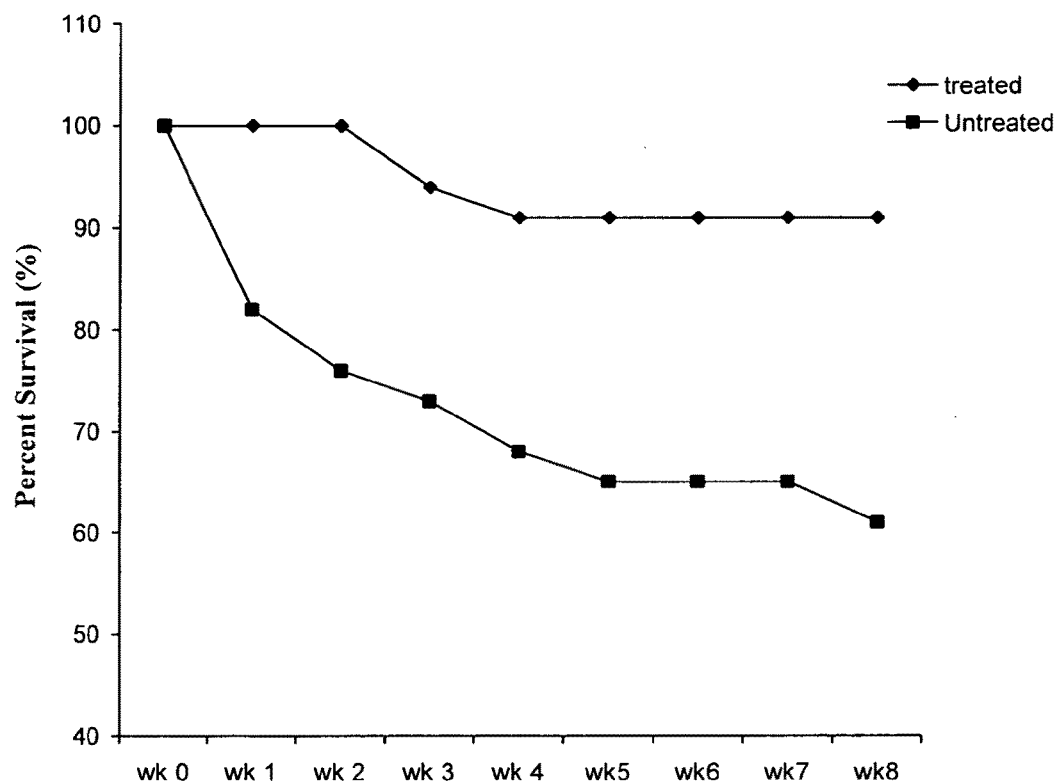
FIG. 8 shows percent survival in a group treated with a compound of the invention (n=34) compared to an untreated group (n=34) at time intervals following induced myocardial infarction.

An immediate reduction in mortality was seen when compounds of the invention were administered following myocardial infarction. As can be seen in FIG. 8, no deaths were seen in the treated group immediately following insult to the heart, and over 90% of the treated group was still alive 8 weeks later. In comparison, only about 60% of the untreated group survived this period. Statistically significant improvement in survival (P<0.05) in the treated group relative to untreated group was seen at weeks 2 through 8, with a relative reduction in mortality of 77%.

Heart parameters were also improved in the treated group over the untreated group. Table 1 shows no increase in left ventricle end diastolic diameter (LVEDD) in the treated group, whereas the untreated group shows an increase in both LVEDD and left ventricle end systolic diameter (LVESD) measures over the same time period. The dilation of the heart in the untreated group was statistically different in the treated group relative to the untreated group after 1 week of treatment.

TABLE 1

Changes in left ventricle end diastolic diameter.

| Week | Treated-MI (mm) | Untreated-MI (mm) | Sham (mm) |
| --- | --- | --- | --- |
| 0 | 69 ± 1 | 67 ± 2 | 43 ± 3 |
| 1 | 68 ± 2 | 76 ± 2 | 44 ± 3 |
| 2 | 69 ± 3 | 74 ± 4 | 45 ± 2 |
| 3 | 68 ± 4 | 75 ± 3 | 45 ± 2 |

Values in the table represent the mean ± standard deviation.

TABLE 2

Changes in left ventricle end systolic diameter.

| Week | Treated-MI (mm) | Untreated-MI (mm) | Sham (mm) |
| --- | --- | --- | --- |
| 0 | 77 ± 2 | 75 ± 1 | 67 ± 2 |
| 1 | 82 ± 2 | 88 ± 1 | 65 ± 2 |
| 2 | 85 ± 2 | 86 ± 3 | 69 ± 2 |
| 3 | 85 ± 3 | 86 ± 2 | 68 ± 4 |

Values in the table represent the mean ± standard deviation.

Figure 9:
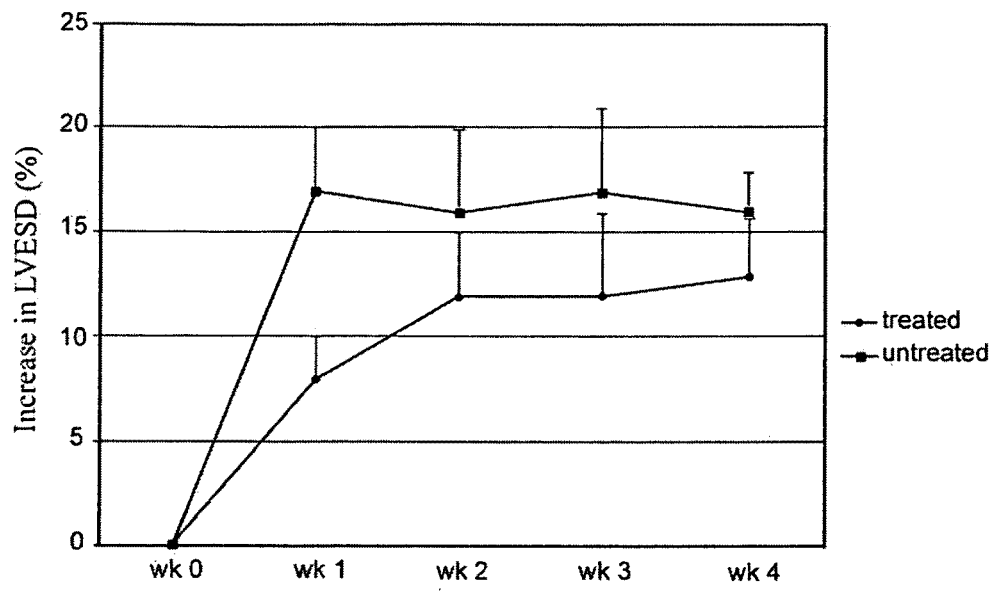
FIGS. 9A and 9B show improvement in cardiac architecture following myocardial infarction in animals treated with a compound of the invention relative to untreated controls.
Figure 9:
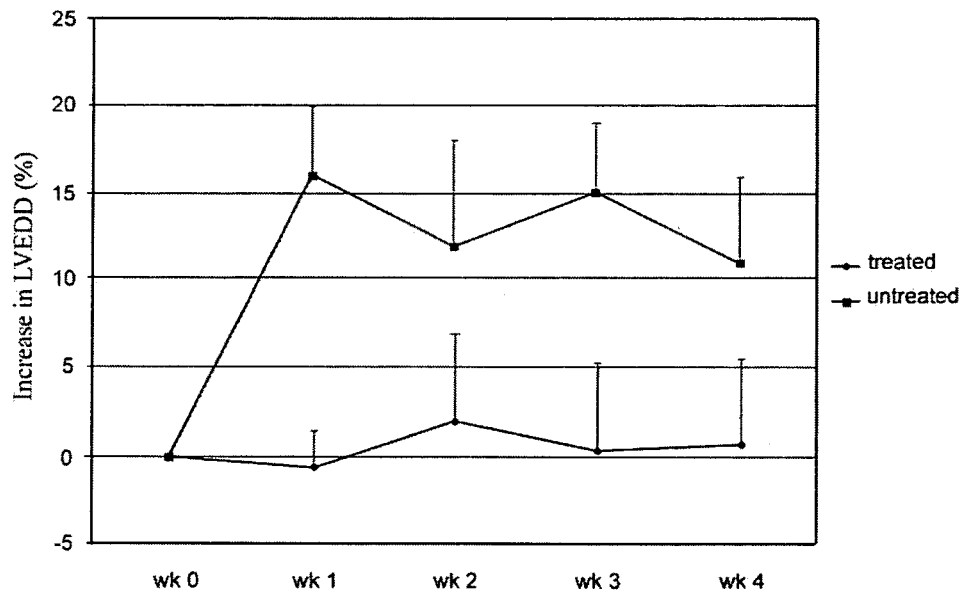
Figure 10:
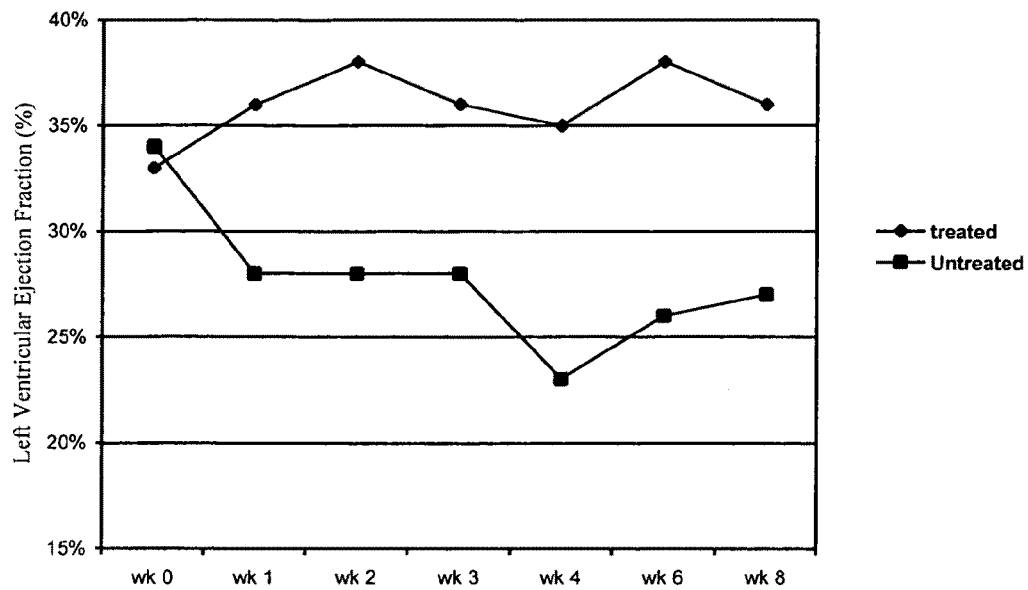
FIGS. 10A and 10B show improvement in cardiac performance following myocardial infarction in animals treated with a compound of the invention relative to untreated controls.
Figure 10:
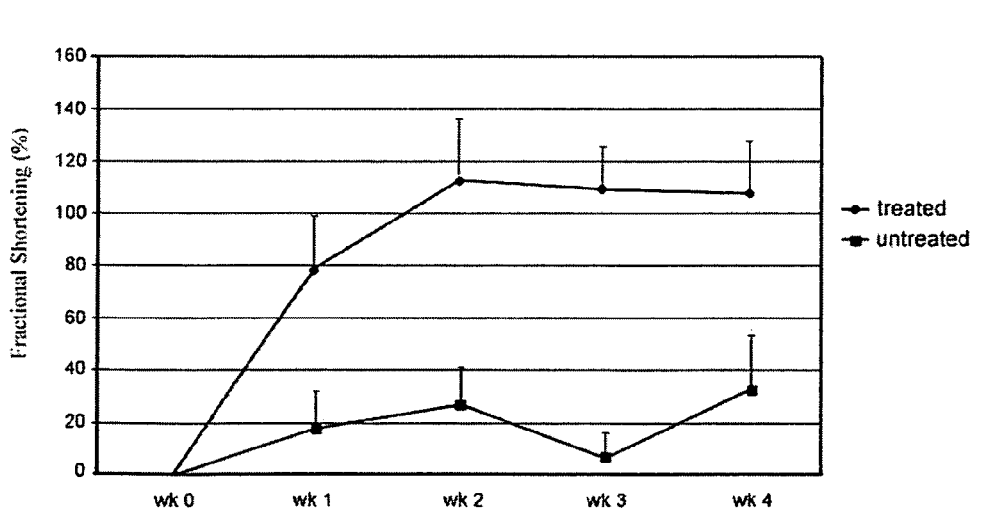

FIGS. 9A and 9B show graphical representations of the increase in LVESD and LVEDD, respectively, over time. The left ventricle end diastolic and systolic diameters were similar in the three groups at the time of randomization. FIG. 10A shows statistically significant improvement in left ventricular ejection fraction (LVEF) in treated animals relative to untreated controls in weeks 2 through 8. At randomization, the LVEF for both groups was 33%. The apparent increase in LVEF between week 4 and week 6 in the untreated control group reflects the high mortality in members of this group.

Fractional shortening of the myocardium during contraction was also improved in the treated group. Table 3 shows statistically significant improvement in fractional shortening in the treated group relative to the untreated group in weeks 1 to 4.

TABLE 3

Changes in fractional shortening.

| Weeks | Treated-MI (%) | Untreated-MI (%) | Sham (%) |
|---|---|---|---|
| 0 | 10 ± 0.8 | 12 ± 1 | 34 ± 3 |
| 1 | 17 ± 1 | 13 ± 1 | 33 ± 3 |
| 2 | 20 ± 2 | 15 ± 2 | 33 ± 2 |
| 3 | 21 ± 2 | 12 ± 1 | 35 ± 2 |
| 4 | 21 ± 3 | 16 ± 2 | 36 ± 1 |

Values in the table represent the mean ± standard deviation.

Further, as can be seen in FIG. 10B, fractional shortening in the treated group increased from 10% at baseline to 20% at week 2, a 79% increase relative to baseline. Both the untreated group and sham controls remained unchanged over the 4 week period.

Figure 11:
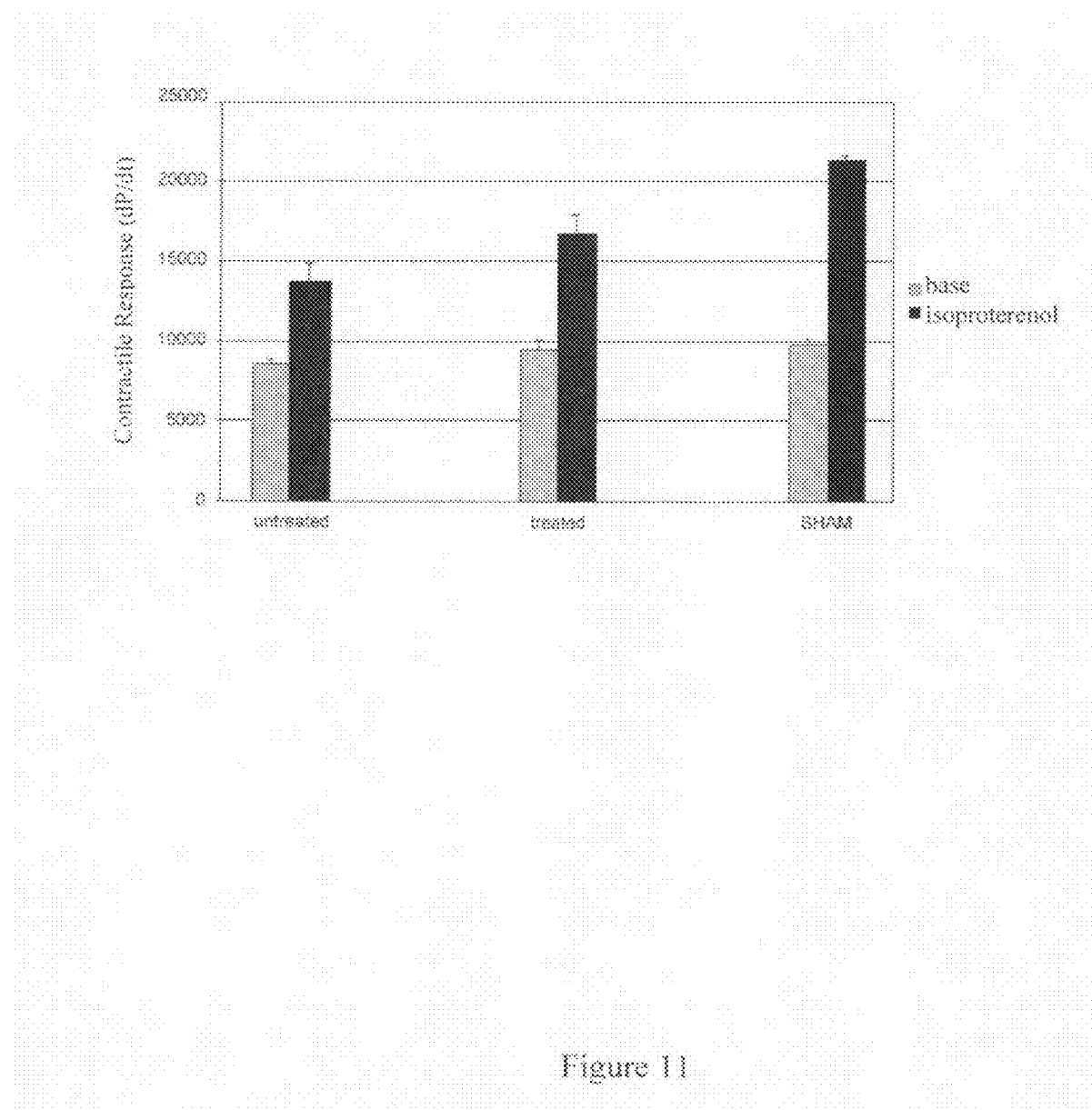
FIG. 11 shows the contractile response of the heart 4 weeks post-MI in a group treated with a compound of the invention relative to an untreated group with and without an isoproterenol challenge.

The ability of the heart to contract and relax following trauma induced by cardiac ischemia was also improved in the treated group. Table 4A shows statistically significant differences in negative change in pressure over time (−dP/dt), a measure of the hearts ability to relax following contraction, in the treated group relative to the untreated group following 4 weeks of treatment. As shown in Table 4A and in FIG. 11, stimulation of the heart with isoproterenol shows statistically significant differences in positive change in pressure over time (+dP/dt), a measure of the hearts ability to contract, in the treated group relative to the untreated group.

TABLE 4A

Hemodynamic data at 4 weeks post-MI.

| | Treated-MI | Untreated-MI | Sham |
|---|---|---|---|
| Systolic BP (mm Hg) | | | |
| baseline | 143 ± 7 | 142 ± 3 | 144 ± 5 |
| isoproterenol | 130 ± 9 | 123 ± 7 | 197 ± 3 |
| Developed pressure (mm Hg) | | | |
| baseline | 133 ± 6 | 133 ± 3 | 135 ± 6 |
| isoproterenol | 121 ± 9 | 115 ± 8 | 173 ± 3 |
| +dP/dt (mm Hg/sec) | | | |
| baseline | 9477 ± 581 | 8642 ± 209 | 9925 ± 1194 |
| isoproterenol | 16830 ± 1195 | 13832 ± 1097 | 21515 ± 1074 |
| −dP/dt (mm Hg/sec) | | | |
| baseline | 9978 ± 827 | 8009 ± 426 | 11578 ± 622 |
| isoproterenol | 9234 ± 703 | 8984 ± 622 | 11549 ± 10742 |

Values in the table represent the mean ± standard deviation.

Table 4B shows statistically significant differences in both +dP/dt and −dP/dt in the treated group relative to the untreated group following 10 weeks of treatment.

TABLE 4B

Hemodynamic data at 10 weeks post-MI.

| | Treated-MI | Untreated-MI | P-value |
|---|---|---|---|
| Systolic BP (mm Hg) | 106 ± 4 | 92 ± 5 | 0.053 |
| Developed pressure (mm Hg) | 97 ± 3 | 69 ± 14 | 0.031 |
| +dP/dt (mm Hg/sec) | 6701 ± 331 | 4937 ± 828 | 0.042 |
| −dP/dt (mm Hg/sec) | 6395 ± 373 | 3641 ± 737 | 0.002 |

Values in the table represent the mean ± standard deviation.

Significant improvement was also seen at 10 weeks in developed pressure and systolic blood pressure in the treated group relative to the untreated group.

While it is recognized that recovery from an initial infarct requires connective tissue deposition within the necrotic region, the present invention demonstrates no adverse affects of treatment with respect to scar formation. On the contrary, as can be seen in Table 5A, there is no statistically significant change in collagen deposition in the scar and non-infracted tissue at 4 weeks, demonstrating the improvement in heart performance in the first 4 weeks is unrelated to collagen deposition.

TABLE 5A

Collagen content in the heart at 4 weeks post-Ml.

| | Treated-MI | Untreated-MI | Sham |
|---|---|---|---|
| Hydroxyproline/proline in non-infarct left ventricular myocardium | 0.12 ± 0.06 | 0.18 ± 0.05 | 0.11 ± 0.02 |
| Hydroxyproline/proline in non-infarct right ventricular myocardium | 0.13 ± 0.02 | 0.17 ± 0.03 | 0.15 ± 0.03 |
| Hydroxyproline/proline in infarct scar | 0.34 ± 0.08 | 0.45 ± 0.09 | — |

Values in the table represent the mean ± standard deviation.

However, as can be seen in Table 5B, there is a statistically significant absolute reduction in the collagen content of the non-infracted myocardium and scar tissue of the treated group relative to the untreated group at 10 weeks, demonstrating that the methods of the present invention do reduce reactive cardiac fibrosis over a longer time course.

TABLE 5B

Collagen content in the heart at 10 weeks post-MI.

| | Treated-MI | Untreated-MI | P-value |
|---|---|---|---|
| Hydroxyproline/proline in non-infarct left ventricular myocardium | 0.099 ± 0.025 | 0.135 ± 0.036 | <0.05 |
| Hydroxyproline/proline in non-infarct right ventricular myocardium | 0.152 ± 0.044 | 0.175 ± 0.042 | — |
| Hydroxyproline/proline in infarct scar | 0.471 ± 0.024 | 0.638 ± 0.020 | <0.05 |

Values in the table represent the mean ± standard deviation.

Experiment II

Male Wistar rats (100-110 g), aged 4-5 weeks, were kept on a regular diet and a 12 hour day-night cycle. The animals were randomized into treatment regimens as follows: (1) Sham operated animals (n=12), (2) myocardial infarction controls (n=25), and (3) myocardial infarction with compound B treatment (n=25). Animals were treated for two days prior to surgery and for one week following surgery. Animals were treated by oral gavage two times per day with either 0.5% CMC (Sigma-Aldrich) (control) or 50 mg/kg compound B in 0.5% CMC. Ligation of the left anterior descending coronary artery was performed in artificially ventilated animals after left thoracotomy. Animals were sacrificed one week after surgery and echocardiography was performed. Fractional shortening, end-diastolic diameters, and end-systolic diameters were determined in a blinded fashion.

Figure 12:
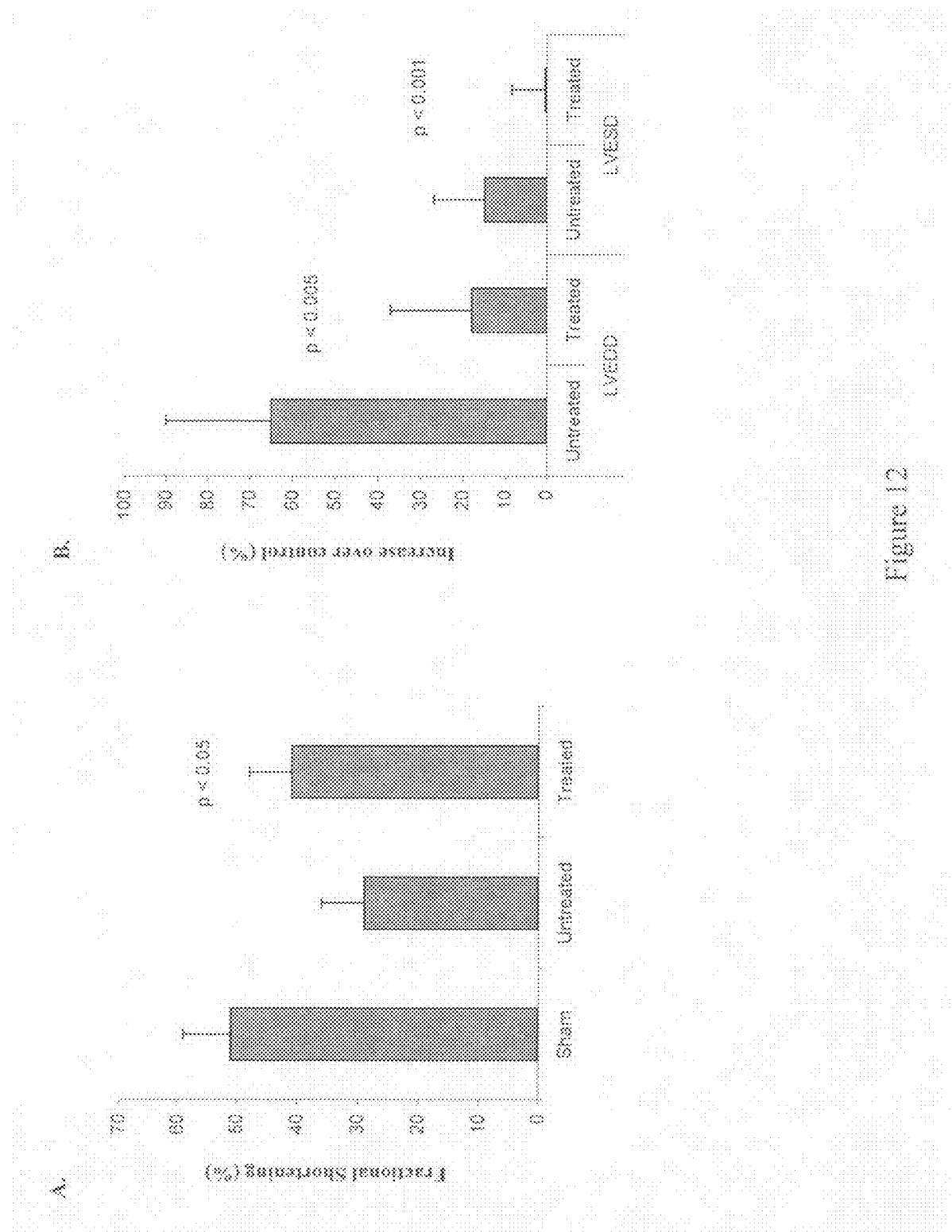
FIGS. 12A and 12B show improvements to heart architecture following myocardial infarction in animals pretreated with a compound of the invention relative to untreated controls.

As can be seen in FIG. 12A, fractional shortening was reduced from 51% in sham-operated animals to 29% in untreated MI controls. Treatment with compound showed a statistically significant ($p<0.05$; one-way ANOVA/Turey's test) improvement in fractional shortening, to 41%, relative to the untreated control group. Similarly, FIG. 12B shows statistically significant improvement in left ventricular end-diastolic (LVEDD) and end-systolic (LVESD) diameters in treated animals relative to untreated MI controls (p<0.005 and p<0.001, respectively; one-way ANOVA/Turey's test). Animals treated with compound showed no increase in left ventricular end-systolic diameter and an 18% increase in end-diastolic diameter over sham operated animals. The untreated controls, however, showed a 15% and 65% increase in LVESD and LVEDD, respectively.

Example 7

Liver Ischemia

Bickel et al. (1998; Hepatology 28:404-411) reported the use of a compound of the invention following induction of toxic-ischemic injury in the liver. Although the authors interpreted their results relative to the effect of the compounds on fibrosis, the authors acknowledged that the beneficial effects on variables of liver function including serum levels of bilirubin, bile acids, and alkaline phosphatase could not be directly attributed to a reduction in fibrosis.

The model of toxic-ischemic liver injury was described in Bickel et al. (supra). Briefly, male Wistar rats (212-320 g) either received 1 ml/kg carbon tetrachloride ($CCl_4$) in olive oil (1:1) by gavage twice weekly for nine weeks (n=140) or received no treatment (controls; n=10). Additionally, a group of animals receiving $CCl_4$ (n=60) also received compound P. The compound was administered by intraperitoneal injection twice daily at 60 mg compound/2 ml saline/kg body weight. After 9 weeks, the animals were sacrificed and the liver was weighed. Bilirubin, alanine transaminase, alkaline phosphatase, albumin, and total bile acids in serum were determined using commercially available kits.

As can be seen in Table 6 (Bickel et al., supra, Table 2), induction of liver damage produced a significant reduction in body weight (BW), although no significant change in liver weight was seen (not shown).

TABLE 6

Serum parameters of liver function after 9 weeks of treatment.

| Treatment | N | BW (g) | BR (µmol/L) | tBA (µmol/L) | ALT (U/L) | AP (U/L) |
|---|---|---|---|---|---|---|
| Control | 10 | 425 ± 66.9 | 2.00 ± 0.50 | 8.48 ± 8.40 | 27.5 ± 10.9 | 156 ± 57.5 |
| $CCl_4$ | 80 | 370 ± 43.3 | 4.34 ± 3.93 | 81.3 ± 87.9 | 83.1 ± 51.7 | 269 ± 117 |
| $CCl_4$ + CPD | 60 | 373 ± 38.9 | 2.83 ± 2.21 | 40.8 ± 51.4 | 59.0 ± 29.5 | 195 ± 72.7 |

Values in the table represent the mean ± standard deviation.

Liver damage also produced a measurable and statistically significant decrease in liver function as determined by serum levels of bilirubin (BR), total bile acids (tBA), alanine transaminase (ALT), and alkaline phosphatase (AP), which increased 117%, 856%, 201%, and 72%, respectively. However, treatment with a compound of the invention (CPD) produced statistically significant improvement in liver function. Serum levels of BR, tBA, ALT, and AP decreased 64%, 65%, 43%, and 65%, respectively, in the treated group relative to the untreated group. The improvement in liver function is attributed to stabilization of HIFα by the methods of the invention.

Example 8

Renal Ischemia-Reperfusion Injury

The model of ischemic acute renal failure was described in Nemoto et al. (2001, Kidney Int 59:246-251.) Briefly, male Sprague-Dawley rats (200-250 g) were treated with either 0.5% carboxymethyl cellulose (CMC; Sigma-Aldrich) or 1.5% compound B suspended in CMC by oral gavage in a volume of 4 ml/kg/day. Rats were pretreated daily for 4 consecutive days (days −3 to 0). A few hours after the fourth and last oral dose on day 0, renal ischemia-reperfusion injury (IRI) was performed.

Animals were divided into four groups: (1) Vehicle pretreatment and sham surgery; (2) compound B pretreatment and sham surgery; (3) vehicle pretreatment and IRI surgery; and (4) compound B pretreatment and IRI surgery. Animals were anesthetized under isoflurane, an incision was made in the abdominal midline, and the renal pedicles were bluntly dissected. A vascular clip was placed on the right renal pedicle for 45 minutes while the left kidney underwent simultaneous nephrectomy. After each occlusion, the clip was released at 45 minutes, and reperfusion was observed by the changing color of the kidney. Temperature was maintained constant, and warm saline (0.5% of body weight) containing Buprenex analgesic was administered directly into abdomen before the incision was completely sutured.

The animal body weight and mortality were monitored. Blood samples were obtained from the tail vein, and serum chemistry and CBC were measured by IDEXX veterinary service (West Sacramento Calif.). Data are presented as mean±SE with number of animals in parenthesis. The data were compared within the four groups at each time point using one-way analysis of variance (ANOVA, SIGMASTAT) and Student-Newman-Keuls method. A value of P<0.05 was considered significant.

Figure 13:
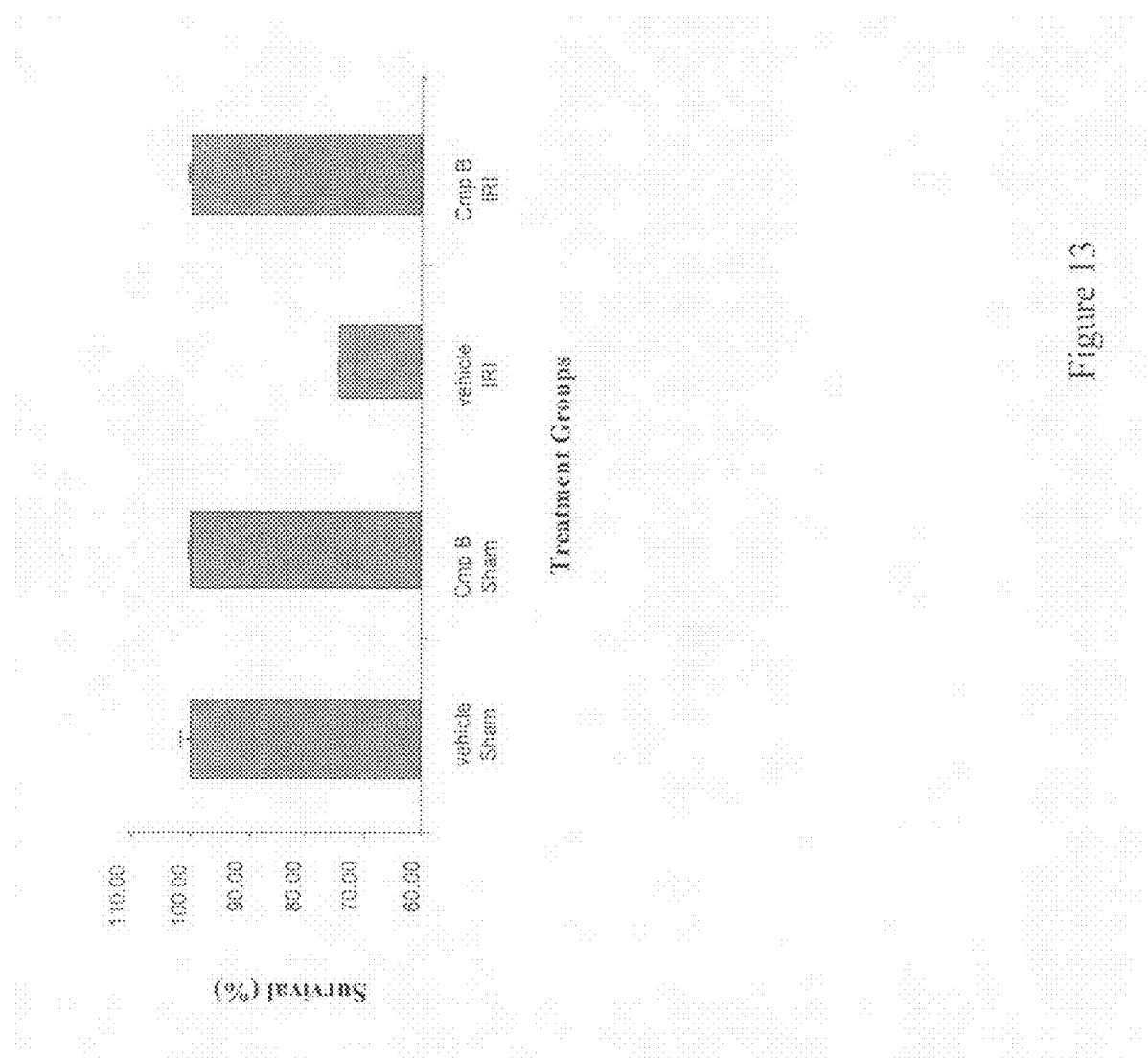
FIG. 13 shows increased survivability in animals subjected to renal ischemic-reperfusion injury that have been pretreated and consequently treated with compounds of the invention relative to untreated and sham-operated controls.
Figure 14:
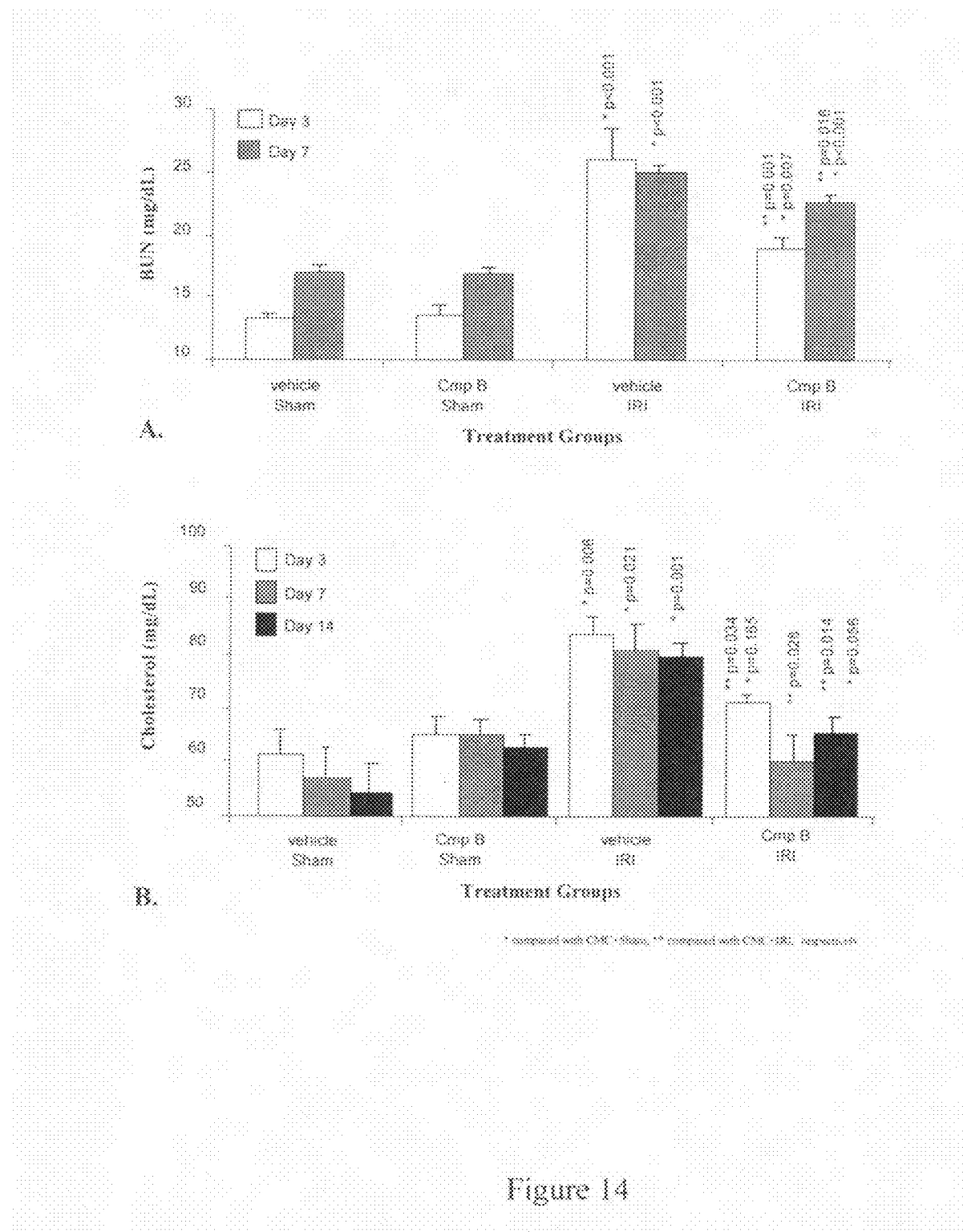
FIGS. 14A and 14B show improvement in kidney function following ischemic-reperfusion injury in animals pretreated with a compound of the invention relative to untreated controls.

As can be seen in FIG. 13, treatment with the compound prevented early mortality associated with ischemic-reperfusion injury. Further, serum blood urea nitrogen (BUN), a gauge of renal function, was significantly elevated by renal IRI at both 3 and 7 days, whereas treatment with compound produced significantly less IRI-induced increase in BUN. (FIG. 14A.) Additionally, serum cholesterol was significantly elevated by renal IRI at days 3, 7 and 14, whereas treatment with compound completely blocked IRI-induced increase in serum cholesterol. (FIG. 14B.) Although the reasons are still under investigation, elevated kidney cholesterol is a natural reflection of renal ischemic-reperfusion injury. (Zager et al. (2001) Am J Pathol 159:743-752; Appel (1991) Kidney Int 39:169-183; and Abdel-Gayoum et al. (1999) Hum Exp Toxicol 18:454-459.)

Example 9

Enhanced Granulation Tissue Formation in Chronic Wounds

The ability to treat chronic wounds utilized the rabbit cutaneous hypertrophic scarring model described in Morris et al. (1997, Plast Reconstr Surg 100:674-681) and Marcus et al. (2000, Plast Reconstr Surg 105:1591-1599). Briefly, female New Zealand White rabbits (n=12; 3-6 months of age) were anesthetized and four, 7-mm dermal ulcer wounds were created on the ventral surface of each ear with removal of the perichondrium. Wounds were treated and covered with TEGADERM semi-occlusive polyurethane dressing (3M Health Care, St. Paul Minn.). Wounds were treated by topical application of 0.5% or 1% (w/v) a prodrug of compound V [pV] in an aqueous 0.5% (w/v) CARBOPOL 971 PNF gel (pH 6.5; Noveon Inc., Cleveland Ohio) once per day for the first week. When tested in vitro, gels released 50% of the drug within 2 hrs and 95% of the drug within 4 hrs. The treatment ear received either a low-dose treatment (0.5% compound) or a high dose treatment (1% compound), while the control ear received gel alone. Treatment delivery was facilitated by creating a hole in the dressing applied at the time of wounding to prevent irritation of the area surrounding the wound by daily removal of dressing. The hole was then covered by a smaller piece of dressing to prevent wound desiccation. Wounds with obvious desiccation or infection were excluded from the study.

At post-wounding days 7 and 12, wounds were harvested, bisected, and stained with hemotoxylin-eosin for evaluation of granulation tissue formation and wound epithelialization. Observers blinded to treatment quantitated wound healing parameters in histological sections by the use of a graduated eyepiece reticle. Data were analyzed using the Student's t-test to compare treated and untreated samples. A P<0.05 was considered significant.

Figure 15:
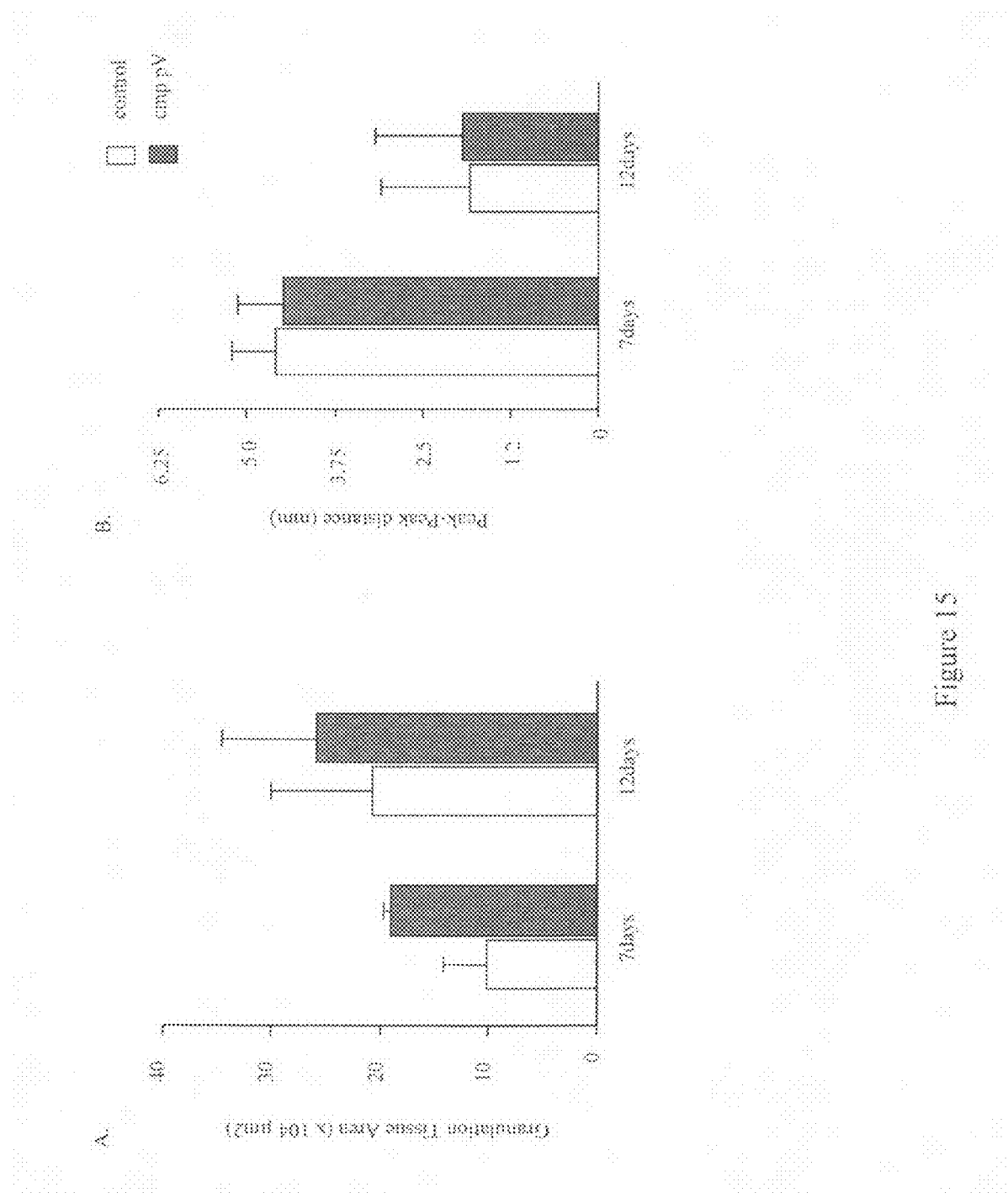
FIGS. 15A and 15B show improved healing of chronic wounds in animals treated with a compound of the invention relative to untreated controls.

The wounds were evaluated for granulation tissue formation and wound epithelialization; parameters of wound healing that are sensitive ischemia and hypoxia. (Corral et al. (1999) Arch Surg 134:200-205; and Ahn and Mustoe (1990) Ann Plast Surg 24:17-23.) As shown in FIG. 15A, an increase in granulation tissue area was seen in treated wounds relative to untreated wounds. As can be seen in FIG. 15B, there was no difference in the peak-to-peak distance in treated versus untreated animals. The peak-to-peak value is an indictor of wound coverage by granulation tissue. Thus, the methods of the invention can be used to increase vascularization and granulation tissue formation in wounds, such as chronic wounds and ulcers.

Example 10

Screening Assay

Compounds that inhibit HIF-specific prolyl hydroxylase activity and thereby stabilize HIFα can be identified and characterized using the following assay. A 50 µl aliquot of a reaction mix containing 4 mg/ml BSA, 0.1 M Tris HCl (pH 7.2), 2 mM ascorbate, 80 µM ferrous sulfate, 0.2 mM 2-oxoglutarate, 600 units/ml catalase, with or without 100 µM HIFα peptide is mixed with 50 µl HeLa cell extract or purified HIF prolyl hydroxylase and incubated 1.5 hours at 37° C. Following incubation, 50 µl of streptavidin beads are added and the mixture is incubated for 1 hour with agitation at 4° C. The mixture is transferred to tubes and centrifuged at low speed to pellet the beads. The beads are washed three times with 0.5 to 1 ml 20 mM Tris HCl (pH 7.2). The peptide is then eluted from the beads with 5 µl 2 mM biotin in 20 mM Tris HCl (pH 7.2) for 1 hour. The tubes are centrifuged to pellet the resin and 40-50 µl of supernatant is removed and an equal volume of acetonitrile is added. Alternatively, the peptide is attached to methoxycoumarin, a pH insensitive fluorophore. The fluorophore may provide sensitivity and specificity to enhance detection in assays run with crude cell lysate. An exemplary HIF peptide for use in the screening assay may comprise [methoxycoumarin]-DLDLEALAPYIPAD-DDFQL-amide (SEQ ID NO:5). The non-hydroxylated and hydroxylated peptides are then separated by reverse-phase HPLC on a C18 column with UV detection at 214 nm.

Various modifications of the invention, in addition to those shown and described herein, will become apparent to those skilled in the art from the foregoing description. Such modifications are intended to fall within the scope of the appended claims.

All references cited herein are hereby incorporated by reference herein in their entirety.

What is claimed is:

1. A method for treating a hypoxic or ischemic disorder or condition in a subject, the method comprising administering to the subject an effective amount of a heterocyclic carboxamide compound that stabilizes the alpha subunit of hypoxia inducible factor (HIFα).

2. The method of claim 1, wherein the heterocyclic carboxamide compound inhibits HIF prolyl hydroxylase enzyme activity.

3. The method of claim 1, wherein the hypoxic or ischemic disorder or condition is associated with an ischemic event.

4. The method of claim 3, wherein the ischemic event is acute.

5. The method of claim 3, wherein the ischemic event is associated with surgery, organ transplantation, infarction, trauma, or injury.

6. The method of claim 1, wherein the ischemic disorder or condition is chronic.

7. The method of claim 1, wherein the hypoxic or ischemic disorder or condition is associated with ischemic reperfusion injury in a subject.

8. The method of claim 1, wherein the administering is oral administration.

* * * * *